United States Patent [19]

Schoenleber et al.

[11] Patent Number: 4,963,568

[45] Date of Patent: Oct. 16, 1990

[54] DOPAMINE AGONISTS

[75] Inventors: Robert W. Schoenleber, Deerfield; John W. Kebabian, Lake Bluff; Yvonne C. Martin, Waukegan; Michael P. DeNinno, Wildwood; Richard J. Perner, Gurnee; David M. Stout, Mettawa; Chi-Nung W. Hsiao, Libertyville; Stanley DiDomenico, Jr., Ingleside; John F. DeBernardis, Lindenhurst; Fatima Z. Basha, Lake Forest; Michael D. Meyer, Lindenhurst; Biswanath De, Vernon Hills, all of Ill.

[73] Assignee: Abbott Laboratories, Abbott Park, Ill.

[21] Appl. No.: 359,448

[22] Filed: May 31, 1989

[51] Int. Cl.$^5$ .................. C07D 311/04; C07D 405/06; C07C 211/03; A61K 31/35

[52] U.S. Cl. .................. 514/320; 514/231.5; 514/278; 514/359; 514/409; 514/422; 514/428; 514/451; 514/454; 514/456; 544/69; 544/70; 544/151; 546/13; 546/15; 546/269; 548/407; 548/525; 548/569; 549/213; 549/331; 549/359; 549/406; 59/407; 59/408; 564/337; 564/428

[58] Field of Search .............. 549/331, 406, 407, 408, 549/213, 359; 564/337, 428; 544/151, 69, 70; 514/320, 359, 231.5, 451, 409, 422, 428, 278, 454, 456; 546/269, 13, 15; 548/525, 569, 407

[56] References Cited

U.S. PATENT DOCUMENTS 4,874,756 10/1989 Mertens et al. .................. 514/231.5

Primary Examiner—Mary C. Lee
Assistant Examiner—Joseph K. McKane
Attorney, Agent, or Firm—Jerry F. Janssen; Steven F. Weinstock

[57] ABSTRACT

Novel compounds which are selective dopamine agonists are useful for treating disorders characterized by abnormal dopamine levels, such as Parkinson's Disease, as well as cardiovascular disorders.

8 Claims, No Drawings

DOPAMINE AGONISTS

TECHNICAL FIELD

This invention relates to novel compounds which are selective dopamine agonists. These compounds are useful for treating disorders characterized by abnormal dopamine levels, such as Parkinson's Disease, as well as cardiovascular disorders.

BACKGROUND OF THE INVENTION

Dopamine receptors have been divided into two general categories, designated D-1 and D-2 receptors in the central nervous system (CNS). This division is made on the basis of pharmacological an biochemical differences between the two types of receptors. The D-1 receptor is linked to the enzyme adenylate cyclase so that stimulation of this receptor increases cyclic adenosine 3',5' monophosphate (cAMP) production. The D-2 receptor also regulates important functional activity within the CNS. The autoreceptors on dopaminergic neurons control the firing rate of these neuronal cells as well as the release of dopamine from the terminals of these neuronal cells. This autoreceptor has the pharmacological properties of a D-2 receptor. Likewise, the D-2 receptors on the cholinergic interneurons in the striatum regulate the release of acetylcholine from these cells. Finally, tonic stimulation of the D-2 receptors on the mammotrophs of the anterior pituitary suppresses prolactin secretion.

Dopamine occurs at high concentrations within the nerve terminals in the basal ganglia of the mammalian brain. In the early 1960's, the loss of striatal dopamine was established as a chemical sign of Parkinson's Disease. This deficiency is still thought to be primary to the etiology of the disease state.

L-DOPA (dihydroxyphenylalanine), when used in conjunction with a peripheral aromatic amino acid decarboxylase inhibitor, and often supplemented with anticholinergic agents, has been shown to be useful in the treatment of Parkinson's Disease. It is theorized that the therapeutic response to L-DOPA is a result of the conversion of L-DOPA into dopamine within the striatum, and thus the response is linked to stimulation of both the D-1 and D-2 receptors.

The success of L-DOPA therapy has led to the testing of other compounds capable of mimicking the post synaptic receptor actions of dopamine. Such direct acting agents might offer the therapeutic advantages of greater potency, increased duration of action, or fewer side effects over L-DOPA.

For example, bromocriptine, the direct acting dopamine agonist most widely used in the treatment of Parkinson's Disease, lowers the amount of L-DOPA required to achieve the maximal therapeutic response and allows for a delay in the onset of L DOPA therapy. However, the response to bromocriptine alone is not as great as that of L-DOPA.

Dopaminergic agents that show selectivity for different receptor subtypes are desirable in an effort to obtain the anticipated physiological response separate from other possibly less desirable effects.

Dopamine has been used in the treatment of shock, congestive heart failure, and renal failure. Stimulation of the peripheral DA-1 receptors causes vasodilation, particularly in the renal and mesenteric vascular beds where large numbers of these receptors are found. Dopamine's utility however has been limited by its ability to cause vasoconstriction at higher concentrations, presumably due to its secondary effects on adrenergic receptors, and by its emetic effects due to DA 2 stimulation. Agents selective for the peripheral DA-1 receptors may offer significant advantages over currently used treatments for these and other disorders.

SUMMARY OF THE INVENTION

The compounds of the invention are represented by the following structural formula:

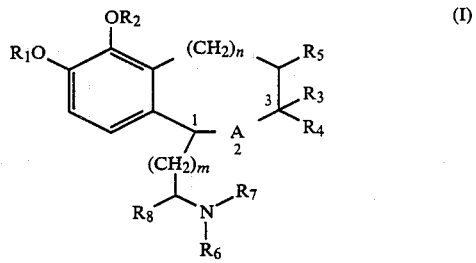

wherein
$A$ is O, C, CH, or $CH_2$;
$R_1$ and $R_2$ are independently hydrogen or a leaving group or a protecting group;
m and n are independently selected from zero or 1;
$R_3$ is H, alkyl, alkenyl, aryl, cycloalkyl, or taken together with $R_4$ can form a spirocycloalkyl, with the proviso that when n is zero $R_3$ is not H;
$R_4$ is H or alkyl, or taken together with $R_3$ can form a spirocycloalkyl;
$R_5$ is H or alkyl, or when n is zero, $R_5$ can be taken together with $R_3$ to form a fused cycloalkyl;
$R_6$ is H, alkyl, or taken together with $R_8$ can form an N containing heterocycle; $R_7$ is H, alkyl, alkenyl, cycloalkyl, arylalkyl, or taken together with A when A is C and when m=0 and n=0, can form a fused N containing heterocyclic ring, or taken together with $R_8$ can form an N containing heterocycle; or $R_6$ and $R_7$ together can form an N containing heterocycle with the proviso that when $R_6$ is alkyl $R_7$ cannot be arylalkyl;
$R_8$ is H, alkyl, taken together with $R_6$ or $R_7$ to form an N containing heterocycle, or taken together with the catechol ring can form a fused ring;
or pharmaceutically acceptable salts, esters or amides thereof.

It has been found that the compounds of the formula I and their physiologically acceptable acid addition salts have valuable pharmacological properties. In particular, they have effects on the central nervous system especially dopaminergic or antiparkinsonism effects.

DETAILED DESCRIPTION OF THE INVENTION

This invention related to novel compounds which are selective dopamine agonists. More particularly, this invention relates to compounds of the following formula:

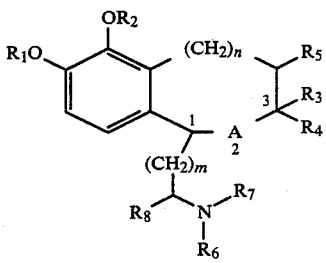

wherein

A is O, C, CH, or $CH_2$;

$R_1$ and $R_2$ are independently hydrogen or a leaving group or a protecting group;

m and n are independently selected from zero or 1;

$R_3$ is H, alkyl, alkenyl, aryl, cycloalkyl, or taken together with $R_4$ can form a spirocycloalkyl, with the proviso that when n is zero $R_3$ is not H;

$R_4$ is H or alkyl, or taken together with $R_3$ can form a spirocycloalkyl;

$R_5$ is H or alkyl, or when n is zero, $R_5$ can be taken together with $R_3$ to form a fused cycloalkyl;

$R_6$ is H, alkyl, or taken together with $R_8$ can form an N containing heterocycle; $R_7$ is H, alkyl, alkenyl, cycloalkyl, arylalkyl, or taken together with A when A is C and when m=0 and n=0, can form a fused N containing heterocycle, or taken together with $R_8$ can form an N containing heterocycle; or $R_6$ and $R_7$ together can form an N containing heterocycle with the proviso that when $R_6$ is alkyl $R_7$ cannot be arylalkyl;

$R_8$ is H, alkyl, taken together with $R_6$ or $R_7$ to form an N containing heterocycle, or taken together with the catechol ring can form a fused ring;

or pharmaceutically acceptable salts, esters or amides thereof.

The present invention also relates to compositions comprising a therapeutically effective amount of the compounds of Formula (I) and a pharmaceutically acceptable carrier or diluent.

The present invention also relates to the use of the compounds of Formula (I) in the treatment of dopamine related diseases.

Representative of the preferred compounds of Formula (I) include the following compounds, as well as their pharmaceutically acceptable salts, esters, and amides:

1-Aminomethyl -3,4-dihydro-5,6-dihydroxy-3-phenyl-naphthalene hydrobromide;

1-Aminomethyl-3,4-dihydro5,6-dihydroxy-3-phenyl-naphthalene hydrochloride;

1-Aminomethyl-5,6-bis(acetoxy)-3,4-dihydro-3-phenyl-naphthalene hydrochloride;

1-Aminomethyl-5,6-bis(trimethylacetoxy)-3,4-dihydro-3-phenyl naphthalene hydrochloride;

[1R,3S] 1-Aminomethyl-5,6-dihydroxy-3-phenyl-1,2,3,4-tetrahydro naphthalene hydrobromide;

1-Aminomethyl3-cyclohexyl-3,4-dihydro-5,6-dihydroxynaphthalene hydrobromide;

[1R,3S] 1-Aminomethyl-3cyclohexyl-5,6-dihydroxy-1,2,3,4-tetrahydro-naphthalene hydrobromide;

1R,3S] 1-Aminomethyl-3-t-butyl-3,4-dihydro-5,6-dihydroxy-1-H-2-benzopyran hydrochloride; [1R,3S] 1-Aminomethyl-3,4-dihydro-5,6-dihydroxy-3-phenyl-1H 2 benzopyran hydrochloride;

[1R,3S] 1-Aminomethyl-3-cyclohexyl-3,4-dihydro-5,6-dihydroxy-1H-2-benzopyran hydrochloride;

[1R,3R] 1-Aminomethyl-3,4-dihydro-5,6-dihydroxy-3-ethyl-1H-2-benzopyran hydrochloride;

Spiro[(1-aminomethyl-3,4-dihydro-5,6-dihydroxy-1H-2-benzopyran)-3,1'-cyclohexane] hydrochloride;

1R,3S] 1-Aminomethyl-3,4-dihydro-5,6-dihydroxy-3-(4'-methoxy)phenoxymethyl-1H-2-benzopyran hydrochloride;

[1R*,3S*] 1-Aminomethyl-3,4-dihydro-5,6-dihydroxy-3-phenyl-1H-2-benzopyran hydrochloride;

[1R,3S] 1-Aminomethyl-3,4-dihydro-5,6-dihydroxy-3-phenoxymethyl-1H-2-benzopyran hydrochloride;

[1R,3S] 1-Aminomethyl-3,4-dihydro-5,6-dihydroxy-3-(2'-phenyl)phenoxymethyl-1H-2-benzopyran hydrochloride;

[1R,3S] 1-Aminomethyl-3-(4'-t-butyl)phenoxymethyl-3,4-dihydro-5,6-dihydroxy-1H-2-benzopyran hydrochloride;

[1R,3S] 1-Aminomethyl-3-(4'-bromo)phenoxymethyl-3,4-dihydro-5,6-dihydroxy-1H-2-benzopyran hydrochloride;

1R,3S] 3-(1-Adamantyl)-1-aminomethyl-3,4-dihydro-5,6-dihydroxy-1-2-benzopyran hydrochloride;

1R,3R] 1-Aminomethyl-3-benzyl-3,4-dihydro-5,6-dihydroxy-1H-2-benzopyran hydrochloride;

1R,3R] 1-Aminomethyl-3,4-dihydro-5,6-dihydroxy-3-(2'-phenyl)ethyl-1H-2-benzopyran hydrochloride;

1R,3S] 1-Aminomethyl8-bromo3,4-dihydro-5,6-dihydroxy-3-phenyl-1H-2-benzopyran hydrochloride;

1R,3R] 1-Aminomethyl-3,4-dihydro-5,6-dihydroxy-3-n-octyl-1H-2-benzopyran hydrochloride;

1R,3R] 1-Aminomethyl-3,4-dihydro-5,6-dihydroxy-3-(1'hex 5'ene)-1H-2-benzopyran hydrochloride;

[1R,3S] 1-Aminomethyl-3,4-dihydro 5,6 dihydroxy-3-ethyl-1H 2-benzopyran hydrochloride;

[1R,3R] 1-Aminomethyl-3,4-dihydro-5,6-dihydroxy-3-n-hexyl-1H-2-benzopyran hydrochloride;

[1R,3S] 1-Aminomethyl-3-(4'-bromo)phenyl-3,4-dihydro-5,6 -dihydroxy-1H-2-benzopyran hydrochloride;

[1R,3S] 1-Aminomethyl-3,4-dihydro-5,6-dihydroxy-3-(3'-hydroxy)phenyl-1H-2-benzopyran hydrochloride;

[1R,3S] 3-Cyclohexyl-3,4-dihydro-5,6-dihydroxy-1-(N-methyl)-aminomethyl-1H-2-benzopyran hydrochloride;

[1R,3S] 3-t-Butyl-3,4-dihydro-5,6-dihydroxy-1-(N-methyl)-aminomethyl-1H-2-benzopyran hydrochloride;

[1R,3S] 1-(N-Allyl)-aminomethyl-3-cyclohexyl-3,4-dihydro-5,6-dihydroxy-1H-2-benzopyran hydrochloride;

[1R,3S] 3-Cyclohexyl-1-(N-cyclopropyl)-aminomethyl-3,4-dihydro-5,6-dihydroxy-1H-2-benzopyran hydrochloride; [1R,3S] 1-(N-Benzyl)-aminomethyl-3-cyclohexyl-3,4-dihydro-5,6-dihydroxy-1H 2-benzopyran hydrochloride;

[1R,3S] 1,3-Bis(aminomethyl)-3,4-dihydro-5,6-dihydroxy-1H-2-benzopyran dihydrochloride;

[1R,3S] 1-Aminomethyl-3,4-dihydro-5,6-dihydroxy-3-hydroxymethyl-1H-2-benzopyran hydrochloride;

[1R,3S] 1-Aminomethyl-3-cyclohexyl-6,7-dihydroxy-1,3,4,5-tetrahydro-2-benzoxepin hydrochloride;

[1R,3S] 1-Aminomethyl-3,4-dihydro-5,6-dihydroxy-3-(N-piperidino)methyl-1H-2-benzopyran dihydrochloride;

[1R,3S]-5,6 -Dihydroxy-3-phenyl-1-(2'R-pyrrolidino)-1,2,3,4-tetrahydro-naphthalene hydrobromide;

[1R,3R]5,6-Dihydroxy-3-phenyl-1-(2'R-pyrrolidino)-1,2,3,4-tetrahydro-naphthalene hydrobromide;
3,4-Dihydro-5,6-dihydroxy-1-(N-methyl)-aminomethyl-3-phenyl-naphthalene hydrochloride;
[1R,3S] 5,6-Dihydroxy-1-(N-methyl)-aminomethyl-3-phenyl-1,2,3,4-tetrahydro-naphthalene hydrochloride;
[1R,8S,9aR]-1-Amino-5,6-dihydroxy-2,3,7,8,9,9a-hexahydro-8-phenyl-phenalene hydrobromide;
[1S,8S,9aR]-1-Amino-5,6-dihydroxy2,3,7,8,9,9a-hexahydro-8-phenyl-phenalene hydrobromide;
6,7-Dihydroxy-4-phenyl-2,3,4,5-tetrahydro-1-H-benz[e]isoindole formic acid salt;
1-Aminomethyl-3,4-dihydro-5,6-dihydroxy-3-(3'-hydroxy)phenyl-naphthalene hydrobromide;
1-Aminomethyl-3,4-dihydro-5,6-dihydroxy-3-(4'-hydroxy)phenyl-naphthalene hydrobromide; and
[1R,3S] 1-Aminomethyl-5,6-dihydroxy-3-(3'-hydroxy)-phenyl-1,2,3,4-tetrahydro naphthalene hydrobromide;

Contemplated equivalents of the compounds of general Formula (I) are compounds otherwise corresponding thereto and having the same general properties wherein one or more of $R_1$, $R_2$, $R_3$, etc. are simple variations of the substituents as defined herein. As will be apparent, where a substituent can be a hydrogen atom, the exact chemical nature of a substituent which is other than hydrogen at that position is not critical, so long as it does not adversely affect the efficacy of the compound.

The term "alkyl" is used herein to mean straight or branched chain radicals of one to twelve carbon atoms. Representative of such radicals are methyl, ethyl, n-propyl, isopropyl, n-butyl, sec-butyl, isobutyl, tert-butyl, 2-ethylhexyl, n-octyl, 2,4-dimethylpentyl, and the like. These can be unsubstituted, or they can be substituted, for example, with loweralkyl, cycloalkyl, or aryl groups, or with heteroatoms such as N or O, or with heterocyclic groups such as pyrrolidino, piperidino and morpholino, provided that any such substituents not interfere with the efficacy of the compound. The heteroatoms can be further substituted as illustrated by Examples 16, 18, 19, 20 and 21.

The term "cycloalkyl" as used herein refers to a three to twelve carbon cyclic group, such as those compounds found in Examples 12, 14, and 15. The cycloalkyl compounds can be unsubstituted, or they can be substituted (for example, with alkyl, cycloalkyl, or aryl groups, N, O, or halo) or they can be fused to other cycloalkyl, heterocyclic or aryl groups, provided that any such substituents not interfere with the efficacy of the compound.

The term "fused" as used herein refers to two cyclic groups having two atoms in common to both rings.

The term "spirocycloalkyl" is used herein to mean two rings fused such that a single carbon is common to both rings, for example, the compound of Example 14, Table 1.

The term "alkenyl" is used herein to mean straight or branched chain radicals of one to twelve carbon atoms containing at least one double bond. Representative of such radicals are ethenyl, n propenyl, isopropenyl, n-butenyl, isobutenyl, 2-ethylhexenyl, 2,4-dimethylpentenyl, and the like. These can be unsubstituted, or they can be substituted, for example, with loweralkyl, cycloalkyl, or aryl groups, or with heteroatoms or with heterocyclic groups, provided that any such substituents not interfere with the efficacy of the compound.

The term "aryl" is used herein to mean aromatic radicals having five to six atoms in a single ring system which may contain one to three hetero atoms selected from S, O, and N, the remaining atoms being carbon atoms. Representative aromatic radicals include phenyl, pyridyl, pyrazinyl, thiazoyl, furyl, and thienyl. Further, the single ring system may be substituted to form a multiple fused ring system, for example, 1-naphthyl, 2-naphthyl and the like. These compounds can be unsubstituted, or they can be substituted provided that any such substituents not interfere with the efficacy of the compound.

The term "arylalkyl" is used herein to mean straight or branched chain radicals of one to twelve carbon atoms which is substituted with an aryl group, such as benzyl or phenylethyl.

The term "heterocycle" as used herein refers to a 3 to 12 atom cyclic group containing one or more heteroatoms such as N, O or S.

The term "halo" is used herein to mean Cl, Br, F, and I.

The term "catechol ring" is used herein to mean a ortho dihydroxybenzene which can be further substituted, for example, with H, alkyl, halo, and the like.

The term "catechol substituents" is used herein to mean substituents on the catechol hydroxyl of the catechol ring which can be protecting groups or leaving groups.

The term "leaving groups" is used herein to mean substituents which are easily cleaved in vivo to form the corresponding catechol, such as acyl, cyclic borate esters, and the like as described hereinbelow.

The term "protecting groups" is used to mean substituents which protect the catechol oxygens, for example, from being oxidized to the orthoquinone. Examples of such protecting groups are alkyl, alkenyl, and cycloalkyl such as cyclopropylmethyl, cyclohexyl, and aryl, or cyclohexylidenyl as described hereinbelow.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of dopamine deficiency. The salts can be prepared in situ during the final isolation and purification of the compounds of Formula (I), or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, lauryl sulphate salts and the like. Representative alkali or alkaline earth metal salts include the sodium, calcium, potassium and magnesium salts, and the like.

Certain compounds of the invention exist in optically active forms. The pure d isomers, pure l isomers, as well as mixtures thereof, and the racemic mixtures are contemplated by the invention. Additional asymmetric carbon atoms may be present in a substituent such as an alkyl group. All such isomers as well as mixtures thereof are intended to be included in the invention. In particular, stereochemistry of the substituents at the 1 and 3 positions, as shown in Formula (I), can be either axial or equatorial unless specifically noted otherwise.

Normal dopamine levels are those levels of dopamine that are found in the brains of control subjects and are usually measured as dopamine metabolite levels. Abnormal dopamine levels are those levels of dopamine that are not within the range of dopamine levels found in the brains of control subjects.

The compounds of the present invention can be administered to humans and animals either orally, rectally, parenterally, by inhalation spray, or transdermally in dosage unit formulations containing conventional non toxic pharmaceutically acceptable carriers, adjuvants and vehicles as desired. The compounds of the present invention may be administered alone or in combination or in concurrent therapy with other agents which effect the dopaminergic system such as L-dopa, amantadine, apomorphine or bromocriptine; and with cholinergic agents, for example, benztropine, biperiden, ethopropazine, procyclidine, trihexylphenidyl and the like.

The term "parenteral" as used herein includes subcutaneous, intravenous, intramuscular, and intraarticular injection and infusion techniques.

The term "administration" of the dopamine agonist or composition herein includes systemic use, as by intramuscular, intravenous, intraperitoneal or subcutaneous injection and continuous intravenous infusion, and oral administration thereof, as well as transdermal applications of the compounds and compositions.

This invention also provides pharmaceutical compositions in unit dosage form, comprising a therapeutically effective amount of a compound of this invention in combination with a conventional pharmaceutical carrier.

By "a therapeutically effective amount" of the dopamine against herein is meant a sufficient amount of the compound to treat or prevent a disorder characterized by dopamine deficiency at a reasonable benefit/risk ratio applicable to any medical treatment. Of course, the total daily usage of the compositions herein will be decided by the attending physician within the scope of sound medical judgment. The effective amount of the dopamine agonist of this invention will vary with the particular disorder being treated, the severity of the disorder, the duration of the treatment, the specific compound, ester, salt, or amide employed, the age and weight of the patient and like factors well known in the medical arts.

This invention also includes pharmaceutical compositions in unit dosage form, comprising a therapeutically effective amount of a compound of this invention in combination with a conventional pharmaceutical carrier.

Total daily dose of the compounds of this invention administered to a host in single or divided doses can be in amounts, for example, from 0.01 to 500 mg/kg body weight daily and more usually 0.1 to 60 mg/kg body weight daily. Single dose compositions can contain such amounts or submultiples thereof to make up the daily dose. In general, treatment and prevention regimens according to the present invention comprise administration to a patient in need of such treatment from about 100 mg to about 2000 mg. of the compound of this invention per day in multiple doses or, preferably, in a single dose of from 250 mg to about 1000 mg.

It will be understood, however, that the specific therapeutically effective dose level for any particular patient will depend upon a variety of factors including the activity of the specific compound employed; the age, body weight, general health, sex and diet of the patient; the time of administration, route of administration and rate of excretion of the specific compound employed; drugs used in combination with the specific compound employed; and the severity of the particular disease undergoing therapy.

The present invention includes one or more of the compounds of Formula (I) formulated into compositions together with one or more non toxic pharmaceutically acceptable carriers, adjuvants, or vehicles (which are collectively referred to herein as carriers) for parenteral injection, transdermal, oral administration in solid or liquid form, rectal administration, and the like.

Non toxic, inert pharmaceutically suitable carriers include solid, semi solid or liquid diluents, fillers and formulation auxiliaries of all types.

As used herein, the term "pharmaceutically acceptable carriers" means a solid or liquid filler, diluent or encapsulating material. Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of active ingredient that can be combined with the carrier materials to produce a single dosage form will vary depending upon the host treated and the particular mode of administration.

Injectable preparations such as sterile injectable aqueous or oleagenous suspensions can be formulated according to the known art using suitable dispersing or wetting agents and suspending agents. The sterile injectable preparation can also be a sterile injectable solution or suspension in a non toxic parenterally acceptable diluent or solvent, for example, as a solution in 1,3-butanediol. Among the acceptable vehicles and solvents that can be employed are water, Ringer's injection, U.S.P. and isotonic sodium chloride solution. In addition, sterile, fixed oils are conventionally employed as a solvent or suspending medium. For this purpose any bland fixed oil can be employed including synthetic and semisynthetic mono-, di- or triglycerides. In addition, fatty acids such as oleic acid find use in the preparation of injectables.

Suppositories for rectal administration can be prepared by mixing the drug with a suitable non-irritating excipient such as cocoa butter or a polyethylene glycol which is solid at ordinary temperatures but liquid at the rectal temperature and will therefore melt in the rectum and release the drug.

Solid dosage forms for oral administration can include capsules, tablets, pills, powders, prills and granules. In such solid dosage forms, the active compound can be admixed with at least one inert diluent such as sucrose, lactose or starch. Such dosage forms can also comprise, as is normal practice, additional substances other than inert diluents, e.g., tableting lubricants and other tableting aids such as magnesium stearate and microcrystalline cellulose. In the case of capsules, tablets and pills, the dosage forms can also comprise buffering agents. Tablets and pills can additionally be prepared with enteric and other release-controlling coatings.

Liquid dosage forms for oral administration can include pharmaceutically acceptable emulsions, microemulsions, solutions, suspensions, syrups and elixirs containing inert diluents commonly used in the art, such as water. Such compositions can also comprise adjuvants, such as wetting agents, emulsifying and suspending agents, and sweetening, flavoring and perfuming agents.

If desired, the compounds of the present invention can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

The active compounds can also be in micro-encapsulated form with one or more excipients as noted above.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants, such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or dispersing the compound in a polymer matrix or gel.

In general, the compounds of this invention are synthesized by reaction schemes I through V as illustrated below. It should be understood that $R_1$, $R_2$, and $R_3$ as used herein correspond to the R groups identified by Formula (I). The oxygens of the catechol groups can be derivatized with "protecting groups" or "leaving groups" which are known in the art and can be prepared by conventional methods. These derivatizing groups can be selected from among phenol derivatives and derivatives which are suitable to catechols because of the proximity of the two hydroxyl functions. Commonly used phenol derivatives are ethers, for example alkyl, alkenyl, and cycloalkyl ethers (such as methyl, isopropyl, t-butyl, cyclopropylmethyl, cyclohexyl, allyl ethers and the like); alkoxyalkyl ethers such as methoxymethyl or methoxyethoxymethyl ether and the like; alkylthioalkyl ethers such as methylthiomethyl ether; tetrahydropyranyl ethers, arylalkyl ethers (such as benzyl, o-nitrobenzyl, 9 anthrylmethyl, 4-picolyl ethers and the like); trialkylsilyl ethers such as trimethylsilyl, triethylsilyl, t-butyldimethylsilyl ethers and the like; alkyl esters such as acetates, propionates, n-butyrates, isobutyrates, trimethylacetates, benzoates and the like; substituted alkyl esters such as 3-(methoxycarbonyl)propionate, 3-aminopropionate, 3-(t-butoxycarbonyl)propionate and the like; carbonates such as methyl, ethyl, 2,2,2-trichloroethyl, vinyl, benzyl and the like, carbamates such as methyl, isobutyl, phenyl, benzyl, dimethyl, and the like; and sulfonates such as methanesulfonate, trifluoromethanesulfonate, toluenesulfonate and the like. Commonly used catechol derivatives include cyclic acetals and ketals such as methylene acetal, acetonide derivatives, cyclohexylidene ketal, diphenylmethylene ketal and the like; cyclic esters such as cyclic borate esters, cyclic carbonate esters and the like.

SCHEME IA

The compounds of Formula IA and IB are synthesized by the method discussed herein. 2,3-Dihydroxybenzaldehyde (which has the two catechol hydroxy groups protected by, for example, alkyl groups preferably methyl groups) and a substituted acetic acid derivative, such as phenyl acetic acid, are condensed in the presence of a dehydrating agent, such as acetic anhydride, and a proton acceptor such as triethylamine (TEA) to give compound 2. The carboxylic acid (or acid derivative such as the methyl or ethyl ester) and the double bond of compound 2 are reduced by a reducing agent such as lithium aluminum hydride (LAH) preferably in an ether solvent such as tetrahydrofuran (THF). The leaving group ability of the hydroxyl group of compound 3 is enhanced by derivatizing it with, for example, methanesulfonyl chloride, in the presence of a proton acceptor such as TEA, and it is then converted to the cyano compound 4 by nucleophilic displacement with a salt of cyanic acid such as sodium cyanide in a polar solvent such as dimethyl sulfoxide (DMSO). The cyano group is hydrolyzed to the corresponding carboxylic acid group under basic conditions using, for example, aqueous sodium hydroxide, and the naphthalenone derivative (compound 5) is prepared by intramolecular acylation of the protected catechol ring using a dehydrating agent such as polyphosphoric acid or methanesulfonic acid/trifluoroacetic acid (TFA). Compound 5 is converted to the corresponding cyanohydrin by treatment with a cyano derivative such as trimethylsilyl cyanide and the cyano alcohol is reduced to the amine (compound 6) by treatment with a reducing agent such as LAH, preferably in a ether solvent such as diethyl ether. The 1-hydroxyl group is eliminated from compound 6 by heating it under acidic conditions, e.g. in isopropyl alcohol saturated with hydrochloric acid, to produce the dihydronaphthalene derivative (compound 7). Compound IA is produced when the catechol hydroxyl groups of compound 7 are deprotected with, for example, boron tribromide or boron trichloride in an inert solvent such as 1,2-dichloroethane or methylene chloride. Compound 7 is also hydrogenated to the corresponding tetrahydronaphthalene derivative in the presence of a catalyst such as palladium or platinum on carbon and then deprotected with e.g. boron tribromide or boron trichloride to produce IB. In the preferred embodiments of compounds IA and IB, $R_3$ is phenyl or cyclohexyl and X is bromide or chloride.

SCHEME IB

The compounds of Formula I are alternately synthesized by the method discussed herein. 2,3 Dihydroxybenzaldehyde, with the catechol protected as described in Scheme IA and the aldehyde group derivatized as its dithiane, is treated with a base such as n-butyl lithium, to generate the anion (compound 8), and condensed with an alpha-beta unsaturated acid derivative such as ethyl cinnamate in the presence of dimethyl-2-imidazolidinone to produce compound 9. The dithiane group is removed from compound 9 by treatment with hydrogen in the presence of a catalyst such as Raney nickel and converted to compound 5 as described in Scheme IA. Compound 5 is further converted to IA and IB as described in Scheme IA.

SCHEME II

The compounds of Formula IIA, IIB and IIC are synthesized by the method discussed herein. A catechol (compound 10 wherein $R_1$ and $R_2$ are independently selected from alkyl groups such as methyl or $R_1$ and $R_2$ together form a spiro cycloalkyl group such as cyclohexyl) is reacted in the presence of a base, such as n-butyl lithium, with an epoxide such as compound 11 (wherein $R_4$ and $R_5$ are hydrogen and $R_3$ is preferably selected from cyclohexyl, phenyl, ethyl, p-methoxyphenoxymethyl, phenoxymethyl, o-phenylphenoxymethyl, p-t-butylphenoxymethyl, p-bromophenoxymethyl, adamantyl, benzyl, phenylethyl, n-octyl, n-hexyl, n-decyl, 1-hex-5-enyl, t-butyl or benzyloxymethyl; or $R_5$ is hydrogen and $R_3$ and $R_4$ together form a spiro cycloalkyl group such as cyclohexyl; or $R_4$ is hydrogen and $R_3$ and $R_5$ together form a cycloalkyl group fused to the epoxide ring, such as cyclohexyl) to produce compound 12.

Compound 12 can be oxidized to the corresponding ketone with an oxidizing agent such as pyridinium chlorochromate (PCC) which can be stereoselectively reduced with, for example, B-chlorodiisopinocampheylborane (as described in Example 46) to give the optically active isomers of compound 12.

Compound 12 is condensed with a bromo aldehyde derivative such as bromoacetaldehyde dimethyl acetal or 3-bromo- propionaldehyde dimethyl acetal to form the substituted benzopyran derivative 14. Compound 14 is converted to compound 15 by treatment with a nucleophilic azide such as lithium azide in a polar solvent such as dimethyl formamide, followed by reduction of the azido compound, for example with LAH. Compound 15 is converted to IIA by generation of the amine salt in acidic solution and deprotection of the catechol hydroxyl groups in acid solution. Compound 15 is converted to compound IIB by treatment with ethyl formate followed by reduction with, for example, LAH and generation of the amine salt with deprotection of the catechol hydroxyl groups in acidic solution. Compound 14 is converted to IIC by treatment with an amine such as allyl amine, cyclopropylamine, benzylamine, phenylethylamine or pyrrolidine, followed by the deprotection of the catechol hydroxyl groups and generation of the amine salt in acidic solution. In the case wherein the epoxide 11 is substituted with a benzyloxymethyl group (i.e. $R_3$=benzyloxymethyl), $R_3$ is further elaborated as shown in Scheme III.

SCHEME III

The compounds of Formula IIIA, IIIB and IIIC are synthesized by the method discussed herein. Compound 16 is prepared from compound 14 (wherein $R_3$=benzyloxymethyl) by hydrogenolysis and nucleophilic displacement of the bromine atom by an azido group. $R_1$ and $R_2$ are defined in Scheme II. Compound 16 is converted to IIIA by the following sequence of reactions: activation of the hydroxymethyl group by reaction, for example, with methanesulfonyl chloride and displacement with a nucleophilic azide, such as lithium azide, to give the azidomethyl compound 17, followed by reduction of the two azido groups, for example, with LAH and deprotection of the catechol hydroxyls with an acid such as hydrochloric acid in alcohol solution. Compound 16 is converted to IIIB by treatment with a reducing agent such as LAH and deprotection of the catechol hydroxyls in acidic solution. Compound 16 is converted to IIIC by activation of the 3 hydroxymethyl group, for example by reaction with methanesulfonyl chloride, followed by displacement with a nucleophilic amine, $NHR_9R_{10}$, in which $R_9$ and $R_{10}$ are independently selected from H and lower alkyl or $R_9$ and $R_{10}$ together form a ring containing a nitrogen atom such as pyrrolidino or piperidino or morpholino, followed by reduction of the azido group and deprotection of the catechol hydroxyls in acidic solution.

SCHEME IV

The compounds of Formula IVA and IVB are synthesized by the method discussed herein. $R_1$, $R_2$, and $R_3$ are defined in Scheme I. Compound 5 is converted to the cyanohydrin by treatment with a nucleophilic cyano derivative such as trimethylsilyl cyanide in the presence of a catalyst such as aluminum trichloride. The cyanohydrin is dehydrated to the alpha, beta unsaturated nitrile by treatment with a dehydrating agent such as TFA/p-toluenesulfonic acid and the unsaturated nitrile reduced to the saturated nitrile (compound 19) by treatment with a reducing agent such as sodium borohydride. The nitrile group is hydrolyzed to a carboxylic acid group (compound 20) and the acid converted to the N-methoxy-N-methyl amide 21 by sequential treatment with a chlorinating agent, such as oxalyl chloride, to generate the acid chloride, and N methoxymethylamine. Compound 21 is converted to a mixture of the diastereomeric pyrrolidino derivatives 22 and 23 by treatment with 2,2,5,5, tetramethyl 1-aza-2,5-disilacyclopentane-1-propyl magnesium bromide followed by reduction with a reducing agent such as sodium borohydride, and the diastereomers are separated chromatographically. The separated isomers 22 and 23 are converted to IVA and IVB, respectively, by treatment with boron trihalide, preferably boron tribromide.

SCHEME V

The compounds of Formula VA and VB are synthesized by the method discussed herein. $R_1$, $R_2$, and $R_3$ are defined in Scheme I. Compound 5 is converted to compound 24 by treatment with dimethyl succinate in the presence of a base such as potassium t-butoxide. Compound 24 is reduced to the corresponding 1,2,3,4-tetrahydronaphthalene and the tricyclic ring system is formed by treating the 1,2,3,4 tetrahydronapathlene derivative, compound 24, with a dehydrating agent such as polyphosphoric acid. Four isomeric products were obtained. Two of the isomers, compounds 25 and 26, were carried on to VA and VB, respectively. Reduction of the 3 keto group of compounds 25 and 26 with, for example hydrogen in the presence of a catalyst such as palladium on carbon support was followed by hydrolysis of the ester in basic solution to give compounds 27 and 28, respectively. Compounds 27 and 28 were each treated with diphenylphosphoryl azide and benzyl alcohol in the presence of a base such as triethylamine to give the carbobenzyloxy protected amino derivatives, which were deprotected by hydrogenolysis using, for example, palladium on carbon support as a catalyst, and demethylation using, for example, boron tribromide to give VA and VB.

Scheme VI

The compounds of Formula VI are synthesized by the method described herein. $R_1$, $R_2$, and $R_3$ are defined in Scheme I. Compound 5 is converted to the alpha-bromoketone by treatment with a brominating agent such as phenyltrimethylammonium tribromide. The bromide undergoes nucleophilic displacement, for example, with the anion of thiophenol to give the alpha thiophenylketone, compound 29. The ketone is reduced to the alcohol with a reducing agent such as sodium borohydride, and the hydroxyl group is eliminated with a dehydrating agent such as p-toluenesulfonic acid to give the thio-enolether. The sulfur atom of the thio enolether is oxidized to the sulfoxide with an oxidizing agent such as mCPBA to give compound 30. The amine component is made by a nucleophilic displacement on chloromethyltrimethylsilane by an amine (compound 31), such as benzylamine (compound 31, wherein R =benzyl). The imine is formed by treatment of the amine with an aldehyde, such as formaldehyde, and then an alcohol, such as methanol, is added to form the alkoxymethyl amine compound 33. Compound 33 is then reacted with the sulfoxide (compound 30) in the presence of an acid, such as TFA to generate the azomethine ylid in situ which traps the activated double bond of the alpha, beta unsaturated sulfoxide to give a 1,3-dipolar addition adduct which, on heating, spontaneously undergoes elimination to give the cyclization/elimination product, compound 34. The nitrogen can be deprotected by treatment with an acylating agent, such as 1 chloroethylchloroformate followed by acyl group removal with a nucleophile, such as methanol to give compound 35. The catechol is deprotected by treatment with a boron trihalide, preferably boron tribromide to give VI.

The foregoing may be better understood by reference to the following examples which are provided for the illustration and not the limitation of the invention.

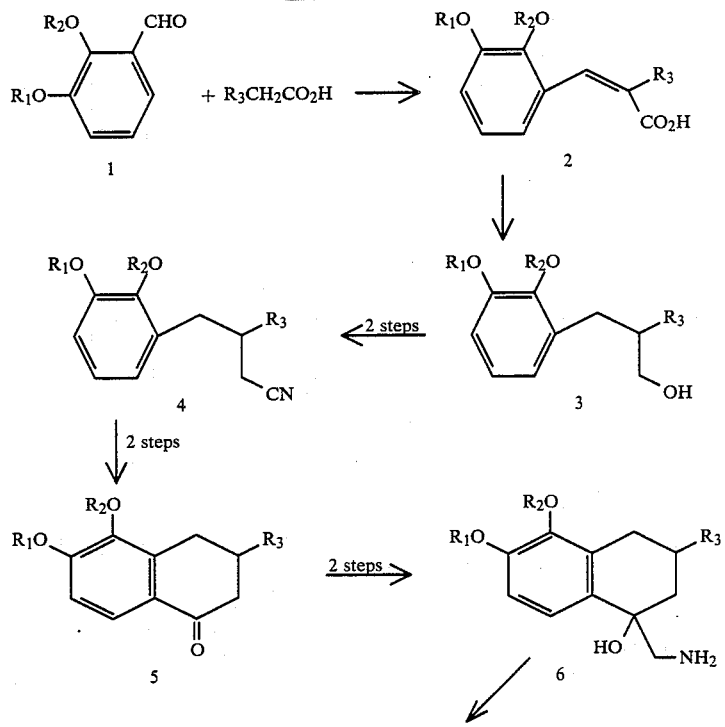

SCHEME IA

-continued
SCHEME IA
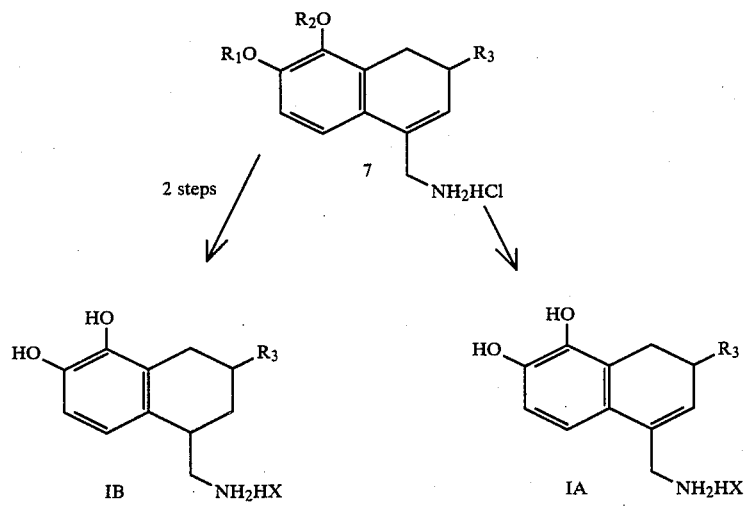
SCHEME IB
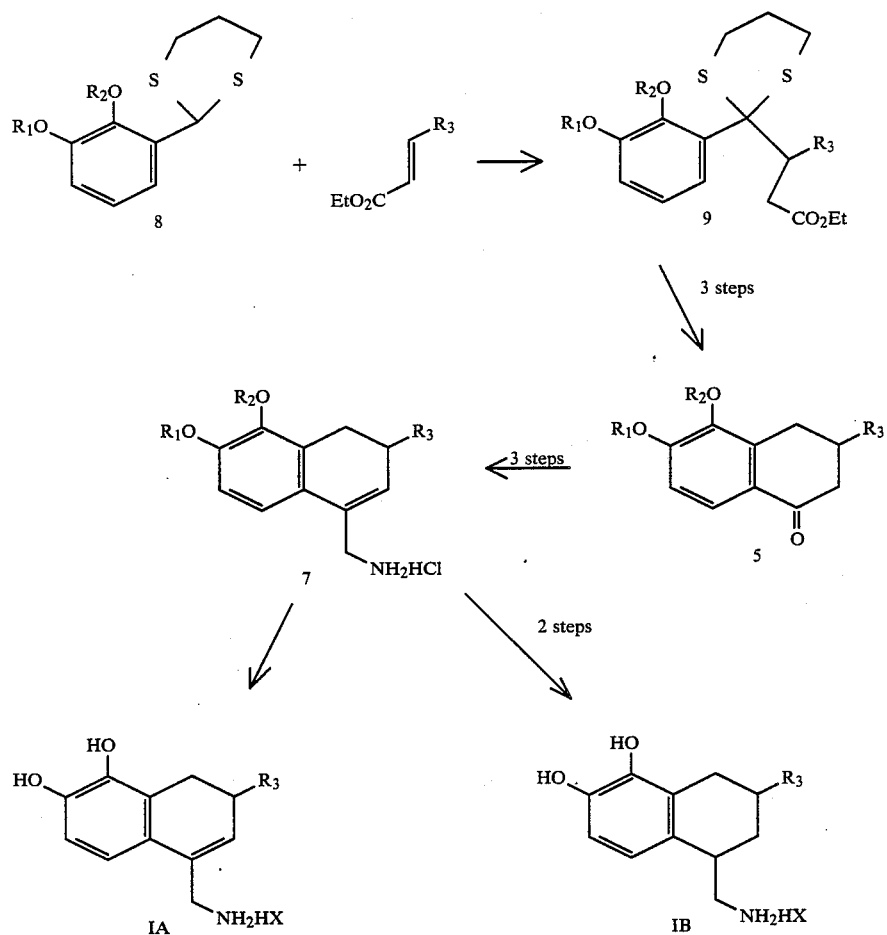

SCHEME II
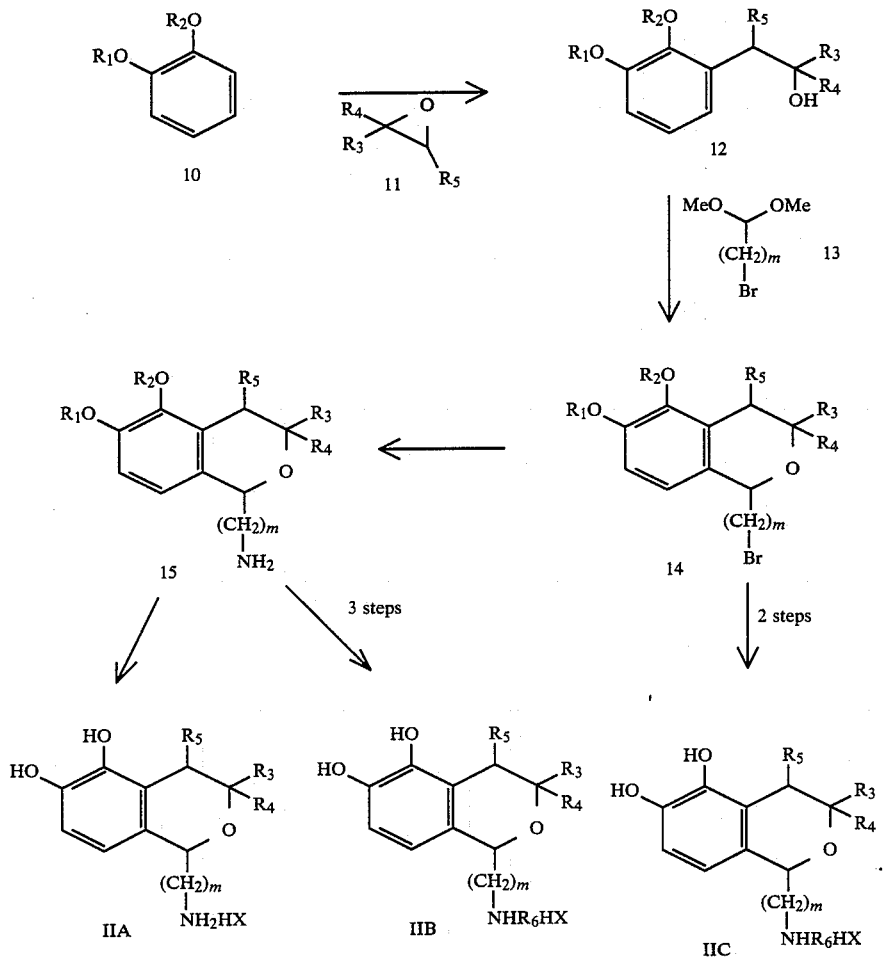
SCHEME III
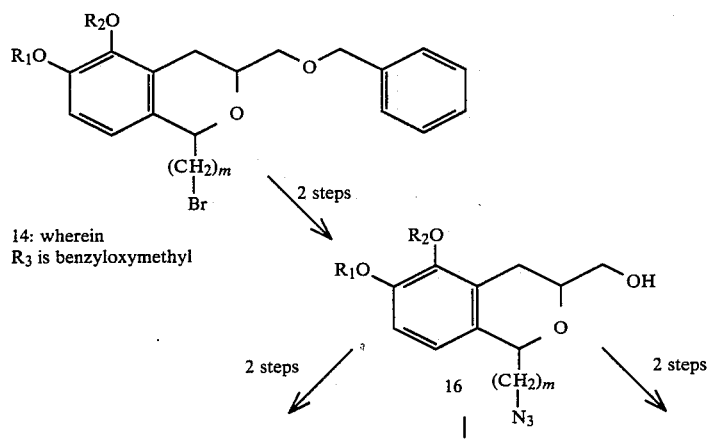
14: wherein R3 is benzyloxymethyl

-continued
SCHEME III
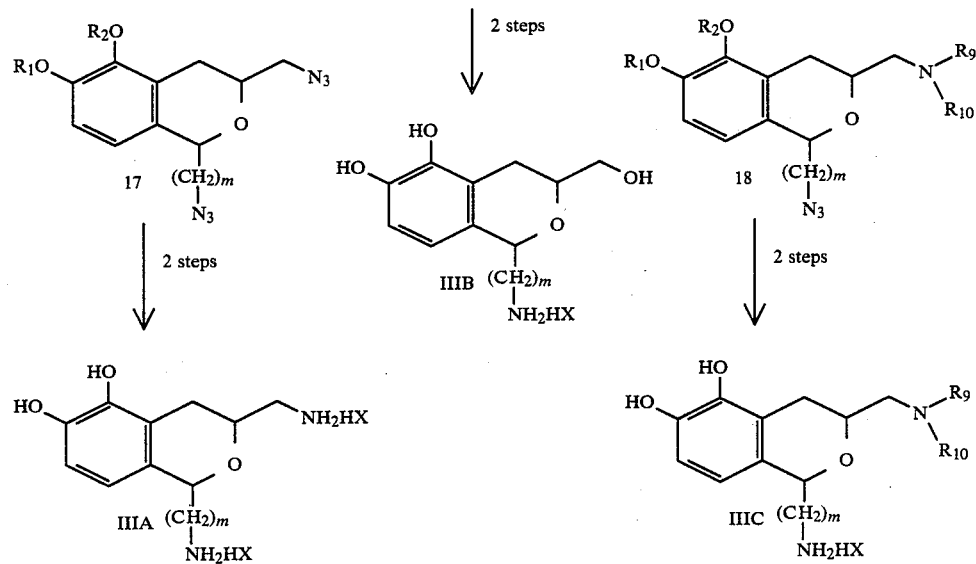
SCHEME IV
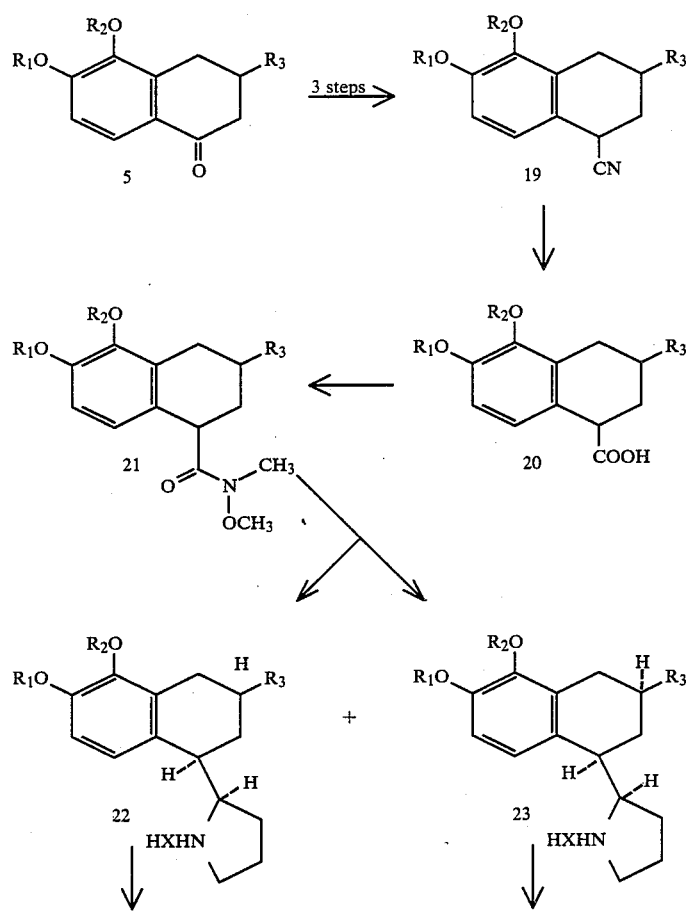

SCHEME IV
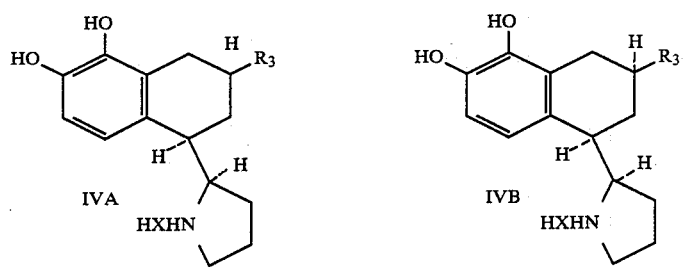
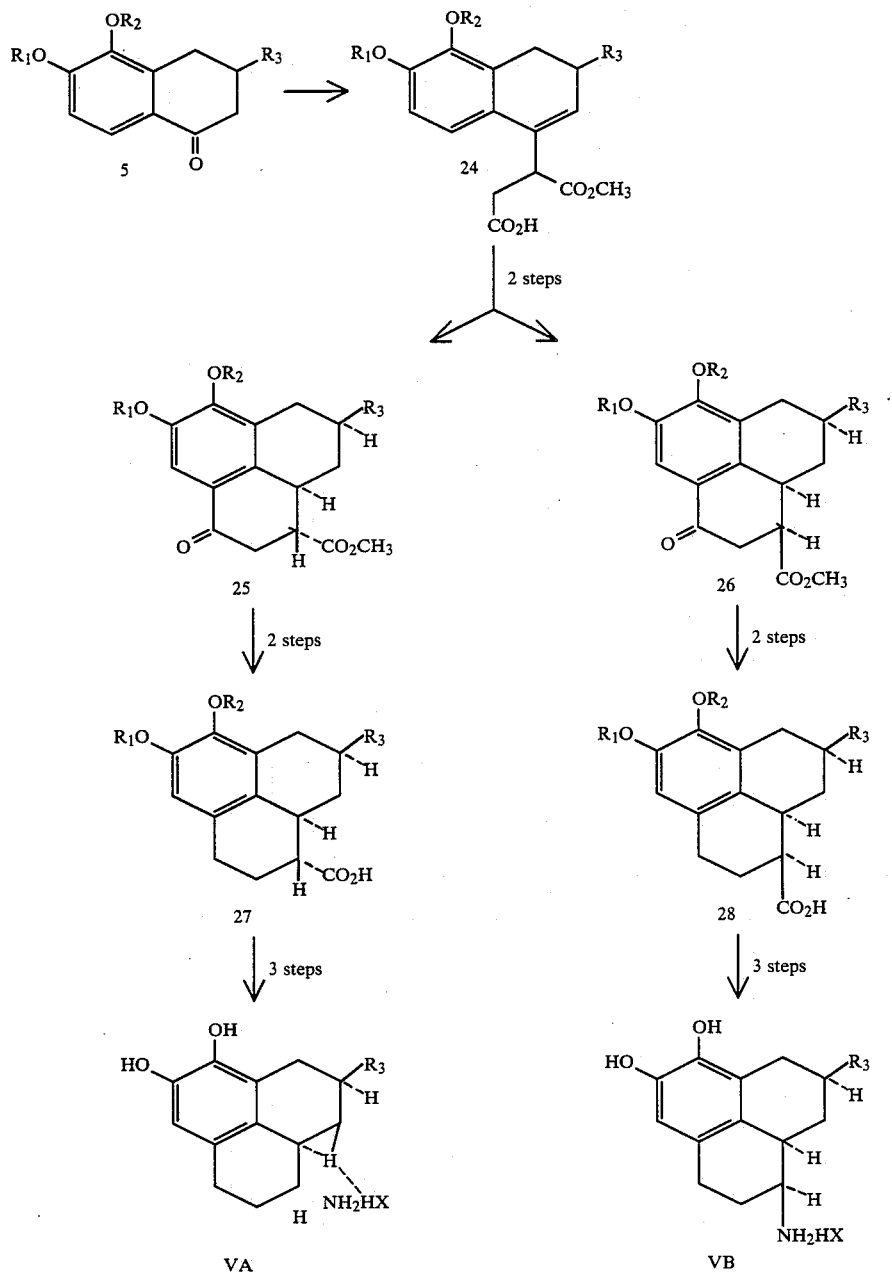
SCHEME V

SCHEME VI

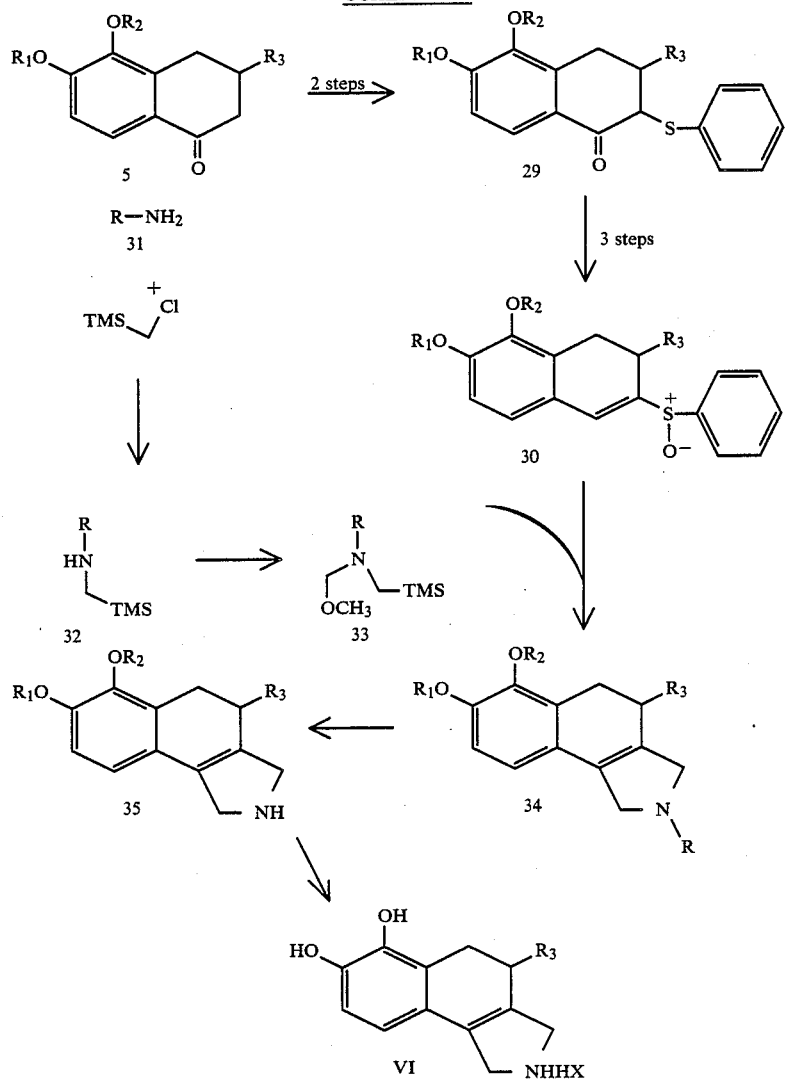

Example 1

5,6-Dimethoxy-3-phenyl-1,2,3,4-tetrahydro-1-naphthalenone

Method A

Step 1:(E,Z)-3-(2',3'-Dimethoxyphenyl)-2-phenylpropenoic acid

A solution of 202 g (1.21 mol) of 2,3-dimethoxybenzaldehyde (commercially available from Aldrich Chemical Company), 200 g (1.21 mol) of phenyl acetic acid (commercially available from Aldrich Chemical Company), 600 mL of acetic anhydride and 204 mL (1.46 mol) of triethylamine (TEA) was heated at reflux temperature for 24 h. The reaction mixture was allowed to cool to ambient temperature and 1 L of water was added, followed by the addition of 2 L of ethyl acetate and another 4 L of water. The layers were separated and the organic layer was extracted with saturated aqueous sodium bicarbonate solution. The organic layer was discarded. The aqueous layer was acidified with concentrated hydrochloric acid and extracted with 4 L of ethyl acetate. The ethyl acetate solution was dried over anhydrous magnesium sulfate and concentrated in vacuo to give 250 g (72% yield) of (E,Z)-3-(2',3'-dimethoxyphenyl)-2-phenylpropenoic acid as a 30/70 mixture of the E and Z isomers, m.p. 115–160° C. DCI MS: 302 (M+NH4)+, 285 (M+H)+.

Step 2: 3-(2',3'-Dimethoxyphenyl)-2-phenylpropanol

A solution of 15 g (395 mmol) of lithium aluminum hydride (LAH) in 500 mL of tetrahydrofuran (THF) was cooled to 0° C. (E,Z)-3-(2',3'-Dimethoxyphenyl)-2-phenylpropenoic acid (50 g, 176 mmol), from step 1, was dissolved in 100 mL of THF and the resultant solution was added to the LAH solution dropwise over a 30 min period. The reaction mixture was then heated at reflux temperature for 2 h. After cooling the reaction mixture to 0° C., the reaction was quenched by the careful sequential addition of 15 mL of water, 15 mL of 15% aqueous sodium hydroxide solution and 45 mL of water. The resultant precipitate was filtered and the filtrate concentrated in vacuo to give 46.6 g (97% yield) of 3-(2',3'-dimethoxyphenyl)-2-phenylpropanol as an oil. $^1$H NMR (CDCl$_3$) delta 1.8–1.9 (m, 1H), 2.1–2.2 (m, 1H), 2.7–2.95 (m, 1H), 3.0–3.15 (m, 2H), 3.7–3.8 (m, 1H), 3.8 (s, 3H), 3.83 (s, 3H), 6.63 (d, 1H), 6.75 (d, 1H), 6.9 (t, 1H), 7.15–7.4 (m, 5H).

Step 3: 3-(2′,3′-Dimethoxyphenyl)-2-phenylpropane 1-methanesulfonate 3-(2′,3′-Dimethoxyphenyl)-2-phenylpropanol (41.5 g, 152 mmol), from step 2, and 30.5 g (301 mmol) of TEA were dissolved in 300 mL of THF. Methanesulfonyl chloride (34.5 g, 301 mmol) was added slowly to this solution at 0° C. The reaction mixture was allowed to warm to ambient temperature. After stirring the reaction mixture for 1 h at ambient temperature, it was diluted with 300 mL of diethyl ether, washed with water, dried over anhydrous magnesium sulfate and concentrated to give 40.8 g (76% yield) of 3 (2′,3′-dimethoxyphenyl)-2-phenylpropane-1-methanesulfonate as an oil. $^1$H NMR (CDCl$_3$) delta 2.7 (s, 3H), 2.96 (dd, 1H), 3.1 (dd, 1H), 3.35–3.45 (m, 1H), 3.78 (s, 3H), 3.82 (s, 3H), 4.35 (m, 2H), 6.62 (dd, 1H), 6.77 (dd, 1H), 6.9 (t, 1H), 7.2–7.35 (m, 5H).

Step 4: 4-(2′,3′-Dimethoxyphenyl)-3-phenylbutanenitrile 3-(2′,3′-Dimethoxyphenyl)-2-phenylpropane 1-methanesulfonate (40.5 g, 116 mmol), from step 3, and 17 g (347 mmol) of sodium cyanide were dissolved in 100 mL of dimethyl sulfoxide (DMSO) and the resultant solution was heated to 80° C. After being stirred at 80° C. for 18 h, the reaction mixture was allowed to cool to ambient temperature, diluted with ethyl acetate and washed sequentially with water and brine. The solvents were removed in vacuo to give 25 g (77% yield) of the title compound as an oil. $^1$H NMR (CDCl$_3$) delta 2.56 (d, 2H), 3.02 (d, 1H), 3.05 (d, 1H), 3.25–3.35 (m, 1H), 3.72 (s, 3H), 3.75 (s, 3H), 6.65 (dd, 1H), 6.8 (dd, 1H), 6.93 (t, 1H), 7.2–7.4 (m, 5H).

Step 5: 4-(2′,3′-Dimethoxyphenyl)-3-phenylbutyric acid 4-(2′,3′-Dimethoxyphenyl)-3-phenylbutanenitrile (20 g, 71 mmol), from Step 4, was dissolved in 1.5 L of ethanol. Sodium hydroxide (20 g, 0.5 mol) and 200 mL of water were added and the reaction mixture was heated at reflux temperature for 24 h. The solvent was removed in vacuo and 1 L of water plus 1 L of methylene chloride were added to the residue. The layers were separated and the organic layer discarded. The aqueous layer was acidified with concentrated hydrochloric acid and extracted with 3 L of ethyl acetate. The ethyl acetate solution was dried over anhydrous sodium sulfate and concentrated in vacuo to give 21 g (98% yield) of the title compound as an oil. $^1$H NMR (CDCl$_3$) delta 2.6–2.7 (m, 2H), 2.9 (d, 2H), 3.4–3.5 (m, 1H), 3.72 (s, 3H), 3.82 (s, 3H), 6.6 (dd, 1H), 6.73 (dd, 1H), 6.88 (t, 1H), 7.1–7.3 (m, 5H).

Step 6:

5,6-Dimethoxy 3-phenyl 1,2,3,4 tetrahydro 1-naphthalenone 4-(2′,3′-Dimethoxyphenyl)-3-phenylbutyric acid (37 g, 123 mmol), from Step 5, was added dropwise to 200 g of polyphosphoric acid heated to 100° C. The resultant mixture was stirred and heated at 100° C. for 0.25 h. A mixture of 100 g of ice and 200 mL of water was added to the reaction mixture. The precipitate which formed was filtered, washed with 3×75 mL of water and dissolved in 300 mL of methylene chloride. The methylene chloride solution was dried over anhydrous magnesium sulfate, filtered and concentrated to give 28 g (81% yield) of 5,6-dimethoxy-3-phenyl-1,2,3,4-tetrahydro-1-naphthalenone, m.p. 127–128° C. $^1$H NMR (CDCl$_3$) delta 2.75–3.0 (m, 3H), 3.3–3.5 (m, 2H), 3.8 (s, 3H), 3.95 (s, 3H), 6.93 (d, 1H), 7.25–7.4 (m, 5H), 7.9 (d, 1H).

Method B

Step 1: 2-(2′, 3′-Dimethoxyphenyl)-1,3-dithiane

A solution of 49.5 g (298 mmol) of 2,3 dimethoxybenzaldehyde and 48.4 g (447 mmol) of propane-1,3-dithiol in 800mL of methylene chloride was cooled to 0° C. Boron trifluoride etherate (7.5 mL, 61 mmol) was added dropwise to the cooled solution and the reaction mixture was stirred at 0° C. for 0.5 h, then at ambient temperature for 18 h. The methylene chloride solution was washed with 2×200 mL of 10% aqueous sodium hydroxide solution, 200 mL of water and 100 mL of brine, dried over anhydrous sodium sulfate and concentrated in vacuo to give 75 g 98% yield) of 2-(2′, 3′-dimethoxyphenyl)-1,3-dithiane, m.p. 119–120° C. $^1$H NMR (CDCl$_3$) delta 1.8–2.0 (m, 1H), 2.1–2.25 (m, 1H), 2.86 (t, 1H), 2.91 (t, 1H), 3.05–3.2 (m, 2H), 3.83 (s, 3H), 3.91 (s, 3H), 5.68 (s, 1H), 6.86 (dd, 1H), 7.07 (t, 1H), 7.19 (dd, 1H).

Step 2: Ethyl 4 (2′,3′-dimethoxyphenyl)-4 (1″,3″dithiane)-3 phenylbutyrate

A solution of 2-(2′,3′-dimethoxyphenyl)-1,3-dithiane (57 g, 222 mmol), from Step 1, in 273 mL of dry THF was cooled to −78° C. in a dry ice/acetone bath. To this solution was added 92.2 mL of a 2.5 molar solution of n-butyl lithium in hexane. After the addition was complete the reaction mixture was stirred for 0.75 h at −78° C. 1,3-Dimethyl-2-imidazolidinone (75 mL, 686 mmol), commercially available from Aldrich Chemical Company, was added to the reaction mixture in one portion, followed by 39 g (221 mmol) of ethyl cinnamate (commercially available from Aldrich Chemical Company) added dropwise. The reaction mixture was stirred for 1h at −78° C. then quenched with 50 mL of 10% aqueous acetic acid and allowed to warm to 0° C. The reaction mixture was diluted with 150 mL of diethyl ether and the layers separated. The organic layer was washed with 2×100 mL of saturated aqueous sodium bicarbonate solution, 100 mL of water and 100 mL of brine, dried over anhydrous magnesium sulfate and concentrated to give a crude oily product. The crude product was crystallized from ethyl acetate/hexane to give 32 g (48% yield) of the title compound, m.p. 125–126° C. A second crop of crystals yielded an additional 11 g (total yield 59%) of ethyl 4-(2′,3′-dimethoxy-phenyl)-4-(1″,3′-dithiane)-3-phenylbutyrate, m.p. 124.5–125° C. $^1$ H NMR (CDCl$_3$) delta 0.8 (t, 3H), 1.75–1.9 (m, 2H), 2.5–2.85 (m, 4H), 3.05–3.25 (m, 2H), 3.7–3.95 (m, 2H), 3.88 (s, 3H), 4.0 (s, 3H), 4.45–4.5 (m, 1H), 6.8–6.9 (m, 2H), 7.0–7.4 (m, 6H).

Step 3: Ethyl 4-(2′,3′-dimethoxyphenyl)-3-phenylbutyrate

Ethyl-4-(2′,3′-dimethoxyphenyl)4-(1″,3″-dithiane)-3-phenylbutyrate (14.5 g, 39 mmol), from Step 2, and 145 g Raney nickel and 300 mL of absolute ethanol were mixed together and heated at reflux temperature under 1 atmosphere of hydrogen for 3.25 h. The stirring was stopped and the mixture was allowed to cool slightly before the solvent was decanted from the catalyst. An additional 300 mL of absolute ethanol was added to the catalyst and the mixture stirred and heated to reflux. The stirring was again stopped and the reaction mixture was allowed to cool slightly before the solvent was decanted from the catalyst. The combined supernatants were filtered through Celite filter aid and concentrated in vacuo to give 10.8 g (97% yield) of ethyl 4-(2',3'-dimethoxyphenyl)-3-phenylbutyrate as a clear oil. $^1$H NMR (CDCl$_3$) delta 1.11 (t, 3H), 3.07 (dd, 1H), 3.35 (dd, 1H), 3.81 (s, 3H), 3.84 (s, 3H), 3.9–4.1 (m, 3H), 6.65 (dd, 1H), 6.77 (dd, 1H), 6.88 (t, 1H), 7.2–7.4 (m, 5H).

Step 4: 4-(2',3'-Dimethoxyphenyl)-3-phenylbutyric acid

Ethyl 4-(2',3'-dimethoxyphenyl)-3-phenylbutyrate (40.3 g, 123 mmol), from Step 3, was dissolved in 400 mL of methanol and 62 mL of 3 M aqueous sodium hydroxide solution was added in one portion. The reaction mixture was stirred at ambient temperature for 18 h. The reaction mixture was concentrated and the residue was partitioned between 300 mL of diethyl ether and 200 mL of water. The layers were separated and the aqueous layer was adjusted to pH 6 with 6 M aqueous hydrochloric acid solution and extracted with 3×200 mL of diethyl ether. The organic layers were combined, washed with brine, dried over anhydrous magnesium sulfate and concentrated in vacuo to give 37 g (100% yield) of the title compound as a colorless oil. The $^1$H NMR spectrum was identical to the spectrum reported for the product of Step 5 of Method A, Example 1.

Step 5: 5,6 Dimethoxy-3-phenyl 1,2,3,4-tetrahydro-1 naphthalenone 4-(2',3'-Dimethoxyphenyl) 3-phenylbutyric acid (13.3 g, 44.3 mmol), from Step 4, was treated with 14 mL (216 mmol) of methanesulfonic acid and 200 mL of trifluoroacetic acid at 60° C. for 1.5 h. After cooling the reaction mixture, the trifluoroacetic acid was removed in vacuo and ice water was added to the residue. Methylene chloride was added and the layers separated. The organic layer was washed with 1N aqueous sodium hydroxide solution, water and brine, dried over anhydrous magnesium sulfate, filtered and concentrated under reduced pressure. The residue was recrystallized three times from methanol to give 9.6 q (77% yield) of 5,6 dimethoxy 3-phenyl 1,2,3,4-tetrahydro-1-naphthalenone, m.p. 126°–128° C. 1H NMR spectrum was identical to the spectrum reported for the product of Step 6 of Method A, Example 1.

EXAMPLE 2

1-Aminomethyl-3,4-dihydro-5,6-dihydroxy-3-phenyl-naphthalene

Step 1:
1-Aminomethyl-5,6-dimethoxy-1-hydroxy-3-phenyl-1,2,3,4-tetrahydro-naphthalene 5,6-Dimethoxy-3-phenyl-1,2,3,4-tetrahydro-1-naphthalenone (14.6 g, 51.7 mmol), from Example 1, 24 mL of acetonitrile, 10.3 g (104 mmol) of trimethylsilylcyanide, commercially available from Aldrich Chemical Company, and 100 mg of aluminum chloride were mixed together and heated at reflux temperature for 2.5 h. The reaction mixture was cooled and concentrated. The residue was dissolved in diethyl ether and added dropwise to a solution of 4.3 g (113 mmol) of lithium aluminum hydride in 101 mL of diethyl ether. After the reaction mixture was heated at reflux temperature for 2.5 h, 4.3 mL of water was added dropwise, followed by 4.3 mL of 15% aqueous sodium hydroxide solution, followed by 13 mL of water. The reaction mixture was stirred until a qranular precipitate formed. The solid was filtered and washed with 3×80 mL of methylene chloride. The filtrate was concentrated and the resultant solid was triturated with ethyl acetate/hexane to give 11.9 g (73% yield) of the title compound, m.p. 175°–176° C. $^1$H NMR (d$_6$ DMSO) delta 2.03 (t, 1H), 2.28 (dt, 1H), 2.65 (dd, 1H), 2.83 (dd, 1H), 2.95–3.1 (m, 2H), 3.28 (dd, 1H), 3.75 (s, 3H), 3.86 (s, 3H), 6.87 (d, 1H), 7.2–7.4 (m, 6H)

Step 2:
1-Aminomethyl-3,4-dihydro-5,6-dimethoxy-3-phenyl-naphthalene hydrochloride 1 Aminomethyl-5,6-dimethoxy-1-hydroxy-3-phenyl-1,2,3,4-tetrahydro-naphthalene (11.5 g, 37 mmol), from Step 1, was heated at reflux temperature in 300 mL of isopropyl alcohol saturated with hydrochloric acid for 2 h. The resultant solution was concentrated and the solid residue was triturated with hot toluene to give 10.6 g (98% yield) of 1-aminomethyl-3,4-dihydro-5,6-dimethoxy-3-phenyl-naphthalene hydrochloride, m.p. 189.5°–190° C. $^1$H NMR (d$_6$-DMSO) delta 2.78 (dd, 1H), 3.11 (dd, 1H), 3.2–3.4 (m, 2H +H$_2$O), 3.6 (s, 3H), 3.81 (s, 3H), 3.93 (d, 1H), 6.1 (d, 1H), 6.93 (d, 1H), 7.12 (d, 1H), 7.2–7.4 (m, 5H).

Step 3:
1-Aminomethyl-3,4-dihydro-5,6-dihydroxy-3-phenyl-naphthalene hydrobromide (Example 2A)

1-Aminomethyl-3,4-dihydro-5,6-dimethoxy-3-phenyl-naphthalene hydrochloride (6.0 g, 20.2 mmol), from Step 2, was suspended in 200 mL of methylene chloride and boron tribromide (90.5 mL of 1M solution of BBr$_3$ in methylene chloride) was added dropwise while the reaction mixture was being cooled (to −78° C.) in a dry ice/acetone bath. The reaction mixture was warmed to 0° C. and stirred for 0.5 h, then again cooled to −78° C. in a dry ice/acetone bath. Methanol (50 mL) was added dropwise to the reaction mixture, which was allowed to warm to ambient temperature then concentrated in vacuo. Methanol was added to the residue and the solution was reconcentrated. This residue was dissolved in a small amount of methanol and the methanol solution was aded to 700 mL of diethyl ether. The precipitate which formed was filtered, washed with diethyl ether and recrystallized from methanol/ether to give 2.5 g (45% yield) of 1-aminomethyl-3,4-dihydro-5,6-dihydroxy-3-phenyl-naphthalene hydrobromide, m.p. 223°–225° C. $^1$H NMR (d$_6$ DMSO) delta 2.68 (dd, 1H), 3.09 (dd, 1H), 3.6–3.7 (m, 1H), 3.9 (s, 2H), 5.97 (d, 1H), 6.69 (m, 2H), 7.2–7.35 (m, 5H), 8.1 (br s, 3H), 8.4 (s, 1H), 9.5 (s, 1H).

Step 4:
1-Aminomethyl-3,4-dihydro-5,6-dihydroxy-3-phenyl-naphthalene hydrochloride (Example 2B)

A slurry of 10 g (25 mmol) of 1-aminomethyl-3,4-dihydro-5,6-dimethoxy-3-phenyl-naphthalene hydrochloride, from Step 2, in 150 mL of dichloroethane was cooled to 10° C. under a nitrogen atmosphere. Boron trichloride was passed through the reaction mixture until 27 g (230 mmol) had been added. The reaction mixture was allowed to warm to ambient temperature and stirred for 18 h. The reaction mixture was then recooled in ice and 100 mL of methanol was added dropwise. The reaction mixture was again allowed to warm to ambient temperature and concentrated in vacuo. Twice, 500 mL portions of methanol were added to the residue and it was reconcentrated. The resultant foam was dissolved in 40 mL of ethanol, filtered and the solution was treated with 40 mL of methylene chloride and 80 mL of heptane. Off-white crystals of 1-aminomethyl-3,4-dihydro-5,6-dihydroxy-3-phenyl naphthalene hydrochloride (5.1 g, 56% yield) were collected by filtration, m.p. 204°–205° C. The $^1$H NMR spectrum was identical to the spectrum for the product of Example 2A.

EXAMPLE 3

1-Aminomethyl-5,6-bis(acetoxy)-3,4-dihydro-3-phenyl-naphthalene hydrochloride

A suspension of 7.6 g (25 mmol) of 1-aminomethyl-3,4-dihydro-5,6-dihydroxy-3-phenyl-naphthalene hydrochloride (Example 2B) in 400 mL of acetic anhydride saturated with anhydrous hydrogen chloride was stirred at ambient temperature for 48 h. Diethyl ether (approximately 2 L) was added and a solid was collected by filtration and washed with diethyl ether. Crystallization of the crude material (6.7 q) was achieved by dissolving the powder in 400 mL of hot ethanol, adding 100 mL of water, filtering the solution hot and allowing it to cool. The white crystals which formed were filtered and dried to give 2.8 g (29% yield) of 1-aminomethyl-5,6-bis(acetoxy)-3,4-dihydro-3-phenyl-naphthalene hydrochloride, m.p. 207°–208° C. $^1$H NMR (d$_6$ DMSO) delta 2.28 (s, 6H), 2.62 (dd, 1H), 2.95 (dd, 1H), 3.7–3.8 (m, 1H), 3.97 (s, 2H), 6.25 (d, 1H), 7.19 (d, 1H), 7.2–7.4 (m, 6H), 8.41 (br s, 3H).

EXAMPLE 4

1-Aminomethyl-5,6-bis(trimethylacetoxy)-3,4-dihydro-3-phenyl-naphthalene hydrochloride

Step 1:
N-t-Butyloxycarbonyl-1-aminomethyl-3,4-dihydro-5,6-dihydroxy-3-phenyl-naphthalene Triethylamine (7 mL) was added to a solution of 15 g (56 mmol) of 1-aminomethyl-3,4-dihydro-5,6-dihydroxy-3-phenyl-naphthalene hydrochloride, from Step 4 of Example 2, in 100 mL of dimethylformamide (DMF). The solution was cooled to 0° C. and a solution of di-t-butyl-dicarbonate (18 g, 82.5 mmol) in 50 mL of DMF was added over a period of 1 h. After the addition was complete, 250 mL of water was added to the reaction mixture and it was extracted with ethyl acetate. The combined organic layers from the extraction were washed with 1 N hydrochloric acid solution and brine, dried over anhydrous magnesium sulfate, filtered and concentrated in vacuo. The brown residue was triturated with boiling hexanes to give 16.7 g (99% yield) of the title compound as an off white solid, m.p. 175°–177° C. $^1$H NMR (CDC13) delta 1.45 (s, 9H), 2.74 (dd, 1H), 3.19 (dd, 1H), 3.6–3.7 (m, 1H), 4.1–4.25 (m, 2H), 4.71 (br s, 1H), 5.4 (br s, 1H), 5.88 (d, 1H), 6.0 (br s, 1H), 6.68 (s, 2H), 7.2–7.35 (m, 5H).

Step 2:
N-t-Butyloxycarbonyl-1-aminomethyl-5,6-bis(trimethylacetoxy)-3,4-dihydro-3-phenyl-naphthalene N-t-Butyloxycarbonyl-1-aminomethyl-3,4-dihydro-5,6-dihydroxy-3-phenyl-naphthalene (3 g, 8.16 mmol), from Step 1, and 11 mL of triethylamine were combined and cooled to 0° C. A solution of trimethylacetyl chloride (2.1 mL, 17 mmol) in 13 mL of dioxane was added dropwise to the cooled solution. The reaction mixture was allowed to warm to ambient temperature and stirred at ambient temperature for 2 h. Water (25 mL) was added to the reaction mixture and the pH was adjusted to approximately 4 with concentrated phosphoric acid. The reaction mixture was extracted with diethyl ether. The combined ether extracts were washed with aqueous saturated sodium bicarbonate solution, water and brine, dried over anhydrous magnesium sulfate, filtered and concentrated in vacuo to give 4.26 g (89% yield) of N t-butyloxycarbonyl-1-aminomethyl-5,6-bis(trimethylacetoxy)-3-phenyl 3,4-dihydro naphthalene as an off-white solid, m.p. 64°–69° C. $^1$H NMR (CDC13) delta 1.3 (s, 9H), 1.34 (s, 9H), 1.45 (s, 9H), 2.68 (dd, 1H), 2.93 (dd, 1H), 3.6–3.75 (m, 1H), 4.1–4.3 (m, 2H), 4.63 (br s, 1H), 6.03 (d, 1H), 6.98 (d, 1H), 7.15–7.35 (m, 6H).

Step 3:
1-Aminomethyl-5,6-bis(trimethylacetoxy)-3,4-dihydro-3-phenyl-naphthalene hydrochloride N-t-Butyloxycarbonyl-1-aminomethyl-5,6-bis(trimethylacetoxy)-3,4-dihydro-3-phenyl naphthalene (14 g, 26 mmol), from Step 2, was dissolved in 75 mL of dioxane and saturated with anhydrous hydrogen chloride. The reaction mixture was stirred for 2 h and concentrated in vacuo. The solid residue was dissolved in a minimum amount of methanol and the methanol solution was added dropwise to an excess amount (500 mL) of diethyl ether. The precipitate was filtered, washed with diethyl ether and dried to give 9.1 g 90% yield) of 1-aminomethyl-5,6-bis(trimethylacetoxy)-3,4-dihydro-3-phenyl-naphthalene hydrochloride as a white powder, m.p. 210°–212° C. $^1$H NMR (d$_6$ DMSO) delta 1.25 (s, 9H), 1.28 (s, 9H), 2.61 (dd, 1H), 2.89 (dd, 1H), 3.75–3.85 (m, 1H), 3.99 (s, 2H), 6.28 (d, 2H), 7.15 (d, 1H), 7.2–7.35 (m, 5H), 7.37 (d, 1H), 8.37 (br s, 3H).

EXAMPLE 5

[1R,3S]1-Aminomethyl-5,6-dihydroxy-3-phenyl-1,2,3,4-tetrahydro-naphthalene hydrobromide

Step 1:
[1R,3S]1-Aminomethyl-5,6-dimethoxy-3-phenyl-1,2,3,4-tetrahydro-naphthalene hydrochloride To 0.2 g (0.67 mmol) of 1 aminomethyl 3,4-dihydro-5,6-dimethoxy-3-phenyl naphthalene hydrochloride, from Step 2, of Example 2, in 5 mL of absolute ethanol was added 0.05 g of 10% palladium supported on carbon. The reaction mixture was sealed under a blanket of hydrogen and stirred overnight at ambient temperature. The reaction mixture was flushed with nitrogen before it was filtered through Celite filter aid and washed with 15 mL of absolute ethanol and 15 mL of methylene chloride. The filtrate was concentrated to give 0.2 g (100% yield) of [1R,3S]1-aminomethyl-5,6-dimethoxy-3-phenyl 1,2,3,4-tetrahydro-naphthalene hydrochloride, m.p. 230°–231° C. $^1$H NMR (d$_6$-DMSO) delta 2.15–2.25 (m, 1H), 2.5–2.65 (m, 1H), 2.8–2.95 (m, 2H), 3.0–3.1 (m, 1H), 3.1–3.4 (m, 1H), 3.45–3.5 (m, 1H), 3.66 (s, 3H), 3.78 (s, 3H), 6.95 (d, 1H), 7.12 (d, 1H), 7.2–7.3 (m, 1H), 7.35–7.45 (m, 4H), 8.0 (br s, 3H).

Step 2:
[1R,3S]1-Aminomethyl-5,6-dihydroxy-3-phenyl-1,2,3,4-tetrahydro-naphthalene hydrobromide

[1R,3S]1-Aminomethyl-5,6-dimethoxy-3-phenyl-1,2,3,4-tetrahydro-naphthalene hydrochloride (0.2 g, 0.67 mmol), from Step 1, was suspended in 13 mL of methylene chloride and the suspension was cooled to −78° C. in a dry ice/acetone bath. Boron tribromide (3 mL of a 1M solution in methylene chloride, 3 mmol) was added and the reaction mixture was allowed to warm to ambient temperature, kept at ambient temperature for 1.5 h then cooled to −78° C. Methanol (3 mL) was added to the reaction mixture and it was again allowed to warm to ambient temperature then concentrated in vacuo. The residue was redissolved in methanol and reconcentrated. The residue was again redissolved in methanol and the methanol solution was added to a large excess of diethyl ether. The resultant precipitate was filtered and recrystallized from ethanol/diethyl ether to give 0.14 g (64% yield) of the title compound as a white powder, m.p. 256°–259° C. 1H NMR (d6-DMSO) delta 1.63 (q, 1H), 2.1–2.25 (m, 1H), 2.4–2.5 (m, 1H), 2.75–2.95 (m, 2H), 3.02 (dd, 1H), 3.15–3.3 (m, 1H), 3.4–3.5 (m, 1H), 6.68 (s, 2H), 7.2–7.3 (m, 1H), 7.3–7.4 (m, 4H), 7.8 (br s, 3H), 8.2 (br s, 1H), 9.1 (br s, 1H).

EXAMPLE 6

1-Aminomethyl-3-cyclohexyl-3,4-dihydro-5,6-dihydroxynaphthalene hydrobromide

Step 1: Ethyl 3-cyclohexylpropenoate

Sodium hydride (2.6 g, 108 mmol) was added to 100 mL of THF and 19.8 mL (98.9 mmol) of triethylphosphonoacetate, commercially available from Aldrich Chemical Company, was added dropwise at 0° C. The reaction mixture was stirred for 1 h at ambient temperature and 12.1 mL (99.9 mmol) of cyclohexanecarboxaldehyde, commercially available from Aldrich Chemical Company, was added. The reaction mixture was heated at reflux temperature for 15 min then cooled and filtered. The filtrate was concentrated under reduced pressure and the product was distilled at 140° C. (15 Torr) to give 15.2 g (84% yield) of ethyl 3-cyclohexylpropenoate as a clear liquid. 1H NMR (CDCl3) delta 1.1–1.4 (m, 6H), 1.3 (t, 3H), 1.6–1.8 (m, 5H), 2.05–2.2 (m, 1H), 4.2 (q, 2H), 5.75 (d, 1H), 6.92 (d, 1H).

Step 2:
1-Aminomethyl-3-cyclohexyl-3,4-dihydro-5,6-dimethoxy-naphthalene-hydrochloride 2 (2',3'-Dimethoxyphenyl)-1,3-dithiane, from Step 1 of Example 1, Method B, and ethyl 3-cyclohexylpropenoate, from Step 1 of this Example, were condensed as described in Step 2 of Example 1, Method B. The adduct was treated with Raney nickel and sodium hydroxide to give the corresponding acid. The acid was cyclized with polyphosphoric acid as described in Step 6 of Example 1, Method A, to give 3-cyclohexyl-5,6-dimethoxy-1,2,3,4-tetrahydro naphthalenone. This ketone was treated with trimethylsilylcyanide in the presence of aluminum chloride and reduced with lithium aluminum hydride as described in Step 1 of Example 2 to give 1-aminomethyl-3-cyclohexyl-5,6-dimethoxy-1-hydroxy-1,2,3,4-tetrahydro-naphthalene. The hydroxy group was eliminated by treatment with anhydrous hydrogen chloride in isopropyl alcohol as described in Step 2 of Example 2 to give 1-aminomethyl-3-cyclohexyl-3,4-dihydro-5,6-dimethoxy-naphthalene hydrochloride, m.p. 178°–179° C., 1H NMR (d6 DMSO) delta 1.0–1.4 (m, 7H), 1.5–1.9 (m, 6H), 2.0–2.2 (m, 1H), 2.5 (dd, 1H), 2.7 (dd, 1H), 3.6 (s, 3H), 3.81 (s, 3H), 5.8 (d, 1H), 6.6 (m, 2H).

Step 3:
1-Aminomethyl-3-cyclohexyl-3,4-dihydro-5,6-dihydroxy-naphthalene hydrobromide 1-Aminomethyl-3-cyclohexyl-3,4-dihydro-5,6-dimethoxy-naphthalene hydrochloride (2.7 g, 8.9 mmol), from Step 2, was dissolved in 72 mL of methylene chloride and cooled to −78° C. Boron tribromide (36 mL of a 1 M solution in methylene chloride) was added and the reaction mixture was warmed to 0° C. for 1 h. The reaction mixture was cooled aqain to −78° C. and 30 mL of methanol was added. After stirring at ambient temperature for 1 h, the reaction mixture was concentrated, diluted with methanol and reconcentrated. The residue was dissolved in methanol and the methanol solution was added dropwise to an excess amount of diethyl ether. The precipitate was filtered and recrystallized from ethanol/ether to give 2.2 g ( 79% yield) of the title compound, m.p. 212°–213° C. 1H NMR (d6 DMSO) delta 1.0–1.4 (m, 7H), 1.55–1.9 (m, 6H), 2.05–2.15 (m, 1H), 2.47 (dd, 1H), 2.74 (dd, 1H), 5.83 (d, 1H), 6.60 (m, 2H).

EXAMPLE 7

[1R,3S]1-Aminomethyl-3-cyclohexyl-5,6-dihydroxy-1,2,3,4-tetrahydro-naphthalene hydrobromide

Step 1:
[1R,3S]1-Aminomethyl-3-cyclohexyl-5,6-dimethoxy-1,2,3,4-tetrahydro-naphthalene hydrochloride 1-Aminomethyl-3-cyclohexyl-3,4-dihydro-5,6-dimethoxy-naphthalene hydrochloride (1 g, 3.3 mmol), from Step 2 of Example 6, was dissolved in 20 mL of ethanol and 0.25 g of 10% palladium on carbon was added to the ethanol solution. The reaction mixture was sealed under a blanket of one atmosphere of hydrogen gas and shaken at ambient temperature for 24 h. The reaction mixture was filtered to remove the catalyst and concentrated to give 1 g (100% yield) of the title compound, m.p. 282°–283° C. 1H NMR (d6-DMSO) delta 1.0–1.5 (m, 8H), 1.5–1.9 (m, 5H), 2.0–2.2 (m, 2H), 2.7–3.1 (m, 3H), 3.3–3.4 (m, 1H), 3.8 (s, 3H), 3.9 (s, 3H), 6.4–6.8 (m, 2H).

Step 2:
[1R,3S]1-Aminomethyl-3-cyclohexyl-5,6-dihydroxy-1,2,3,4-tetrahydro-naphthalene hydrobromide

[1R,3S]1-Aminomethyl-3-cyclohexyl-5,6-dimethoxy-1,2,3,4-tetrahydro-naphthalene hydrochloride (0.7 g, 2.3 mmol), from Step 1, was suspended in 20 mL of methylene chloride at −78° C. Boron tribromide (9.7 mL of a 1M solution in methylene chloride, 9.7 mmol) was added and the reaction mixture was allowed to warm to ambient temperature. After stirring at ambient temperature for 1 h, the reaction mixture was cooled to −78° C. and 10 mL of methanol was added. The reaction mixture was again allowed to warm to ambient temperature and stirred at ambient temperature for 1 h. The solvent was removed in vacuo and methanol was added to the residue. The methanol solution was concentrated and the residue dissolved in a minimal amount of methanol and added dropwise to a large excess of diethyl ether. The precipitate was filtered and recrystallized from ethanol/diethyl ether to give 0.48 g (65% yield) of [1R,3S]1-aminomethyl-3-cyclohexyl-5,6-dihydroxy-1,2,3,4-tetrahydro-naphthalene hydrobromide, m.p. 203°–204° C. $^1$H NMR (d$_6$-DMSO) delta 0.9–1.5 (m, 8H), 1.6–1.9 (m, 5H), 2.0–2.1 (m, 2H), 2.7–3.0 (m, 3H), 3.3–3.4 (m, 1H), 6.5–6.7 (m, 2H).

EXAMPLE 8

[1R,3S]1-Bromomethyl-3-t-butyl-5,6-cyclohexylidenedioxy-3,4-dihydro 1H-2-benzopyran

Step 1: Epoxide Synthesis 3,3-Dimethyl-1,2-epoxybutane, the epoxide used in the synthesis of [1R,3S]1-bromomethyl-3-t-butyl-5,6-cyclohexylidenedioxy-3,4-dihydro-1H-2-benzopyran, is commercially available. Epoxides necessary for the synthesis of other benzopyran derivatives of the present invention which are not commercially available were synthesized by either Method A or Method B described below.

Method A: 1-Cyclohexyl ethylene oxide

Sodium hydride (4.5 g, 187.5 mmol) and trimethylsulfoxonium iodide (41.25 g, 187.5 mmol) were combined in a 3-neck flask equipped with a mechanical stirrer and an addition funnel. Dimethyl sulfoxide (DMSO) was added slowly over a 30 min period, until 200 mL had been added. Gas was evolved throughout the addition. A solution of cyclohexane carboxaldehyde (21.8 mL, 180 mmol) in 50 mL of DMSO was added dropwise to the reaction mixture over a 15 min period. The reaction mixture was heated to 55° C. and stirred at 55° C. for 30 min. The reaction mixture was cooled to ambient temperature and poured into 500 mL of water. The aqueous solution was extracted with 3×100 mL of diethyl ether. The combined ether extracts were washed with water and brine, dried over anhydrous magnesium sulfate and concentrated in vacuo. The crude product was distilled (44° C., 0.1 mm) to give 14 g (62% yield) of 1-cyclohexyl ethylene oxide as a clear colorless liquid.

Method B: 1-Benzyl ethylene oxide

A solution of m chloroperbenzoic acid (mCPBA; 17 g, 0.1 mol) in 120 mL of methylene chloride was added (at ambient temperature) dropwise to a solution of allyl benzene (10 g, 85 mmol) in 200 mL of methylene chloride. After the reaction mixture was stirred for 5 h with a mechanical stirrer, 5 additional qrams of m CPBA were added and the reaction mixture stirred for another 2 h. The reaction mixture was then diluted with 200 mL of ether, washed with 2×100 mL of aqueous sodium bisulfite solution, 1×100 mL of aqueous sodium bicarbonate solution and 1×100 mL of brine. The organic solution was dried over anhydrous magnesium sulfate, filtered and concentrated in vacuo. The residue was purified by bulb-to-bulb distillation (60° C., 0.1 mm) to give 8.5 g (77% yield) of 1-benzyl ethylene oxide as a clear colorless liquid.

Step 2: 3,3-Dimethyl-1-(spiro[(1,3-benzodioxole)-2,1'-cyclohexane])-2-butanol n-Butyl lithium (12.6 mL of 2.5 M solution in hexane, 32 mmol) was added to a solution of spiro[(1,3-benzodioxole)-2,1'-cyclohexane](5 g, 26.3 mmol), prepared as described by Boeckmann and Schill in *Chemische Berichte*, 110, 703 (1977), in 40 mL of THF at 0° C. After 4 h, 3,3-dimethyl-1,2-epoxybutane (2.5 g, 25 mmol), commercially available from Lancaster Chemical Company, was added dropwise and the reaction mixture was warmed to 25° C. After 3 h at 25° C., the reaction mixture was poured into saturated aqueous ammonium chloride solution and extracted with 3×75 mL of diethyl ether. The combined ether extracts were washed with 50 mL of aqueous ammonium chloride solution and 50 mL of brine, dried over anhydrous magnesium sulfate, filtered and concentrated in vacuo to an oil. The oil was purified on silica gel eluted with 10% ethyl acetate in hexane to give 3.5 g (48% yield) of the title compound as a viscous oil. DCI MS: 308 (M+NH$_4$)$^+$. $^1$H NMR (d$_6$-DMSO) delta 0.89 (s, 9H), 1.4–1.9 (m, 10H), 2.27 (dd, 1H, J=14.4,9.3 Hz), 2.75 (dd, 1H, J=14.4, 3.0 Hz), 3.3 (m, 1H), 4.38 (d, 1H, J=6.3 Hz), 6.18 (m, 3H).

Step 3A: [1R,3S]-1-Bromomethyl-3-t-butyl-5,6-cyclohexylidenedioxy-3,4-dihydro-1H-2-benzopyran Boron trifluoride etherate (2.88 mL, 23.5 mmol) was added dropwise to a stirred solution of the product of Step 2 (3.4 g, 11.7 mmol) and bromoacetaldehyde dimethyl acetal (1.4 mL, 11.7 mmol) in 15 mL of methylene chloride at −25° C. The reaction mixture was allowed to warm to 0° C. After 1 h at 0° C., the reaction mixture was diluted with 20 mL of diethyl ether and poured into 50 mL of aqueous sodium carbonate solution. The resultant mixture was extracted with 3×50 mL of diethyl ether. The combined ether extracts were washed with aqueous sodium bicarbonate solution and brine, dried over anhydrous magnesium sulfate, filtered and concentrated under reduced pressure. The residue was purified by column chromatography on silica gel eluted with 2.5% ethyl acetate in hexane to give 2.85 g (61% yield) of the title compound as a colorless solid, m.p. 113°–114° C. DCI MS: 414 (M+NH$_4$)$^+$. $^1$H NMR (CDCl$_3$) delta 1.0 (s, 9H), 1.4–1.95 (m, 10H), 2.6 (m, 2H), 3.28 (dd, 1H, J=9.3, 5.4 Hz), 3.52 (dd, 1H, J=11.25, 7.5 Hz), 3.85 (dd, 1H, J=11.25, 3.0 Hz), 4.87 (m, 1H), 6.5 (d, 1H, J=9.0 Hz), 6.6 (d, 1H, J=9.0 Hz).

Alternate Step 3B: [1R,3S]-1-(2-Bromoethyl)-3-t-butyl-5,6-cyclohexylidenedioxy-3,4-dihydro-1H-2-benzopyran The title compound was prepared following the procedure described in Step 3 above and using 3-bromopropionaldehyde dimethyl acetal instead of bromoacetaldehyde dimethyl acetal.

EXAMPLE 9

[1R,3S]1-Aminomethyl-3-t-butyl-3,4-dihydro-5,6-dihydroxy-1H-2 benzopyran hydrochloride

Step 1: [1R,3S]1-Azidomethyl-3-t-butyl-5,6-cyclohexylidenedioxy-3,4-dihydro-1H-2-benzopyran Lithium azide (1.6 g, 31 mmol) was added to a solution of the product of Example 8 (2.5 g, 6.35 mmol) in 12 mL of dimethylformamide (DMF) at 25° C. The reaction mixture was heated at 75° C. for 2h then cooled and poured into 50 mL of water. The aqueous solution was extracted with 3×50 mL of diethyl ether. The combined ether extracts were washed with 50 mL of water, 50 mL of brine, dried over anhydrous magnesium sulfate, filtered and concentrated in vacuo. The residue was purified by column chromatography on silica gel eluted with 2.5% ethyl acetate in hexane to give 1.56 g (69%) of the title compound as a colorless syrup. MS DCI: 375 (M+NH$_4$)$^+$, 358 (M+H)$^+$. $^1$H NMR (CDCl$_3$) delta 1.1 (s, 9H), 1.4–1.95 (m, 10H), 2.6

(m, 2H), 3.3 (dd, 1H, J=8.7, 6.0 Hz), 3.42 (dd, 1H, J=13.5, 7.5 Hz), 3.52 (dd, 1H, J=13.5, 3.0 Hz), 4.9 (m, 1H), 6.42 (d, 1H, J=9.0 Hz), 6.59 (d, 1H, J=9.0 Hz).

Step 2:
[1R,3S]1-Aminomethyl-3-t-butyl-5,6-cyclohexylidenedioxy-3,4-dihydro 1H-2-benzopyran hydrochloride Lithium aluminum hydride (LAH) solution (4.2 mL of 1 M solution in ether, 4.2 mmol) was added dropwise to a solution of [1R,3S]1-azidomethyl-3-t-butyl-5,6-cyclohexylidenedioxy-3,4-dihydro 1H-2-benzopyran (1.5 g, 4.2 mmol) in 25 mL of dry diethyl ether at 0° C. After 15 min, the reaction mixture was allowed to warm to 25° C. and was stirred at 25° C. for 1 h. The reaction mixture was cooled to 0° C. and the reaction was quenched by the sequential addition of 0.16 mL of water 0.16 mL of 15% aqueous sodium hydroxide solution and 0.48 mL of water. The precipitate was removed by filtration and washed with ether. The filtrate was concentrated in vacuo. The crude amine product was dissolved in 15 mL of diethyl ether and diethyl ether saturated with dry hydrochloric acid was added in excess. The solid was collected by vacuum filtration and washed with diethyl ether and dried to give 1.48 g (96% yield) of the title compound as a colorless solid, m.p. 164°–167° C. DCI MS: 332 (M+H)+. $^1$H NMR (d$_6$-DMSO) delta 1.0 (s, 9H), 1.4–1.9 (m, 10H), 2.6 (m, 2H), 2.9 (dd, 1H, J=14.7, 10.5 Hz), 3.2 (m, 2H), 3.5 (dd, 1H, J=14.7, 3.0 Hz), 4.82 (bd, 1H, J=8 Hz), 6.7 (m, 2H), 7.9 (bs, 2H).

Step 3: [1R,3S]1-Aminomethyl-3-t-butyl-3,4 dihydro-5,6-dihydroxy-1H-2-benzopyran hydrochloride A solution of [1R,3S]1-aminomethyl-3-t-butyl-5,6-cyclohexylidenedioxy-3,4-dihydro-1H-2-benzopyran hydrochloride, from Step 2, (1 g, 2.72 mmol) in 15 mL of ethanol was saturated with anhydrous hydrogen chloride. The solution was heated to reflux temperature. After 2 h at reflux temperature, the solution was concentrated to approximately 2 mL. A solid was precipitated with diethyl ether, filtered, washed with diethyl ether and dried in a vacuum oven at 80° C. to give 630 mg (81% yield) of the title compound as a colorless powder, m.p. 258° C. IR 3200, 1620, 1490, 1300, 1060 cm$^{-1}$. DCI MS: 252 (M+H)+. $^1$H NMR (d$_6$DMSO) delta 1.0 (s, 9H), 2.38 (dd, 1H, J=16.5, 12 Hz), 2.63 (dd, 1H, J=16.5, 2.8 Hz), 2.85 (m, 1H), 3.22 (dd, 1H, J=12.0, 4.2 Hz), 3.45 (m, 1H), 4.8 (bd, 1H, J=7.5 Hz), 6.5 (d, 1H, J=7.8 Hz), 6.65 (d, 1H, J=7.8 Hz), 7.9 (bs, 2H), 8.46 (bs, 1H), 9.22 (bs, 1H). Analysis calculated for $C_{14}H_{22}ClNO_3$: C, 58.43; H, 7.70; N, 4.90. Found: C, 58.37; H, 7.69; N, 4.77.

EXAMPLES 10–34

Following the synthesis outlined in Examples 8 and 9, using the appropriate epoxide and the appropriate aldehyde acetal, Examples 10–34 were made, as their hydrochloride salts unless otherwise noted, as disclosed in Table 1. The structure of each was confirmed by melting point (m.p), elemental analysis and mass spectra as designated.

TABLE 1

Examples 10-34

| Example # | Compound | Epoxide* | m.p. | MS** | | Elemental Analysis C H N |
|---|---|---|---|---|---|---|
| 10 | structure with OH, HO, phenyl, O, NH₂ | styrene oxide, 1 | 146° C. | 272 | calc: Found: | 60.60 6.05 4.42 / 60.63 6.27 4.20 |
| 11 | structure with OMe, MeO, phenyl, O, NH₂*** | styrene oxide, 1 | 121° C. | 300 | calc: Found: | 64.42 6.82 3.95 / 64.08 6.69 3.93 |
| 12 | structure with OH, HO, cyclohexyl, O, NH₂ | cyclohexyl epoxide, 2 | 225° C. | 278 | calc: Found: | 61.24 7.71 4.46 / 61.23 7.83 4.34 |
| 13 | structure with OH, HO, ethyl, O, NH₂ | propylene/butyl epoxide, 1 | 204–206° C. | 224 | calc: Found: | 55.5 6.99 5.39 / 55.85 7.15 5.31 |

TABLE 1-continued

Examples 10-34

| Example # | Compound | Epoxide* | m.p. | MS** | | Elemental Analysis | | |
|---|---|---|---|---|---|---|---|---|
| | | | | | | C | H | N |
| 14 | (structure: cyclohexyl-CH2 attached to dihydroxyphenyl with CH(OH)-CH2-NH2 side chain) | (cyclohexyl spiro epoxide) 2 | 234 | 264 | calc: Found: | 60.10 60.20 | 7.40 7.53 | 4.67 4.63 |
| 15 | (structure: cyclohexyl-CH2-CH2 attached to dihydroxyphenyl with epoxide and NH2) | (cyclohexene oxide) 1 | 230° C. | 250 | calc: Found: | 58.84 58.94 | 7.06 7.27 | 4.90 4.78 |
| 16 | (structure: 4-methoxyphenoxymethyl attached to dihydroxyphenyl with CH-O-CH2-NH2) | (4-methoxyphenyl glycidyl ether) | 220-221° C. | 332 | calc: Found: | 58.78 58.39 | 6.03 6.20 | 3.81 3.71 |
| 17# | (structure: benzyl attached to dihydroxyphenyl with CH-O-CH2-NH2) | (styrene oxide) 1 | 158° C. [alpha]$_D$ = −116.5° (C = 0.405, 1N HCl) | 272 | calc: Found: | 60.60 60.63 | 6.05 6.27 | 4.42 4.20 |

*1 = commercially available 2 = synthesized by Method A (Example 8) 3 = synthesized by Method B (Example 8)
**DCI MS (M + H)$^+$
***formic acid salt
****free base

TABLE 1-continued

Examples 10-34

| Example # | Compound | Epoxide* | m.p. | MS** | | Elemental Analysis | | |
|---|---|---|---|---|---|---|---|---|
| | | | | | | C | H | N |
| 18 | [structure: HO, OH phenyl with CH2-CH(OH)-CH2-O-Ph and CH2-NH2 sidechain] | [phenoxymethyl epoxide] | 230° C. | 302 | calc:<br>Found: | 60.45<br>60.34 | 5.97<br>6.04 | 4.15<br>4.02 |
| 19 | [structure with biphenyl ether] | [biphenyl-2-yloxymethyl epoxide] | 205° C. | 378 | calc:<br>Found: | 66.74<br>66.54 | 5.85<br>5.88 | 3.38<br>3.37 |
| 20 | [structure with 4-tert-butylphenoxy] | [4-tert-butylphenoxymethyl epoxide] | 217° C. | 358 | calc:<br>Found: | 64.03<br>63.90 | 7.16<br>7.18 | 3.56<br>3.51 |
| 21 | [structure with 4-bromophenoxy] | [4-bromophenoxymethyl epoxide] | 225° C. | 380 | calc:<br>Found: | 49.00<br>49.03 | 4.60<br>4.65 | 3.36<br>3.33 |

*1 = commercially available 2 = synthesized by Method A (Example 8) 3 = synthesized by Method B (Example 8)
**DCI MS (M + H)+
***formic acid salt
****free base
Prepared by the procedure described in Examples 8, 9 and 46 using (−) B-chlorodiisopinocampheylborane.

TABLE 1-continued

Examples 10-34

| Example # | Compound | Epoxide* | m.p. | MS** | | Elemental Analysis | | |
|---|---|---|---|---|---|---|---|---|
| | | | | | | C | H | N |
| 22 | (adamantyl compound with OH, HO, O, NH2) | (adamantyl epoxide) 2 | 250° C. | 330 | calc:<br>Found: | 65.65<br>65.59 | 7.71<br>7.83 | 3.83<br>3.73 |
| 23 | (benzyl compound with OH, HO, O, NH2) | (phenyl epoxide) 3 | 242° C. | 286 | calc:<br>Found: | 63.45<br>63.32 | 6.26<br>6.30 | 4.35<br>4.27 |
| 24 | (phenethyl compound with OH, HO, O, NH2) | (phenyl propyl epoxide) 1 | 215° C. | 300 | calc:<br>Found: | 64.38<br>64.33 | 6.60<br>6.65 | 4.17<br>4.06 |
| 25 | (benzyl compound with OH, HO, Br, O, NH2) | (phenyl epoxide) 1 | 241° C. | 350 | calc:<br>Found: | 49.70<br>49.77 | 4.43<br>4.44 | 3.62<br>3.58 |

TABLE 1-continued
Examples 10-34

| Example # | Compound | Epoxide* | m.p. | MS** | | Elemental Analysis | | |
|---|---|---|---|---|---|---|---|---|
| | | | | | | C | H | N |
| 26 | [structure: HO-, OH-phenyl with CH(OH)CH2- chain and CH2CH(OH)C(CH3)3, with CH2CH2NH2****] | [2,2-dimethyl epoxide] 1 | 130–134° C. | 266 | | | | |
| 27 | [structure: bis-phenol with cyclohexane spiroketal, cyclohexylmethyl chain, and CH(OH)CH2NH2] | [cyclohexyl epoxide] 2 | 162–163° C. | 358 | calc: Found: | 73.90 73.82 | 8.74 8.74 | 3.92 3.67 |
| 28 | [structure: HO-, OH-phenyl with hexyl-CH(OH)CH2- chain and CH(OH)CH2NH2] | [hexyl epoxide] 1 | 200° C. | 308 | calc: Found: | 62.87 62.80 | 8.79 8.69 | 4.07 4.03 |
| 29 | [structure: HO-, OH-phenyl with octyl-CH(OH)CH2- chain and CH(OH)CH2NH2] | [octyl epoxide] 1 | 193° C. | 336 | calc: Found: | 64.58 64.74 | 9.21 9.13 | 3.77 3.69 |

*1 = commercially available 2 = synthesized by Method A (Example 8) 3 = synthesized by Method B (Example 8)
**DCI MS (M + H)+
***formic acid salt
****free amine base TABLE 1-continued Examples 10-34

| Example # | Compound | Epoxide* | m.p. | MS** | Elemental Analysis C / H / N |
|---|---|---|---|---|---|
| 30 | [chroman with 3-butenyl chain, OH, OH, CH₂NH₂] | [epoxide 1, with butenyl] | 203° C. | 278 | calc (¼H₂O): 60.08 / 7.77 / 4.37<br>Found: 60.34 / 7.77 / 4.34 |
| 31 | [chroman with ethyl chain, OH, OH, CH₂NH₂] | [epoxide 1, with ethyl] | 240° C. | 224 | calc: 55.49 / 6.99 / 5.39<br>Found: 55.16 / 6.86 / 5.29 |
| 32 | [chroman with hexyl chain, OH, OH, CH₂NH₂] | [epoxide 1, with hexyl] | 205° C. | 280 | calc (¼H₂O): 59.71 / 8.34 / 4.35<br>Found: 59.41 / 8.14 / 4.25 |
| 33 | [chroman with 4-bromophenyl substituent, OH, OH, CH₂NH₂] | [epoxide 2, 4-bromobenzyl] | 222° C. | 350 | 49.70 / 4.43 / 3.62<br>50.19 / 4.49 / 3.60 |

*1 = commercially available  2 = synthesized by Method A (Example 8)  3 = synthesized by Method B (Example 8)
**DCI MS (M + H)⁺
***formic acid salt
****free base

TABLE 1-continued
Examples 10-34
| Example # | Compound | Epoxide* | m.p. | MS** | Elemental Analysis |||
|---|---|---|---|---|---|---|---|
|  |  |  |  |  | C | H | N |
| 34# | 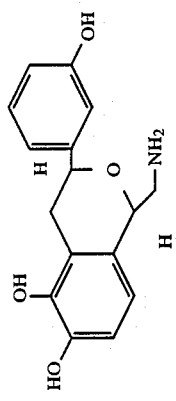 | 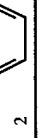 2 | 265° C. | 324 |  |  |  |
*1 = commercially available 2 = synthesized by Method A (Example 8) 3 = synthesized by Method B (Example 8)
**DCI MS (M + H)+
***formic acid salt
****free base
The benzyl protecting group was removed by hydrogenolysis prior to removal of the cyclohexylidene protecting group from the catechol.

EXAMPLE 35

[1R,3S]3-Cyclohexyl-3,4-dihydro-5,6-dihydroxy-1-(n-methyl)-aminomethyl-1H-2-benzopyran hydrochloride

[1R,3S]1-(Aminomethyl)-3-cyclohexyl-5,6-cyclohexylidenedioxy-3,4-dihydro 1H-2-benzopyran (synthesized as described in steps 1 and 2 of Example 9 for [1R,3S]1-aminomethyl-3-t-butyl-5,6-cyclohexylidenedioxy-3,4-dihydro-1H-2-benzopyran) (0.82 g, 2.3 mmol) was dissolved in 25 mL of ethyl formate and heated to reflux temperature. After 1 h at reflux temperature, the reaction mixture was concentrated to a white solid. The solid was dissolved in 15 mL of THF and 175 mg (4.6 mmol) of lithium aluminum hydride (LAH) was added. The reaction mixture was heated at reflux temperature for 3 h then cooled to 0° C. The reaction was quenched by the sequential addition of 0.175 mL of water, 0.175 mL of 15% aqueous sodium hydroxide solution and 0.525 mL of water. The reaction mixture was filtered and the filter cake washed with diethyl ether. The filtrate was concentrated in vacuo. The residue was dissolved in 20 mL of ethanol and the alcohol solution was saturated with anhydrous hydrogen chloride then heated at reflux temperature for 2 h. The ethanol was evaporated down to approximately 2 mL and ether was added until a solid precipitate was formed. The solid was filtered, washed with diethyl ether and dried to give 504 mg (67% yield) of the title compound as a colorless powder, m.p. 244° C. DCI MS: 292 (M+H)+. Analysis calculated for $C_{17}H_{26}ClNO_3$: C, 62.28; H, 7.99; N, 4.27. Found: C, 62.24; H, 7.90; N, 4.21.

EXAMPLE 36

[1R,3S]3-t-Butyl-3,4-dihydro-5,6-dihydroxy-1-(N-methyl)-aminomethyl-1H-2-benzopyran hydrochloride Following the synthesis outlined in Example 35 and starting with [1R,3S]1-aminomethyl-3-t-butyl-5,6-cyclohexylidenedioxy-3,4-dihydro-1H-2 benzopyran, from step 2 of Example 9, Example 36, [1R,3S]3-t-butyl-3,4-dihydro-5,6-dihydroxy-1-(N-methyl)-aminomethyl-1H-2-benzopyran hydrochloride was prepared, m.p. 246° C. DCI MS: 266 (M+H)+. Analysis calculated for $C_{15}H_{23}ClNO_3$: C,59.70; H, 8.00; N, 4.64. Found: C, 59.64; H, 8.10; N, 4.45.

EXAMPLE 37

[1R,3S]1-(N-Allyl)-aminomethyl-3-cyclohexyl-3,4-dihydro-5,6-dihydroxy 1H-2-benzopyran hydrochloride

Step 1

[1R,3S]1-(N-Allyl)-aminomethyl-3-cyclohexyl-5,6-cyclohexylidenedioxy-3,4-dihydro-1H-2-benzopyran

[1R,3S]1-bromomethyl-3-cyclohexyl-5,6-cyclohexylidene dioxy-3,4-dihydro 1H-2-benzopyran (1.1 g, 2.6 mmol), prepared by the procedure outlined in Example 8, using cyclohexyl ethylene oxide (prepared by Method A, Example 8) was dissolved in 10 mL of allylamine. The reaction mixture was heated at reflux temperature for 5 h then concentrated in vacuo. The residue was dissolved in 50 mL of ethyl acetate. The ethyl acetate solution was washed with 2×25 mL of aqueous sodium bicarbonate solution and 1×25 mL of brine, dried over anhydrous sodium sulfate, filtered and concentrated in vacuo. The residue was purified by column chromatography on silica gel eluted with 30% ethyl acetate in hexane to give 928 mq (90% yield) of the title compound as a colorless oil, DCI MS: 398 (M+H)+. $^1$H NMR (CDCl$_3$) delta 1.0–1.9 (m, 20H), 2.05 (bd, 1H, J=11.0 Hz), 2.4 (bs, 1H), 2.5 (dd, 1H, J=13.5, 9.0 Hz), 2.7 (dd, 1H, J=13.5, 2.8 Hz), 2.82 (dd, 1H, J=10.0, 7.5 Hz), 3.18 (dd, 1H, J=10.0, 3.0 Hz), 3.48 (m, 3H), 4.7 (bd, 1H, J=7.5 Hz), 5.2 (m, 2H), 5.95 (m, 1H), 6.5 (d, 1H, J=6.3 Hz), 6.58 (d, 1H, J=6.3 Hz).

Step 2: [1R,3S]1-(N-Allyl) aminomethyl-3-cyclohexyl-3,4-dihydro-5,6-dihydroxy-1H-2-benzopyran hydrochloride

[1R,3S]1-(N-Allyl) aminomethyl-3-cyclohexyl-5,6-cyclohexylidenedioxy-3,4-dihydro-1H-2-benzopyran (920 mg, 2.3 mmol), from Step 1, was dissolved in 15 mL of ethanol saturated with anhydrous hydrogen chloride. The acidic solution was heated at reflux temperature for 2 h then concentrated to approximately 2 mL. Diethyl ether was added until a solid precipitate was formed. The solid was filtered, washed with diethyl ether and dried to give 590 mg (72% yield) of the title compound as an off-white powder, m.p. 217°–219° C. DCI MS: 318 (M+H)+. Analysis calculated for $C_{19}H_{28}ClNO_3$: C, 64.49; H, 7.98; N, 3.96. Found: C, 64.34; H, 8.02; N, 3.82.

EXAMPLES 38–41

Following the syntheses outlined in Example 8 and 37, using the 1 cyclohexyl ethylene oxide and the appropriate alkyl or aryl amine, Examples 38–41 were prepared (as their hydrochloride salts) as disclosed in Table 2. The structure of each was confirmed by melting point, mass spectra and elemental analysis as designated.

TABLE 2
Examples 28–41

| Example # | Compound | Amine | m.p. | MS* | Elemental Analysis C | H | N |
|---|---|---|---|---|---|---|---|
| 38 | (structure: dihydroxy benzopyran with cyclohexyl and cyclopropylaminomethyl substituents) | cyclopropyl-NH₂ | 200° C. | 318 | calc: 64.49  Found: 64.43 | 7.97  8.02 | 3.96  3.88 |
| 39 | (structure: dihydroxy benzopyran with cyclohexyl and benzylaminomethyl substituents) | benzyl-NH₂ | 242° C. | 368 | calc: 68.39  Found: 68.29 | 7.49  7.58 | 3.47  3.38 |
| 40 | (structure: dihydroxy benzopyran with cyclohexyl and phenethylaminomethyl substituents) | phenethyl-NH₂ | 227° C. | 382 | calc: 68.97  Found: 68.73 | 7.72  7.76 | 3.35  3.30 |
| 41 | (structure: dihydroxy benzopyran with cyclohexyl and pyrrolidinylmethyl substituents) | pyrrolidine | 240–242° C. | 332 | calc: 65.29  Found: 65.26 | 8.22  8.26 | 3.81  3.73 |

*DCI MS (M + H)⁺

EXAMPLE 42

[1R,3S]1,3-Bis(aminomethyl)-3,4-dihydro-5,6-dihydroxy-1H-2-benzopyran dihydrochloride

Step 1:

1-Benzyloxy-3-(spiro[(1,3-benzodioxole)-2,1'-cyclohexane]-2-propanol

Glycidol (3.1 g, 42 mmol) was added dropwise to a suspension of sodium hydride (1.0 g, 42 mmol) in 25 mL of dry dimethylformamide (DMF) at 0° C. After stirring the suspension for 30 min at 0° C., 7 1 g (42 mmol) of benzyl bromide was added dropwise and the reaction mixture was stirred at 0° C. for 40 min. The reaction mixture was then diluted with 75 mL of diethyl ether, transferred to a separatory funnel and washed with 2×30 mL of 2 N aqueous sulfuric acid solution, 2×30 mL of water and saturated aqueous sodium bicarbonate solution. The organic solution was dried over anhydrous magnesium sulfate, filtered and concentrated at reduced pressure to give 5.3 g of the protected epoxy alcohol as an oil.

n-Butyl lithium (18.5 mL of a 2.5 M solution in hexane, 46 mmol) was added to a solution of spiro[(1,3-benzodioxole)-2,1'-cyclohexane](7.4 g, 39 mmol) in 75 mL of THF at 0° C. After 4 h, the protected qlycidol (5.3 g, 32 mmol) in 10 mL of THF was added dropwise and the reaction mixture was allowed to warm to ambient temperature. After 1.5 h, the reaction mixture was poured into 10% aqueous ammonium chloride solution and extracted with 2×50 mL of diethyl ether. The combined ether extracts were washed with ammonium chloride solution, dried over anhydrous magnesium sulfate, filtered and concentrated in vacuo. The residue was purified by column chromatography on silica gel eluted with 20% ethyl acetate in hexane to give 4.4 g (38% yield) of the title compound as a colorless oil. DCI MS: 372 $(M+NH_4)^+$, 355 $(M+H)^+$. $^1H$ NMR (CDCl$_3$) delta 1.4–1.9 (m, 10H), 2.46 (d, 1H, J=3.9 Hz), 2.79 (d, 2H, J=7.0 Hz), 3.4 (dd, 1H, J=9.9, 7.2 Hz), 3.52 (dd, 1H, J=9.9, 3.0 Hz), 4.12 (m, 1H), 4.54 (s, 2H), 6.6–6.73 (m, 3H), 7.34 (m, 5H).

Step 2:
[1R,3S]3-Benzyloxymethyl-1-bromomethyl-5,6-cyclohexylidenedioxy-3,4-dihydro 1H-2-benzopyran A solution of 1-benzyloxy 3-(spiro[(1,3-benzodioxole)-2,1'-cyclohexane])-2-propanol (4.3 g, 12 mmol), from Step 1, and bromoacetaldehyde dimethyl acetal (1.7 mL, 14 mmol) in 25 mL of methylene chloride was cooled to 0° C. Boron trifluoride etherate (3.6 mL, 29 mmol) was added dropwise and the reaction mixture was stirred for 1.5 h. The resultant dark brown solution was poured into 50 mL of 10% aqueous sodium carbonate solution and the aqueous solution was extracted with 3×50 mL of diethyl ether. The combined ether extracts were washed with saturated aqueous sodium bicarbonate solution and brine, dried over anhydrous magnesium sulfate, filtered and concentrated under reduced pressure. The residue was purified by column chromatography on silica qel eluted with 20% ethyl acetate in hexane to give 4.2 g (75%) of the title compound as a colorless syrup. DCI MS: 476 $(M+NH_4)^+$. $^1H$ NMR (CDCl$_3$) delta 1.45–1.95 (m, 10H), 2.57 (dd, 1H, J=16.5, 11.4 Hz), 2.71 (dd, 1H, J=16.5, 3 Hz), 3.59 (dd, 1H, J=11.4, 6 Hz), 3.63 (dd, 1H, J=10.8, 4.2 Hz), 3.73 (dd, 1H, J=10.8, 6 Hz), 3.87 (dd, 1H, J=11.4, 2.7), 4.65 (d, 1H, J=12 Hz), 4.72 (d, 1H, J=12 Hz), 5.0 (m, 1H), 6.52 (d, 1H, J=8.4 Hz), 6.62 (d, 1H, J=8.4 Hz), 7.25–7.42 (m, 5H).

Step 3:
[1R,3S]1-Bromomethyl-5,6-cyclohexylidenedioxy-3,4-dihydro-3-hydroxymethyl-1H-2-benzopyran 5% Platinum on carbon (1.0 g) was added to a solution of [1R,3S]3-benzyloxymethyl-1-bromomethyl 5,6-cyclohexylidenedioxy 3,4-dihydro-1H-2-benzopyran (4.0 g, 8.7 mmol), from Step 2, in 150 mL of methanol and 5 mL of ethyl acetate. The reaction mixture was sealed under 4 atmospheres of hydrogen and shaken overnight. The reaction mixture was filtered to remove the catalyst and concentrated to a light brown oil. The oil was purified by column chromatography on silica gel eluted with 30% ethyl acetate in hexane to give 2.2 g (68% yield) of the title compound as a white foam. $^1H$ NMR (CDCl$_3$) delta 1.4–1.95 (m, 10H), 2.25 (dd, 1H, J=8.4, 4.5 Hz), 2.62 (d, 2H, J=7.5 Hz), 3.57 (dd, 1H, J=11.4, 6.9 Hz), 3.65–3.9 (m, 4H), 4.98 (m, 1H), 6.52 (d, 1H, J=8.4 Hz), 6.63 (d, 1H, J=8.4 Hz).

Step 4:
[1R,3S]1-Azidomethyl-5,6-cyclohexylidenedioxy-3,4-dihydro-3-hydroxymethyl-1H-2 benzopyran Lithium azide (1.0 g, 20 mmol) was added to a solution of [1R,3S]1-bromomethyl 5,6-cyclohexylidenedioxy-3,4-dihydro-3 hydroxymethyl-1H-2-benzopyran (2.17 g, 5.87 mmol), from Step 3, in 20 mL of DMF. The reaction mixture was heated to 70° C. for 1.5 h then cooled to ambient temperature and poured into 50 mL of diethyl ether and 50 mL of water. The layers were separated and the aqueous layer was extracted with 2×50 mL of diethyl ether. The combined ether layers were washed with saturated aqueous sodium bicarbonate solution, dried over anhydrous magnesium sulfate, filtered and concentrated in vacuo. The residue was purified by column chromatography on silica gel eluted with 25% ethyl acetate in hexane to give 1.38 g (70% yield) of the title compound as a colorless glass. $^1H$ NMR (CDCl$_3$) delta 1.45–1.95 (m, 10H), 2.14 (dd, 1H, J=9.0, 4.8 Hz), 2.63 (d, 2H, 7.5 Hz), 3.5 (dd, 1H, J=13.5, 7.0 Hz), 3.62 (dd, 1H, J=13.5, 2.7 Hz), 3.65–3.9 (m, 3H), 5.02 (m, 1H), 6.45 (d, 1H, J=8.4 Hz), 6.61 (d, 1H, J=8.4 Hz).

Step 5: [1R,3S]1,3-Bis(azidomethyl)-5,6 cyclohexylidenedioxy-3,4-dihydro-1H-2-benzopyran Methanesulfonyl chloride (0.128 mL, 1.65 mmol) was added dropwise to a solution of [1R,3S]1-azidomethyl-5,6-cyclohexylidenedioxy-3,4-dihydro-3-hydroxymethyl-1H-2-benzopyran (500 mg, 1.5 mmol), from Step 4, and 0.314 mL (2.25 mmol) of triethylamine (TEA) in 15 mL of methylene chloride at 0° C. After stirring for 30 min at 0° C., the reaction mixture was transferred to a separatory funnel and diluted with diethyl ether. The layers were separated and the organic layer was washed with 2×20 mL of water, 2×15 mL of 1 N aqueous hydrochloric acid solution and brine, dried over magnesium sulfate, filtered and concentrated under reduced pressure to yield a white foam. The foam was dissolved in 20 mL of DMF and 440 mg (9 mmol) of lithium azide was added. The reaction mixture was heated to 80° C. and stirred at 80° C. for 4 h then cooled and poured into 50 mL of water. The aqueous solution was extracted with 3×30 mL of diethyl ether and the combined ether extracts were washed with 30 mL of water and brine , dried over anhydrous magnesium sulfate and concentrated under reduced pressure. The residue was purified on silica qel eluted with diethyl ether to give 450 mg (84% yield) of the title compound as a pale yellow oil. DCI MS: 374 $(M+NH_4)^+$. $^1H$ NMR (CDCl$_3$) delta 1.45–1.95 (m, 10H), 2.67 (m, 2H), 3.38 (dd, 1H, J=13 5, 3.9 Hz), 3.5 (m, 2H), 3.7 (dd, 1H, J=13.5, 2.7 Hz), 3.9 (m, 1H), 5.0 (m, 1H), 6.47 (d, 1H, J=8.7 Hz), 6.62 (d, 1H, J=8.7 Hz).

Step 6: [1R,3S]1,3-Bis(aminomethyl) 5,6-cyclohexylidenedioxy-3,4-dihydro 1H-2-benzopyran Lithium aluminum hydride (2.4 mL of a 1.0 M solution in diethyl ether, 2.4 mmol) was added dropwise to a solution of [1R,3S]1,3-bis(azidomethyl)-5,6-cyclohexylidenedioxy-3,4 dihydro-1H-2-benzopyran (430 mg, 1.2 mmol), from Step 5, in 10 mL of anhydrous diethyl ether at 0° C. The reaction mixture was allowed to warm to ambient temperature and stirred for 45 min.

The reaction was then quenched by the sequential addition of 0.091 mL of water, 0.091 mL of 15% aqueous sodium hydroxide solution and 0.273 mL of water. The solution was dried over anhydrous magnesium sulfate, filtered and concentrated in vacuo to give 212 mg (85% yield) of the title compound as a colorless glass. $^1$H NMR (CDCl$_3$) 1.4–1.95 (m, 14H), 2.5 (dd, 1H, J=17.1, 11.4 Hz), 2.65 (dd, 1H, J=17.1, 3 Hz), 2.9 (m, 2H), 3.0 (dd, 1H, J=13.8, 6 Hz), 3.21 (dd, 1H, J=13.8, 2.4 Hz), 3.66 (m, 1H), 4.7 (m, 1H), 6.51 (d, 1H, J=8.4 Hz), 6.61 (d, 1H, J=8.4 Hz).

Step 7:
[1R,3S]1,3-Bis(aminomethyl)-3,4-dihydro-5,6-dihydroxy-1H-2-benzopyran dihydrochloride Absolute ethyl alcohol (10 mL) was saturated with anhydrous hydrogen chloride and added to 312 mg (0.96 mmol) of [1R,3S]1,3-bis(aminomethyl)-5,6-cyclohexylidenedioxy-3,4-dihydro-1H-2-benzopyran from Step 6. The solution was heated to reflux temperature. After 45 min at reflux temperature, a precipitate formed. The volume of the reaction mixture was reduced to 5 mL and diethyl ether was added until precipitation was complete. The precipitate was collected by vacuum filtration and the solid was washed with diethyl ether and dried in a vacuum oven at 80° C. overnight to give 280 mg (96% yield) of the title compound as a fine white powder, m.p. >260° C. IR 3320, 3040, 1590, 1500, 1290 cm$^{-1}$. DCI MS: 225 (M+H)$^+$. $^1$H NMR (d$_6$-DMSO) delta 2.38 (dd, 1H, J=16.5, 12 Hz), 2.76 (m, 2H), 2.97 (m, 1H), 3.52 (m, 2H), 3.9 (m, 1H), 4.83 (m, 1H), 6.54 (d, 1H, 8.1 Hz), 6.7 (d, 1H, J=8.1 Hz), 8.25 (bs, 6H), 8.6 (s, 1H), 9.4 (s, 1H). Analysis calculated for C$_{11}$H$_{18}$Cl$_2$N$_2$O$_3$: C, 44.46; H, 6.11; N, 9.43. Found: C, 44.70; H, 6.04; N, 9.22.

EXAMPLE 43

[1R,3S]1-Aminomethyl-3,4-dihydro-5,6-dihydroxy-3-hydroxymethyl-1H-2-benzopyran hydrochloride Step 1: [1R,3S]1-Aminomethyl-5,6 cyclohexylidenedioxy-3,4-dihydro-3-hydroxy-methyl-1H-2-benzopyran Lithium aluminum hydride (1.1 mL of 1.0 M solution in diethyl ether, 1.1 mmol) was added dropwise to a solution of 370 mg (1.1 mmol) of [1R,3S]1-azidomethyl-5,6-cyclohexylidenedioxy 3,4-dihydro-3-hydroxymethyl-1H-2-benzopyran, the product of Step 4 of Example 42, in 10 mL of anhydrous diethyl ether at 0° C. The reaction mixture was allowed to warm to ambient temperature and stirred for 40 min. The reaction mixture was cooled to 0° C. and quenched by the sequential addition of 0.042 mL of water, 0.042 mL of 15% aqueous sodium hydroxide solution and 0.126 mL of water. The solution was dried over anhydrous magnesium sulfate and filtered. The filtrate was concentrated in vacuo to give 263 mg (77% yield) of the title compound as a white powder. DCI MS: 306 (M+H)$^+$. $^1$H NMR (CDCl3) delta 1.4-1.95 (m, 13H), 2.6 (m, 2H), 3.03 (dd, 1H, J=13.5, 5.7 Hz), 3.23 (dd, 1H, J=13.5, 2.7 Hz), 3.7 (dd, 1H, J=11.7, 7.5 Hz), 3.77–3.9 (m, 2H), 4.74 (m, 1H), 6.52 (d, 1H, J=8.4 Hz), 6.62 (d, 1H, J=8.4 Hz).

Step 2
[1R,3S]1-Aminomethyl-3,4-dihydro-5,6-dihydroxy-3-hydroxymethyl 1H-2-benzopyran hydrochloride Absolute ethyl alcohol (8 mL) was saturated with anhydrous hydrogen chloride and added to a suspension of 256 mg (0.83 mmol) of [1R,3S]1-aminomethyl-5,6-cyclohexylidenedioxy-3,4-dihydro-3-hydroxymethyl-1H-2-benzopyran from Step 1 in 2 mL of ethanol. The reaction mixture was heated to reflux temperature. After 1.5 h at reflux temperature, a precipitate had formed. The solvent was evaporated under reduced pressure to approximately 5 mL. Diethyl ether was added until the precipitation was complete and the solid was collected by vacuum filtration, washed with diethyl ether and dried in a vacuum oven at 80° C. overnight to give 160 mg (73% yield) of the title compound as an off white powder, m.p. 235° C. IR 3200, 1590, 1500, 1295, 1050 cm$^{-1}$. DCI MS: 226 (M+H)$^+$. $^1$H NMR (d$_6$-DMSO) delta 2.28 (dd, 1H, J=16.8, 11.4 Hz), 2.66 (dd, 1H, J=16.8, 3.0 Hz), 2.83 (dd, 1H, J=12.3, 9.3 Hz), 3.45–3.7 (m, 4H), 4.8 (m, 2H), 6.51 (d, 1H, J=8.4 Hz), 6.67 (d, 1H, J=8.4 Hz), 8.05 (bs, 3H), 8.48 (bs, 1H), 9.3 (bs, 1H). Analysis calculated for C$_{11}$H$_{16}$C1NO$_4$: C, 50.48; H, 6.16; N, 5.35. Found: C, 50.64; H, 6.24; N, 5.20.

EXAMPLE 44

[1R,3S]1-Aminomethyl-3-cyclohexyl-6,7-dihydroxy-1,3,4,5-tetrahydro-2-benzoxepin hydrochloride Step 1:
Spiro[(4-methyl-1,3-benzodioxole)-2,1'-cyclohexane]

A catalytic amount of p-toluenenesulfonic acid (approximately 50 mg) was added to a solution of 2,3 dihydroxytoluene (10 g, 80.7 mmol) and cyclohexanone (8.3 mL, 81 mmol) in 150 mL of cyclohexane. The reaction mixture was heated to reflux temperature and the water produced in the condensation reaction was removed using a Dean Stark trap. After 6 h, the solution was concentrated to approximately 50 mL and purified on a silica gel column (10 cm×6 cm) eluted with hexane, to give the title compound (14 g) as a colorless liquid. $^1$H NMR (CDCl$_3$) delta 1.5 (m, 2H), 1.7 (m, 4H), 1.9 (m, 4H), 2.2 (s, 3H), 6.6 (m, 3H).

Step 2: 1-Cyclohexyl-2-(2', 3'-cyclohexylidenedioxy-4'-methylphenyl) ethanol and 1-Cyclohexyl-3-(2',3'-cyclohexylidenedioxyphenyl)-1-propanol n-Butyl lithium (23 mL of a 2.1 M solution in hexane, 49 mmol) was added dropwise to a solution of spiro[(4 methyl-1,3-benzodioxole)-2,1'-cyclohexane](9 g, 44 mmol), from Step 1, in 60 mL of THF at 0° C. The reaction mixture was allowed to warm to 25° C. and stirred at ambient temperature for 4 h. The reaction mixture was then cooled to 0° C. and 1 cyclohexylethylene oxide was added. The reaction mixture was stirred for 2 h at 25° C. and 30 min at 50° C. then poured into 100 mL of saturated aqueous ammonium chloride solution and extracted with 3× 100 mL of diethyl ether. The combined ether extracts were washed with water and brine, dried over anhydrous maqnesium sulfate, filtered and concentrated in vacuo. The title compounds were separated by column chromatography on silica gel eluted with 5% ethyl acetate in hexane to give 5.12 g (35% yield) of 1-cyclohexyl-2-(2',3'-cyclohexylidenedioxy-4'-methylphenyl) ethanol and 3.63 g (25% yield) of 1-cyclohexyl-3-(2',3'-cyclohexylidenedioxyphenyl)-1-propanol.

Step 3:
[1R,3S]1-Bromomethyl-3-cyclohexyl-6,7-cyclohexylidenedioxy-1,3,4,5-tetrahydro-2-benzoxepin hydrochloride Boron trifluoride etherate (1.47 mL, 12 mmol) was added dropwise to a solution of 2 g (6.06 mmol) of 1-cyclohexyl-3-(2',3'-cyclohexylidenedioxyphenyl)-1-propanol from Step 2 and bromoacetaldehyde dimethyl acetal (0.716 mL, 6.06 mmol) in 30 mL of methylene chloride at −20° C. The temperature of the reaction mixture was maintained between −10° C. and −5° C. for 1 h. The reaction mixture was then diluted with 100 mL of diethyl ether and washed with 2×50 mL of aqueous sodium carbonate solution and 50 mL of brine. The organic solution was dried over anhydrous magnesium sulfate, filtered and concentrated in vacuo. The residue was purified by column chromatography on silica gel eluted with 2% ethyl acetate in hexane to give 1.2 g (46% yield) of the title compound as a colorless foam.

Step 4:
[1R,3S]1-Aminomethyl-3-cyclohexyl-6,7-cyclohexylidenedioxy-1,3,4,5-tetrahydro-2-benzoxepin Lithium azide (590 mg, 12 mmol) was added to a solution of 1.05 g (2.4 mmol) of [1R,3S]1-bromomethyl-3-cyclohexyl- 6,7-cyclohexylidenedioxy-1,3,4,5-tetrahydro-2- benzoxepin, from Step 3, in 10 mL of DMF at 25° C. The reaction mixture was heated to 65° C., stirred at 65° C. for 2.5 h, cooled to ambient temperature and poured into 100 mL of water. The aqueous solution was extracted with 3×50 mL of diethyl ether. The combined ether extracts were washed with 75 mL of water and 75 mL of brine, dried over anhydrous maqnesium sulfate, filtered and concentrated in vacuo. The residue was purified by column chromatography on silica gel eluted with 2% ethyl acetate in hexane to give 850 mg (89% yield) of [1R,3S]1-azidomethyl-3-cyclohexyl-6,7-cyclohexylidenedioxy-1,3,4,5-tetrahydro-2-benzoxepin. This azide intermediate was dissolved in 25 mL of diethyl ether and lithium aluminum hydride (2.1 mL of a 1 M solution in diethyl ether) was added to the solution at 0° C. After warming the reaction mixture to ambient temperature and stirring for 1 h, the reaction mixture was cooled to 0° C. and the reaction quenched by the sequential addition of 0.08 mL of water, 0.08 mL of 15% aqueous sodium hydroxide solution and 0.24 mL of water. The precipitate was filtered and washed with diethyl ether. The filtrate was concentrated and the residue redissolved in diethyl ether. The ether solution was treated with diethyl ether saturated with anhydrous hydrogen chloride. The precipitate was collected by vacuum filtration and dried to give 770 mg (90% yield) of the title compound as a colorless solid, m.p. 250° C. DCI MS :372 (M+H)+. 1H NMR (CDCl3) delta 0.9–1.9 (m, 23H), 2.7 (m, 1H), 3.02 (m, 1H), 3.3 (t, 1H, J=11.4 Hz), 3.52 (m, 2H), 4.97 (dd, 1H, J=11.4, 2.9 Hz), 6.45 (d, 1H, J=7.5 Hz), 6.5 (d, 1H, J=7.5 Hz), 8.5 (bs, 2H).

Step 5:
[1R,3S]1-Aminomethyl-3-cyclohexyl-6,7-dihydroxy-1,3,4,5-tetrahydro-2-benzoxepin hydrochloride

[1R,3S]1-Aminomethyl-3-cyclohexyl-6,7-cyclohexylidenedioxy-1,3,4,5-tetrahydro-2-benzoxepin hydrochloride (200 mg, 0.49 mmol), from Step 4, was added to a 1N solution of anhydrous hydrochloric acid in ethyl alcohol. The reaction mixture was heated to 50° C. and monitored by TLC analysis. After 2 h the solution was concentrated to approximately 1 mL and the residue triturated with diethyl ether. The solid was collected by vacuum filtration, washed with diethyl ether and dried to give 62 mg (40% yield) of the title compound as a colorless powder, m.p. 216°–219° C. DCI MS: 292 (M+H)+. Analysis calculated for $C_{17}H_{26}ClNO_3$: C, 62.28; H, 7.99; N, 4.27. Found: C, 62.22; H, 8.05; N, 4.14.

EXAMPLE 45
[1R,3S]1-Aminomethyl-3-cyclohexyl-3,4-dihydro-5,6-dihydroxy-7-methyl-1H-2-benzopyran hydrochloride 1-Cyclohexyl-2-(2',3'-cyclohexylidenedioxy-4'-methylphenyl) ethanol, from Step 1 of Example 44, was converted to the title compound by the procedures described in Example 44 above, Steps 3–5, m.p. 168°–170° C. DCI MS: 292 (M+H)+. Analysis calculated for $C_{17}H_{26}ClNO_3 + \frac{1}{2}H_2O$: C, 60.61; H, 8.077; N, 4.16. Found: C, 60.39; H, 7.92; N, 4.12.

EXAMPLE 46
[1S*,3R*]1-Aminomethyl-3,4-dihydro-5,6-dihydroxy-3-phenyl-1H-2-benzopyran hydrochloride

Step 1: 2-(2',3'-cyclohexylidenedioxyphenyl)-1-phenyl ethanone

A solution of 15.5 g (50 mmol) of 2-(2',3'-cyclohexylidenedioxyphenyl)-1-phenylethanol prepared from styrene oxide (commercially available from Aldrich Chemical Company) by the procedure described in Step 2 of Example 8, in 60 mL of methylene chloride was added dropwise to a mixture of 60 g (28 mmol) of pyridinium chlorochromate (PCC) and 35 g of Celite filter aid in 300 mL of methylene chloride. at ambient temperature. After 4 h, the reaction mixture was diluted with 200 mL of diethyl ether and filtered through silica gel. The chromium containing residue was washed several times with diethyl ether. The filtrate was concentrated under reduced pressure to give 14 g (90% yield) of the title compound as a yellow syrup. DCI MS: 326 (M+NH4)+, 309 (M+H)+. 1H NMR (CDCl3) delta 1.4–1.9 (m, 10H), 4.2 (s, 2H), 6.7 (m, 3H), 7.42 (m, 2H), 7.53 (m, 1H), 8.05 (m, 2H).

Step 2: [1R*]2-(2,3'-cyclohexylidenedioxyphenyl)-1-phenylethanol

A solution of 754 mg (2.45 mmol) of 2-(2',3'-cyclohexylidenedioxyphenyl)-1-phenylethanone, from Step 1, in 1 mL of THF was added to a solution of 936 mg (2.9 mmol) of (+) B-chlorodiisopinocampheylborane (commercially available from Aldrich Chemical Company) in 3 mL of THF at −20° C. After storing the resultant solution for 12 h at −15° C., the solvent was evaporated, the residue was dissolved in 15 mL of diethyl ether and 565 mg of diethanolamine was added. The mixture was stirred for 30 min. The precipitate was removed by filtration through Celite filter aid. The filtrate was concentrated and the residue purified by column chromatography on silica gel eluted with methylene chloride:hexane:diethyl ether (100:20:1) to give 546 mg (72% yield) of the title compound. DCI MS: 328 (M+NH4)+. 1H NMR (CDCl3) delta 1.4–1.9 (m, 10H), 2.3 (bs, 1H), 3.0 (m, 2H), 4.98 (dd, 1H, J=7.5, 5.0 Hz), 6.62 (m, 3H), 7.3 (m, 5H).

Step 3: [1S*, 3R*]1-Aminomethyl-3,4-dihydro-5,6-dihydroxy-3-phenyl 1H-2-benzopyran hydrochloride

[1R*]2-(2',3'-Cyclohexylidenedioxyphenyl)-1-phenylethanol was converted to [1S*, 3R*]1-aminomethyl-3,4-dihydro-5,6-dihydroxy-3-phenyl 1H-2-benzopyran hydrochloride by the procedures detailed in Step 3 of Example 8 and Steps 1–3 of Example 9, m.p. 158°–160° C. [alpha]$_D$=+110° (C=0.52, 1N HCl), DCI MS 272 (M+H)+. Analysis calculated for $C_{16}H_{18}ClNO_3$ C, 60.60; H, 6.05; N, 4 42. Found C, 60.71; H, 6.2; N, 4.31.

EXAMPLE 47

[1R,3S]1-Aminomethyl-3,4-dihydro-5,6-dihydroxy-3-pyrrolidinomethyl-1H-2-benzopyran dihydrochloride

Step 1: [1R,3S]1-Azidomethyl-5,6-cyclohexylidenedioxy-3,4-dihydro-3-pyrrolidinomethyl-1H-2-benzopyran Methanesulfonyl chloride (0.146 mL, 1.89 mmol) was added dropwise to a solution of 0.57 g (1.72 mmol) of [1R,3S]1-azidomethyl-5,6-cyclohexylidenedioxy-3,4-dihydro-3-hydroxymethyl-1H-2-benzopyran, the product of Step 4 of Example 42, and 0.36 mL (2.58 mmol) of triethylamine in 15 mL of methylene chloride at 0° C. The reaction mixture was stirred for 30 min at 0° C. then transferred to a separatory funnel and diluted with 45 mL of diethyl ether. The layers were separated and the organic layer was washed with 2×20 mL of water, 2×20 mL of 1 N hydrochloric acid and 20 mL of brine, dried over anhydrous magnesium sulfate , filtered and concentrated under reduced pressure to give 405 mg of white foam. The foam was dissolved in 20 mL of dimethyl formamide (DMF) and an excess amount of pyrrolidine was added to this solution. The reaction mixture was heated at 95° C. for 2.5 h then poured into 75 mL of water. The aqueous solution was extracted with 3×40 mL of diethyl ether. The combined ether extracts were washed with 2×30 mL of water and brine, dried over anhydrous magnesium sulfate and concentrated in vacuo. The residue was purified by column chromatography on silica gel eluted with 10% methanol in methylene chloride to give 210 mg (55% yield) of the title compound as a white foam. DCI MS: 385 (M+H)+. $^1$H NMR (CDCl$_3$) delta 1.4–1.9 (m, 14H), 2.5–2.9 (m, 8H), 3.45 (dd, 1H, J=13.2, 6.6 Hz), 3.68 (dd, 1H, J=13.2, 2.4 Hz), 3 9 (m, 1H), 4.97 (m, 1H), 6.45 (d, 1H, J=8.1 Hz), 6.6 (d, 1H, J=8.1 Hz).

Step 2: [1R,3S]1-Aminomethyl-5,6-cyclohexylidenedioxy-3,4-dihydro-3-pyrrolidinomethyl-1H-2-benzopyran Lithium aluminum hydride (0.52 mL of a 1.0 M solution, 0.52 mmol) was added dropwise to a solution of 20 mg (0.52 mmol) of [1R,3S]1-azidomethyl-5,6-cyclohexylidenedioxy-3,4-dihydro-3-pyrrolidinomethyl-1H-2-benzopyran, from Step 1, in 10 mL of anhydrous diethyl ether at 0° C. The reaction mixture was allowed to warm to ambient temperature and it was stirred at ambient temperature for 40 min. The reaction mixture was then cooled to 0° C. and quenched by the sequential addition of 0.020 mL of water, 0.020 mL of 15% aqueous sodium hydroxide solution and 0.060 mL of water. The resultant solution was dried over anhydrous magnesium sulfate and the precipitate filtered. Diethyl ether saturated with anhydrous hydrogen chloride was then added dropwise to the filtrate to precipitate the hydrochloride salt of [1R,3S]1-aminomethyl-5,6 -cyclohexylidinedioxy-3,4-dihydro 3 pyrrolidinomethyl-1H-2-benzopyran which was collected by vacuum filtration yielding 220 mg (98%) of the title compound as its hydrochloride salt, a white solid. DCI MS: 359 (M+H)+.

Step 3: [1R,3S]1-Aminomethyl-3,4-dihydro-5,6-dihydroxy-3-pyrrolidinomethyl-1H-2-benzopyran dihydrochloride Absolute ethanol (10 mL) was saturated with anhydrous hydrogen chloride and added to 187 mg (0.44 mmol) of the product of Step 2, [1R,3S]1-aminomethyl-3,4 dihydro-5,6-cyclohexylidenedioxy-3-pyrrolidinomethyl-1H-2-benzopyran. The reaction mixture was heated to reflux temperature. After 2 h at reflux temperature, a precipitate formed and the reaction mixture was cooled to ambient temperature. The volume of the reaction mixture was reduced under reduced pressure to approximately 5 mL. Diethyl ether was added to the concentrate to precipitate the product which was collected by vacuum filtration and washed with diethyl ether. The solid was dried in a vacuum oven at 80° C. overnight to give 146 mg (96% yield) of the title compound as a fine white powder, m.p.>280° C. IR 3400, 3200, 2960, 1510, 1295 cm$^{-1}$. DCI MS: 279 (M+H)+. $^1$H NMR (d$_6$-DMSO) delta 2.0 (m, 4H), 2.33 (dd, 1H, J=16.2, 10.8 Hz), 2.75 (m, 2H), 3.1 (m, 2H), 3.4 (m, 2H), 3.6 (m, 3H), 4.05 (m, 1H), 4.93 (m, 1H), 6.54 (d, 1H, J=8.7 Hz), 6.7 (d, 1H, J=8.7 Hz), 8.4 (bs, 3H), 8.6 (s, 1H), 9.4 (s, 1H), 10.6 (bs, 1H).

Analysis calculated for $C_{15}H_{24}Cl_2N_2O_3$: C, 51.29; H, 6.89; N, 7.97. Found: C, 50.94; H, 6.82; N, 7.76.

EXAMPLES 48–49

Following the syntheses outlined in Example 47, using 3-(benzyloxy)propylene oxide and the appropriate alkyl or cycloalkyl amine, Examples 48–49 were prepared as disclosed in Table 3, as their dihydrochloride salts. The structure of each was confirmed by melting point, mass spectra and elemental analysis as designated.

TABLE 3

Examples 48–49

| Example # | Compound | Amine | m.p. | MS* | Elemental Analysis C | H | N |
|---|---|---|---|---|---|---|---|
| 48 | 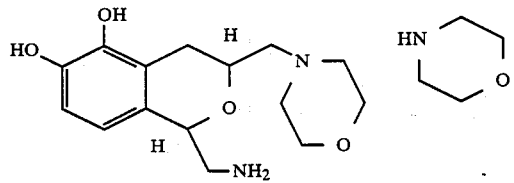 | 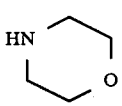 | 255° C. | 295 | calc: 49.06<br>Found: 49.05 | 6.59<br>6.68 | 7.63<br>7.42 |

TABLE 3-continued

Examples 48-49

| Example # | Compound | Amine | m.p. | MS* | Elemental Analysis C | H | N |
|---|---|---|---|---|---|---|---|
| 49 | (structure: HO, OH on phenyl ring fused to tetrahydronaphthalene with H, CH2-N-piperidine substituent, and O-CH(H)-CH2-NH2 linker) | piperidine (HN-piperidine) | 265° C. | 293 | calc: 52.61  Found: 52.80 | 7.17  7.21 | 7.67  7.53 |

*DCI MS (M + H)+

EXAMPLE 50

[1R,3S]-5,6-Dihydroxy-3-phenyl-1-(2'R-pyrrolidino)-1,2,3,4-tetrahydro-naphthalene hydrobromide

Step 1: 1-Cyano-3,4-dihydro 5,6-dimethoxy 3-phenyl-naphthalene

To a suspension of 10 g (35 mmol) of 5,6-dimethoxy-3-phenyl 1,2,3,4-tetrahydro 1-naphthalenone, the product of Example 1, was added 7.5 g (75.6 mmol) of trimethylsilyl cyanide (commercially available from Aldrich Chemical Company) and approximately 50 mg of anhydrous aluminum chloride (AlCl3). The reaction mixture was heated at 60° C. for 3 h then cooled to ambient temperature and diluted with 150 mL of toluene. The volume of the reaction mixture was reduced in vacuo to approximately 50 mL. The resultant trimethylsilyl adduct was dehydrated by treatment with 15 mL of trifluoroacetic acid and 100 mg of p toluene sulfonic acid in 200 mL of toluene at reflux temperature for 1 h. The reaction mixture was cooled to ambient temperature, the layers separated and the organic layer washed with water, aqueous sodium bicarbonate solution and brine, dried over anhydrous magnesium sulfate, filtered and concentrated under reduced pressure to give a colorless oil. The oil was purified by column chromatography on silica gel eluted with 20% ethyl acetate in hexane to give 8.5 g (83% yield) of the title compound, m.p. 109°–110° C.

Step 2: 1-Cyano-5,6-dimethoxy-3-phenyl-1,2,3,4-tetrahydro-naphthalene

Sodium borohydride (6.8 g) was added to a suspension of 6.8 g (23.3 mmol) of 1-cyano-3,4-dihydro-5,6-dimethoxy-3-phenyl naphthalene, from Step 1, in 100 mL of absolute ethanol and the reaction mixture was heated at reflux temperature for 1.5 h. The solvent was evaporated under reduced pressure and the residue was dissolved in ethyl acetate. The ethyl acetate solution was washed with 1N aqueous hydrochloric acid solution, aqueous sodium bicarbonate solution and brine, dried over anhydrous magnesium sulfate, filtered and concentrated to an oil. The oil was "triturated" with heptane to give 5.63 g (82%) yield of the title compound as a white crystalline solid, m.p. 118°–121° C.

Step 3: 5,6-Dimethoxy-3-phenyl-1,2,3,4-tetrahydro-1-naphthalene carboxylic acid A mixture of 5.6 g (19.1 mmol) of 1-cyano-5,6-dimethoxy-3-phenyl-1,2,3,4-tetrahydro-naphthalene, from Step 2, 40 mL of 5% aqueous potassium hydroxide solution and 90 mL of ethylene glycol was heated at reflux temperature for 8 h. The reaction mixture was then cooled to −20° C. and made acidic by the addition of cold concentrated aqueous hydrochloric acid solution. The acidic solution was extracted with methylene chloride and the organic extracts were washed with brine, dried over anhydrous magnesium sulfate, filtered and evaporated to give 5 g (84% yield) of the title compound which was used in the next step without purification.

Step 4: N-Methoxy-N-methyl-5,6-dimethoxy-3-phenyl-1,2,3,4-tetrahydro-1-naphthalene carboxamide 5,6-Dimethoxy-3-phenyl-1,2,3,4-tetrahydro 1-naphthalene carboxylic acid (5 g, 16 mmol), from Step 3, was suspended in 100 mL of toluene and 5 mL of oxalyl chloride was added. The reaction mixture was heated at reflux temperature for 1.5 h under a nitrogen atmosphere. The solvent was evaporated and the water removed from the residue as an azeotrope with toluene (2×40 mL). The acid chloride and 2 g (20 mmol) of N,O-dimethylhydroxylamine hydrochloride were dissolved in 80 mL of ethanol free chloroform. The solution was cooled to 0° C. and 3.3 mL of pyridine was added slowly. The reaction mixture was allowed to warm to ambient temperature and stirred at ambient temperature for approximately 4 h then evaporated to dryness. The residue was dissolved in a 1:1 mixture of diethyl ether and methylene chloride and washed with brine. The layers were separated and the organic layer dried over magnesium sulfate, filtered and concentrated under reduced pressure to give the title compound as an oil in 98% yield. The product of Step 4 was used in the next step without purification.

Step 5: 5,6-Dimethoxy-3-phenyl-1-(2'-pyrrolidino)-1,2,3,4-tetrahydro-naphthalene hydrochloride N-Methoxy-N-methyl-5,6-dimethoxy-3-phenyl-1,2,3,4-tetrahydro-1-naphthalene carboxamide (3.3 g, from Step 4, was dissolved in 80 mL of dry THF and the solution was cooled to 0° C. An excess (3–4 equivalents) of 2,2,5,5 tetramethyl-1-aza-2,5-disilacyclopentane-1-propyl magnesium bromide was added and stirred overnight. 2,2,5,5-Tetramethyl-1-aza-2,5-disilacyclopentane-1-propyl magnesium bromide was prepared as described by Basha and DeBernardis in *Tetrahedron Letters*, 25, 5271–5274 (1984). The reaction mixture was recooled to 0° C., 10% hydrochloric acid solution in ethanol was added to it slowly, and it was allowed to warm to ambient temperature again. The reaction mixture was stirred at ambient temperature for 3 h and the solvent was evaporated. The residue was dissolved in 50 mL of methanol, cooled to 0° C. and treated with an excess of sodium cyanoborohydride. The reaction mixture was allowed to warm to ambient temperature and stirred at ambient temperature for 2 h. The solvent was removed in vacuo and the residue was dissolved in diethyl ether and washed with water. The layers were separated and the acidic aqueous layer was made basic and extracted with methylene chloride. The methylene chloride extract was dried over anhydrous magnesium sufate, filtered and concentrated in vacuo. The residue was purified by column chromatography on silica gel eluted with ethyl acetate:formic acid:water (18:1:1) to give a total yield, after concentration in vacuo, of 2.42 g (42% yield) of the title compound as individual diastereomers as their formate salts. Each diastereomer was converted to its hydrochloride salt as follows: The formate salt was dissolved in water and the aqueous solution was made basic with sodium hydroxide. The free base was extracted with methylene chloride, and the organic layer was washed with brine, dried over anhydrous magnesium sulfate, filtered and concentrated under reduced pressure. The residue was dissolved in diethyl ether and a saturated solution of hydrogen chloride gas in methanol was added to precipitate the hydrochloride salt. The first compound to elute from the column gave 274 mg (7% yield) of the [1R,3S,2'R] isomer, m.p. 105°–106° C. The structure was confirmed by NMR and X-ray crystallographic analysis (after recrystallization from acetone by slow evaporation).

The final product to elute from the column gave 400 mg (11% yield) of the [1R,3R,2'R] isomer, m.p. 150°–152°. The structure was confirmed by NMR and X-ray crystallographic analysis (after recrystallization from acetone by slow evaporation).

Step 6: [1R,3S]5,6-Dihydroxy-3-phenyl-1-(2'R pyrrolidino)-1,2,3,4-tetrahydro naphthalene hydrobromide The product of step 5, [1R,3S]5,6-dimethoxy-3-phenyl-1-(2'R pyrrolidino)-1,2,3,4-tetrahydro naphthalene hydrochloride (200 mg, m.p. 105°–106° C.), was dissolved in 10 mL of methylene chloride and the solution was cooled to −78° C. under a nitrogen atmosphere. Boron tribromide (0.25 mL of a 1M solution in methylene chloride) was added and the reaction mixture was stirred for 3 h at −78° C. The reaction mixture was then allowed to warm to −20° C. for 1 h, recooled to −78° C. and quenched with 10 mL of methanol. The solution was evaporated to dryness and distilled with methanol three times to azeotrope methyl borate from the residue. The solid residue was crystallized from methanol/ethyl acetate to give 130 mg (67% yield) of the title compound, m.p. 265° C. (with decomposition). Analysis calculated for $C_{20}H_{24}BrNO_2 + \frac{1}{2}H_2O$; C, 60.16; H, 6.31; N, 3.51. Found: C, 60.06; H, 6.17; N, 3.42.

EXAMPLE 51

[1R,3R]-5,6-Dihydroxy-3-phenyl-1-(2'R pyrrolidino) 1,2,3,4-tetrahydro-naphthalene hydrobromide According to the procedure described in Step 6 of Example 50, [1R,3R]-5,6-dimethoxy-3-phenyl-1 (2'R pyrrolidino)-1,2,3,4-tetrahydro-naphthalene hydrochloride (350 mg), from Step 5 of Example 50, in 10 mL of methylene chloride at −78° C., was treated with 0.472 mL of a 1M solution of boron tribromide in methylene chloride. The title compound was obtained (213 mg) in 61% yield after crystallization from methanol/ethyl acetate, m.p. 250° C. (with decomposition). Analysis calculated for $C_{20}H_{24}BrNO_2 + \frac{1}{2}H_2O$; C, 60.16; H, 6.31; N, 3.51. Found: C, 60.23; H, 6.24; N, 3.38.

EXAMPLE 52

3,4-Dihydro-5,6-dihydroxy-1-(N-methyl)-aminomethyl-3-phenylnaphthalene

1-Aminomethyl-3,4-dihydro-5,6-dimethoxy-3-phenyl-naphthalene from Step 2 of Example 2 was N-methylated as described in Example 35 and deprotected as described in Step 4 of Example 2 to give the title compound as its hydrochloride salt, m.p. 131°–133° C. DCI MS: (M+H)+ 282. Analysis calculated for $C_{18}H_{20}ClNO_2$: C, 68.03; H, 6.34; N, 4.41. Found: C, 67.64; H, 6.54; N, 4.31.

EXAMPLE 53

[1R,3S]5,6-Dihydroxy-1-(N-methyl)-aminomethyl-3-phenyl-1,2,3,4-tetrahydro-naphthalene

[1R,3S]1-Aminomethyl-5,6-dimethoxy-3-phenyl-1,2,3,4-tetrahydro-naphthalene from Step 1 of Example 5 was N-methylated as described in Example 35 and deprotected as described in Step 4 of Example 2 to give the title compound as its hydrochloride salt, m.p. 211°–213° C. DCI MS: (M+H)+ 284. Analysis calculated for $C_{18}H_{22}ClNO_2$: C, 65.75; H, 7.05; N, 4.26. Found: C, 65.54; H, 6.89; N, 4.04.

EXAMPLE 54

[1R,8S,9aR]-1-Amino-5,6-dihydroxy 2,3,7,8,9,9a-hexahydro-8-phenyl-phenalene hydrobromide Step 1: 1-(3'-(3'-Carbomethoxypropanoic acid)-3,4-dihydro-5,6-dimethoxy-3-phenyl naphthalene To a suspension of 4.0 g (14.2 mmol) of 5,6-dimethoxy-3-phenyl-1,2,3,4-tetrahydro-1-naphthalenone, the product of Example 1, in 5 mL of t-butyl alcohol, was added, dropwise, a mixture of 13 mL (99.4 mmol) of dimethyl succinate, 9.6 g (86 mmol) of potassium t-butoxide and 65 mL of t-butyl alcohol. After 10 mL of the mixture was added, the reaction mixture was heated to 55° C. and maintained at this temperature for the duration of the addition. When the addition was complete, the reaction mixture was heated for an additional hour, cooled and poured into 50 mL of ice cold 2N hydrochloric acid solution. The aqueous phase was extracted with 5×100 mL of diethyl ether. The combined organic layers were extracted with 5×100 mL of aqueous saturated sodium bicarbonate solution. The combined aqueous layers were acidified to pH 3 with 6N hydrochloric acid and the product was extracted with 2×200 mL of 1:1 diethyl ether:ethyl acetate. The organic phase was dried over anhydrous magnesium sulfate, filtered and concentrated in vacuo. The title compound (5.0 g, 86% yield) was obtained as an oil. MS DCI: 397 (M+H)+. $^1$H NMR (CDCl$_3$) delta 2.6–2.8 (m, 4H), 3.1–3.3 (m, 1H), 3.69 (s, 3H), 3.71 (s, 3H), 3.87 (s, 3H), 4.1–4.25 (m, 1H), 5.9–6.0 (m, 1H), 6.7–6.8 (m, 1H), 7.0–7.5 (m, 6H).

Step 2:
1-(3'-(3'-Carbomethoxypropanoicacid)-5,6-dimethoxy-3-phenyl-1,2,3,4-tetrahydro-naphthalene To a solution of 15.8 g (39.9 mmol) of 1-(3'-(3'-carbomethoxypropanoic acid)-3,4-dihydro-5,6-dimethoxy- 3-phenyl-naphthalene from Step 1, in 200 mL of ethyl acetate was added 3.16 g of 10% palladium supported on carbon. The reaction mixture was shaken under 4 atmospheres of hydrogen until hydrogen uptake ceased. The reaction mixture was filtered and concentrated under reduced pressure to give 12.2 g (74% yield) of the title compound as an oil. The product was carried on to the next step without further purification.

Step 3:
1-Carbomethoxy-5,6-dimethoxy-3-hydroxy-8-phenyl-7,8,9,9a-tetrahydro-phenalene The product of Step 2 (3.5 g, 8.5 mmol) was added to 11 g of polyphosphoric acid at 0° C. The ice bath was removed and the reaction mixture was stirred at ambient temperature for 3 hours. The aqueous solution was extracted with 3×50 mL of 1:1 ethyl acetate:diethyl ether. The combined organic layers were washed with 50 mL of saturated aqueous sodium bicarbonate solution, dried over anhydrous magnesium sulfate, filtered and concentrated under reduced pressure. The product was purified by chromatography on silica gel eluted with 20% ethyl acetate in hexanes. Four diastereomeric products were obtained, of which two were characterized.

The first diastereomer, [1R,8S,9aR]1-carbomethoxy-5,6-dimethoxy-3-hydroxy-8-phenyl-7,8,9,9a-tetrahydro-phenalene (54-3A), was obtained in 18% yield (0.59 g) as a solid, m.p. 170°–172° C. DCI MS: $(M+H)^+$ 381, $(M+NH_4)^+$ 398. $^1$H NMR (CDCl$_3$) delta 1.6–1.7 (m, 1H), 2.1–2.2 (m, 1H), 2.6–2.7 (m, 1H), 2.9–3.1 (m, 4H), 3.2–3.4 (m, 2H), 3.71 (m, 3H), 3.87 (s, 3H), 3.91 (s, 3H), 7.2–7.4 (m, 5H), 7.53 (s, 1H).

The second diastereomer, [1S,8S,9aR]-1-carbomethoxy-5,6-dimethoxy-3-hydroxy-8-phenyl-7,8,9,9a-tetrahydrophenalene (54-3B) was obtained in 18% yield (0.60 g) as a solid, m.p. 160°–161° C. DCI MS: $(M+H)^+$ 381, $(M+NH_4)^+$ 398. $^1$H NMR (CDCl$_3$) delta 2.0–2.1 (m, 1H), 2.15–2.25 (m, 1H0, 2.6–2.8 (m, 2H), 3.0–3.1 (m, 2H), 3.2–3.3 (m, 2H), 3.4–3.5 (m, 1H), 3.7 (s, 3H), 3.83 (s, 3H), 3.91 (s, 3H), 7.2–7.4 (m, 5H), 7.54 (s, 1H).

Step 4: [1R,8S,9aR]1 Carbomethoxy 5,6 dimethoxy-2,3,7,8,9,9a-hexahydro-8-phenyl-phenalene To a solution of 0.5 g (1.3 mmol) of [1R,8S,9aR]-1-carbomethoxy 5,6 dimethoxy 3 hydroxy 8 phenyl-7,8,9,9a-tetrahydro-phenalene (54-3A), in 50 mL of methanol, 50 mL of ethyl acetate and 0.1 mL of concentrated aqueous hydrochloric acid was added 0.2 g of 5% palladium on carbon and the reaction mixture was shaken under 4 atmospheres of hydrogen until the uptake of hydrogen had ceased. The palladium catalyst was removed by filtration through Celite filter aid and the filtrate was concentrated to give a white solid, which was carried on to the next step without purification.

Step 5: [1R,8S,9aR]-5,6-Dimethoxy-2,3,7,8,9,9a -hexahydro-8-phenyl-phenalene-1-carboxylic acid Crude [1R,8S,9aR]-1-carbomethoxy-5,6 dimethoxy 2,3,7,8,9,9a-hexahydro-8-phenyl-phenalene (0.8 g, 2.1 mmol) from Step 4, was dissolved in 100 mL of methanol and 8 mL of 1N aqueous sodium hydroxide was added. After stirring for 3 days at ambient temperature, the methanol was removed from the reaction mixture under reduced pressure. The residue was partitioned between 50 mL of diethyl ether and 75 mL of water. The aqueous phase was acidified to pH 2 with 6M hydrochloric acid solution and extracted with 3×25 mL of 1:1 ethyl acetate:diethyl ether. The combined organic layers were washed with saturated aqueous sodium chloride, dried over anhydrous magnesium sulfate, filtered and concentrated in vacuo to give 0.74 g (100% yield) of the title compound as an oil. DCI MS: $(M+H)^+$ 253. $^1$H NMR (CDCl$_3$) delta 2.0–2.3 (m, 2H), 2.65–2.85 (m, 2H), 2.9–3.1 (m, 6H), 3.2–3.3 (m, 1H), 3.73 (s, 3H), 3.83 (s, 3H), 6.56 (s, 1H), 7.2–7.4 (m, 5H).

Step 6:
[1R,8S,9aR]-1-Carbobenzyloxyamino-5,6-dimethoxy-2,3,7,8,9,9a-hexahydro-8-phenyl-phenalene

[1R,8S,9aR]-5,6-Dimethoxy-2,3,7,8,9,9a-hexahydro-8-phenyl-phenalene-1-carboxylic acid (0.8 g, 2.3 mmol), from Step 5, and 0.32 mL (2.3 mmol) of triethylamine were dissolved in 16 mL of toluene and 0.55 mL (2.5 mmol) of diphenylphosphoryl azide was added. The reaction mixture was heated at 80° C. for 2.5 h then 0.5 mL (4.8 mmol) of benzyl alcohol was added and heating was continued at 80° C. for an additional 3 h and at 65° C. for 15 h. The reaction mixture was cooled and concentrated under reduced pressure. The residue was dissolved in 25 mL of diethyl ether and the ether solution was washed with 10 mL of 1N aqueous sodium hydroxide solution and brine, dried over magnesium sulfate, filtered and concentrated in vacuo. The residue was purified by chromatography on silica gel eluted with 20% ethyl acetate in hexanes to qive 0.4 g (39% yield) of the title compound as a white solid. DCI MS: $(M+NH_4)^+$ 475, $(M+H)^+$ 458, (M-benzyl+H)$^+$ 367, (M-benzyloxycarbonyl+2H)$^+$ 324. $^1$H NMR (CDCl$_3$) delta 1.6–1.7 (m, 3H), 2.2–2.35 (m, 2H), 2.6–2.75 (m, 2H), 2.9–3.0 (m, 3H), 3.2–3.3 (m, 1H), 3.73 (s, 3H), 3.82 (s, 3H), 4.65–4.7 (m, 1H), 5.08 (s, 2H), 6.54 (s, 1H), 7.2–7.4 (m, 10H).

Step 7:
[1R,8S,9aR]-1-Amino-5,6-dimethoxy-2,3,7,8,9,9a-hexahydro-8-phenyl-phenalene A suspension of 0.65 g (1.4 mmol) of [1R,8S,9aR]-1-carbobenzyloxyamino-5,6-dimethoxy-2,3,7,8,9,9a-hexahydro-8-phenyl-phenalene, from Step 6, in 50 mL of methanol and 0.1 g of 10% palladium on carbon was stirred under 1 atmosphere of hydrogen for 1 hour. The solid dissolved as the reaction proceeded. The palladium catalyst was removed by filtration and the filtrate was concentrated under reduced pressure to give 0.4 g (87% yield) of crude product which was carried on to the next step without further purification.

Step 8: [1R,8S,9aR]-1 Amino-5,6-dihydroxy-2,3,7,8,9,9a-hexahydro-8-phenyl-phenalene hydrobromide A solution of 0.4 g (1.2 mmol) of [1R,8S,9aR]-1-amino-5,6-dimethoxy-2,3,7,8,9,9a-hexahydro-8 phenyl-phenalene, from Step 7, in 9 mL of methylene chloride was treated with 4.4 mL of a 1M solution of boron tribromide in methylene chloride (4.4 mmol), added dropwise at −78° C. The reaction mixture was warmed to ambient temperature for 1 h and recooled to 78° C. and quenched with 5 mL of methanol. The reaction mixture was allowed to warm to ambient temperature and stirred at ambient temperature for 1 h. The solvent was removed in vacuo. Methanol (5 mL) was added and the solution was concentrated to remove methyl borate by azeotropic distillation. The title compound was obtained after recrystallization from ethanol/diethyl ether as a white solid.

DCI MS: (M+H)+ 279, (M+NH4)+ 296. $^1$H NMR (d$_6$-DMSO) delta 1.4–1.6 (m, 1H), 1.7–1.9 (m, 1H), 2.1–2.2 (m, 1H), 2.2–2.3 (m, 1H), 2.4–2.5 (m, 2H), 2.7–3.2 (m, 5H), 6.41 (s, 1H), 7.2–7.4 (m, 5H), 8.0 (br s, 5H). Analysis calculated for C$_{19}$H$_{22}$BrNO$_2$+0.5H$_2$O: C, 59.23; H, 5.99; N, 3.64. Found: C, 59.26; H, 5.86; N, 3.59.

EXAMPLE 55

[1S,8S,9aR]-1-Amino-5,6-dihydroxy-2,3,7,8,9,9a-hexahydro-8-phenyl-phenalene hydrobromide The title compound was prepared from the second isomeric product of Step 3 of Example 54 (54-3B) according to the procedures described in Steps 4 through 8 of Example 54. DCI MS: (M+H)+ 279, (M+NH4)+ 296. $^1$H NMR (d$_6$DMSO) delta 1.6–1.75 (m, 1H), 1.8–2.05 (m, 2H), 2.25–2.7 (m, 5H), 2.85–3.05 (m, 3H), 6.37 (s, 1H), 7.1–7.4 (m, 5H), 7.7 (br s, 5H). Analysis calculated for C$_{19}$H$_{22}$BrNO$_2$+1H$_2$O: C, 57.88; H, 6.14; N, 3.55. Found: C, 57.82; H, 5.74; N, 3.56.

EXAMPLE 56

6,7-Dihydroxy-4-phenyl-2,3,4,5-tetrahydro-1H-benz[e]isoindole formic acid salt

Step 1:
5,6-Dimethoxy-3-phenyl-2-thiophenyl-1,2,3,4-tetrahydro-naphthalenone To a solution of 28.9 g (0.102 mol) of 5,6-dimethoxy-3-phenyl-1,2,3,4-tetrahydro-naphthalenone, the product of Example 1, in 240 mL of THF was added 40.4 g (0.107 mol) of phenyltrimethylammonium tribromide. After stirring at ambient temperature for 1 h, 960 mL of water was added. The solution was extracted with 3×250 mL of ethyl acetate. The combined organic phase was washed with 3×250 mL of water and 250 mL of brine, dried over anhydrous magnesium sulfate, filtered and concentrated under reduced pressure to give an oil which was carried on without further purification or characterization.

A solution of sodium methoxide was prepared by the addition of 3.28 g (0.143 mol) of sodium metal to 97 mL of methanol with cooling to 0° C. Thiophenol (14.6 mL 0.143 mol) was added dropwise over 30 minutes and the reaction mixture was stirred for an additional 10 minutes at 0° C. A solution of the above mentioned oil in 60 mL of THF was added to the reaction mixture over a 30 minute period and it was allowed to warm to ambient temperature for 4 h. The solvents were removed in vacuo and the residue was dissolved in a mixture of 250 mL of methylene chloride and 250 mL of water. The organic phase was collected and washed with brine, dried over anhydrous sodium sulfate, filtered and concentrated under reduced pressure. The product was recrystallized from ethyl acetate/hexanes to give 33.15 g 83% yield from the ketone) of 5,6-dimethoxy-3-phenyl-2-thiophenyl-1,2,3,4-tetrahydro-naphthalenone as a white solid. MS DCI: (M+H)+ 391. $^1$H NMR (CDCl$_3$) delta 3.35 (dd, 1H, J=6, 18 Hz), 3.55 (dd, 1H, J=6, 18 Hz), 3.71 (q, 1H, J=6 Hz), 3.82 (s, 3H), 3.93 (s, 3H), 4.19 (d, 1H, J=6 Hz), 6.91 (d, 1H, J=9 Hz), 7.1–7.3 (m, 8H), 7.4–7.5 (m, 2H), 7.37 (d, 1H, J=9 Hz).

Step 2:
3,4-Dihydro-5,6-dimethoxy-3-phenyl-2-sulfoxophenyl-naphthalene

A solution of 20.96 g (53.7 mmol) of 5,6-dimethoxy-3-phenyl-2-thiophenyl-1,2,3,4-tetrahydro-naphthalenone, from Step 1, in 320 mL of ethanol was treated with 20.03 g (0.529 mol) of sodium borohydride. The reaction mixture was heated to reflux temperature for 2 h, then cooled and 500 mL of water was added. The solvents were removed in vacuo and the residue was taken up in 500 mL of 1:1 diethyl ether:methylene chloride and 500 mL of water. The organic layer was removed and washed with 100 mL each of water and brine, dried over anhydrous magnesium sulfate, filtered and concentrated under reduced pressure. The resultant crude alcohol was dehydrated by the addition of 700 mL of toluene and 3.6 g (18.9 mmol) of p-toluenesulfonic acid monohydrate and heating to reflux with azeotropic removal of water for 30 minutes. After cooling, the solution was washed with 3X 100 mL of saturated aqueous sodium bicarbonate, 100 mL of water, dried over anhydrous magnesium sulfate, filtered and concentrated in vacuo. The crude thio-enolether was dissolved in 360 mL of methylene chloride. This solution was cooled to 150° C. and a solution of 12.1 g of 3 chloroperoxybenzoic acid (mCPBA) in 160 mL of methylene chloride was added dropwise over 30 minutes. After the addition was complete, the reaction was quenched by the addition of 100 mL of aqueous saturated sodium thiosulfate. The organic layer was separated, washed with 3×100 mL of saturated aqueous sodium bicarbonate and 100 mL of water, dried over anhydrous sodium sulfate, filtered and concentrated under reduced pressure. The product was purified on silica gel eluted with 25% ethyl acetate in hexanes to give 18.65 g (89% yield) of 3,4-dihydro-5,6-dimethoxy-3-phenyl-2-sulfoxophenylnaphthalene as a white solid as a mixture of diastereomers. MS DCI: (M+H)+ 391. $^1$H NMR (CDCl$_3$) delta 2.9–3.1 (m, 1H), 3.1–3 3 (m, 1H) 3.46 and 3.51 (2×s, 3H total), 3.55 and 3.7 (2×m, 1H total) 3.83 and 3.86 (2×s, 3H total), 6.75–7.15 (m, 7H), 7.3–7.6 (m, 6H).

Step 3: N-Trimethylsilylmethyl benzylamine

A mixture of 264 mL (2.42 mol) of benzylamine and 97.7 g (0.796 mol) of chloromethyltrimethylsilane was heated to 200° C. for 2.5 h then cooled to 10° C. A 0.1M sodium hydroxide solution (400 mL) was added and the product was extracted with 3×200 mL of diethyl ether. The combined organic phase was washed with 100 mL of water, dried over anhydrous magnesium sulfate, filtered and concentrated under reduced pressure. The product was distilled at 115°–125° C. and 5 mm of Hg to give 125.4 g (81% yield) of N-trimethysilylmethyl benzylamine as a clear liquid. $^1$H NMR (CDCl$_3$) delta 0.0 (s, 9H), 1.1 (br s, 1H), 2.01 (s, 2H), 3.76 (s, 2H), 7.1–7.3 (m, 5H).

Step 4: N-Methoxymethyl-N-trimethylsilylmethyl benzylamine

N-Trimethylsilylmethyl benzylamine (125.4 g, 0.649 mol), from Step 3, was added dropwise over a 10 minute period to a solution of 69.5 mL of 37% aqueous formaldehyde at 0° C. After an additional 10 minutes, 75.2 mL of methanol was added. The solution was then saturated with solid potassium carbonate and stirred at 0° C. for 1 h. The layers were separated and the organic phase was stirred over solid potassium carbonate at ambient temperature for 18 h. The solution was filtered and fractionally distilled at 20 mm of Hg to give a 145°-155° C. fraction as a viscous oil, identified as N-methoxymethyl-N-trimethylsilylmethyl benzylamine.

$^1$H NMR (CDCl$_3$) delta 0.0 (s, 9H), 2.13 (s, 2H), 3.18 (s, 3H), 3.71 (s, 2H), 3.96 (s, 2H), 7.1-7.3 (m, 5H).

Step 5:
2-Benzyl-6,7-dimethoxy-4-phenyl-2,3,4,5-tetrahydro-1H-benz[e]isoindole To a solution of 1.22 g (3.13 mmol) of 3,4 dihydro-5,6-dimethoxy-3-phenyl-2-sulfoxophenyl-naphthalene, from Step 2, in 10 mL of methylene chloride was added 1 g (4.21 mmol) of N-methoxymethyl-N-trimethylsilylmethyl benzylamine, from Step 4, and 0.1 mL of trifluoroacetic acid. At 12 h intervals, the amine and acid additions were repeated 7 more times. The solvent was then removed under reduced pressure with heating to 100°C. and the product was purified on silica gel eluted with 25% ethyl acetate in hexanes to give 0.14 g (11% yield) of 2-benzyl-6,7-dimethoxy-4-phenyl-2,3,4,5-tetrahydro 1H-benz[e]isoindole. MS DCI: (M+H)$^+$ 398. $^1$H NMR (CDCl$_3$) delta 3.0-3.15 (m, 1H), 3.25-3.35 (m, 1H), 3.45-3.55 (m, 3H), 3.62 (s, 3H), 3.65-3.7 (m, 2H), 3.8-3.9 (m, 2H), 3.82 (s, 3H), 6.68 (m, 1H), 7.1-7.4 (m, 11H).

Step 6:
6,7-Dimethoxy-4-phenyl-2,3,4,5-tetrahydro-1H-benz[e]isoindole hydrochloride To a solution of 1.0 g (2.52 mmol) of 2-benzyl-6,7-dimethoxy-4-phenyl-2,3,4,5-tetrahydro-1H-benz-[e]isoindole, from Step 5, in 22 mL of 1,2-dichloroethane was added 0.11 g (0.05 mmol) of 1,8-bis(dimethylamino)naphthalene and 0 33 mL (3.15 mmol) of 1-chloroethyl chloroformate at 0° C. The solution was heated to reflux for 2 h and the solvent removed in vacuo. The residue was filtered through silica gel, eluting with 25% ethyl acetate in hexanes. After concentration under reduced pressure, methanol (20 mL) was added and the solution was heated to reflux for 30 minutes before the solvent was removed in vacuo. The product was crystallized from ethanol/diethyl ether to give 0.46 g (75% yield) of 6,7-dimethoxy-4-phenyl-2,3,4,5-tetrahydro 1H-benz[e]isoindole hydrochloride as a white solid. MS DCI: (M+H)$^+$ 308. $^1$H NMR (d$_6$ DMSO) delta 3.05-3.25 (m, 2H), 3.55 (s, 3H), 3.80 (s, 3H), 3.88 (m, 1H), 4.0-4.15 (m, 2H), 4.25-4.45 (m, 2H), 6.91 (m, 1H), 7.15-7.3 (m, 3H), 7.4-7.6 (m, 3H).

Step 7:
6,7-Dihydroxy-4-phenyl-2,3,4,5-tetrahydro-1H-benz[e]isoindole formic acid salt A suspension of 54.5 mg (0.159 mmol) of 6,7-dimethoxy-4-phenyl-2,3,4,5-tetrahydro-1H-benz[e]isoindole hydrochloride, from Step 6, in 2 mL of methylene chloride was cooled to −78° C. and 0.64 mL of a 1M solution of boron tribromide in methylene chloride was added. The reaction mixture was warmed to ambient temperature for 1 h and recooled to 78° C. before 1 mL of methanol was added. After warming to ambient temperature for 1 h, the solvents were removed in vacuo. Additional methanol (5 mL) was added and removed in vacuo. The product was purified on silica gel eluted with 18:1:1 ethyl acetate:formic acid:water to give 29.8 mg (58% yield) of 6,7-dihydroxy-4-phenyl-2,3,4,5-tetrahydro-1H-benz[e]isoindole formic acid salt as an off white powder, m.p. 144° C. MS DCI: M$^+$ 279. $^1$H NMR (d$_6$-DMSO) delta 2.95-3.15 (m, 2H), 3.6-3.9 (m, 3H), 4.1-4.3 (m, 2H), 6.43 (d, 1H, J=7.5 Hz), 6.62 (d, 1H, J=7.5 Hz), 7.1-7.3 (m, 5H), 8.3 (s, 1H).

EXAMPLES 57-59

Following the synthesis outlined in Example 6, using the appropriate aldehyde, Examples 57-58 were made, as their hydrobromide salts, as disclosed in Table 4. The structure of each was confirmed by melting point (m.p), elemental analysis and mass spectra as designated. Example 59, as disclosed in Table 4, was prepared, using the appropriate aldehyde, as described in Examples 6 and 7 as its hydrobromide salt. The structure was confirmed by melting point (m.p), elemental analysis and mass spectra as designated.

EXAMPLES 60 and 62

Following the synthesis outlined in Examples 1A and 2, the 1-aminomethyl precursors to Examples 60-62 were prepared, with the catechol hydroxyl qroups protected as their dimethyl ethers. The 1-aminomethyl intermediates were N acylated and reduced as described in Example 35 and deprotected as described in Step 4 of Example 2, using the appropriate acyl chloride and lithium aluminum hydride (LAH) as the reducing agent to give Examples 60-62 as their hydrochloride salts unless otherwise noted. In the case of Example 61, the acylation-reduction sequence was repeated before the deprotection step was carried out to give the dialkylamino derivative. The structures of the compounds of Example 60-62 are disclosed in Table 4. The structure of each was confirmed by melting point (m.p), elemental analysis and mass spectra a designated.

TABLE 4

Examples 57-62

| Example # | Compound | Aldehyde | m.p. | MS** | Elemental Analysis C H N |
|---|---|---|---|---|---|
| 57 | [structure: 4-phenyl-tetrahydrobenz[e]isoindole with 6,7-dihydroxy, phenyl substituent with OH, and CH$_2$—NH$_2$] | [structure: 3-methoxybenzaldehyde] | 210° C. | 284 | calc + $\frac{3}{4}$ H$_2$O: 54.05 5.20 3.71 Found: 53.95 4.97 3.86 |

TABLE 4-continued

Examples 57-62

| Example # | Compound | | m.p. | MS** | Elemental Analysis | | |
|---|---|---|---|---|---|---|---|
| 58 | [structure: tetrahydronaphthalene with OH, HO, OH substituents, CH₂NH₂, and 4-hydroxyphenyl] | [structure: 4-methoxybenzaldehyde] | 223–226° C. | 284 | calc + 0.1 H₂O: Found: | 55.78 5.01 3.83 55.64 5.25 3.74 | |
| 59 | [structure: tetrahydronaphthalene with OH, HO, CH₂NH₂, and 3-hydroxyphenyl] | [structure: 3-methoxybenzaldehyde] | 250 | 286 | calc + 1 H₂O: Found: | 53.13 5.77 3.65 52.97 5.53 4.03 | |
| | | Acyl chloride | | | HRMS*** | | |
| 60 | [structure: tetrahydronaphthalene with OH, HO, phenyl, and CH₂NH-propyl] | [structure: butyryl chloride] | 198 | 310 | calc: found: | 309.1725 309.1722 | |
| 61 | [structure: tetrahydronaphthalene with OH, HO, phenyl, and CH₂N(propyl)₂*] | [structure: butyryl chloride] | | 352 | calc: found: | 351.2198 351.2203 | |
| 62 | [structure: tetrahydronaphthalene with OH, HO, phenyl, and CH₂NH-ethyl] | [structure: propionyl chloride] | 122 | 296 | calc: found: | 295.1572 295.1571 | |

*methane sulfonic acid salt
**DCI MS (M + H)+
***High Resolution Mass Spectrum

Competitive Binding

The procedure for the D 1 binding assays is as follows. Homogenized rat caudate is incubated in the presence of [$^{125}$I]SCH-23982, a selective antagonist of the D-1 receptor, and test compounds according to procedures previously described (A. Sidhu and J. W. Kebabian, Eur. J. Pharmacol. 113, 437, 1985 and A. Sidhu, J. C. van Oene, P. Dandridge, C. Kaiser and J. W. Kebabian, Eur. J. Pharmacol. 128, 213, 1986). The molar potency of the test compounds to compete for occupancy for the specific binding sites in the membranes is quantified and the affinity of the test compound can be calculated from the competition experiment (Y. C. Cheng and W. H. Prusoff, Biochem. Pharmacol. 22, 3099, 1973).

The procedure for the D-2 binding assay is similar to that used for the D-1 assay. Homogenized rat caudate is used as the source of D-2 receptors. The tissue homogenate is incubated in the presence of [$^{125}$I]-p-aminophenethyl spiroperidol, a selective antagonist of the D-2 receptor and test compounds (T. Agui, N. Amlaiky, M. G. Caron and J. W. Kebabian, Mol. Pharmacol. 33, 163, 1988). The molar affinity of the test compound for the binding site is calculated by assuming a competitive interaction between the test compound and the radiolabeled ligand.

Table 5 indicates the competitive binding for the D-1 and D-2 receptors.

TABLE 5

| Competitive binding for the D-1 and D-2 receptors | | |
|---|---|---|
| Example No. | D-1 KI (μM) | D-2 KI (μM) |
| dopamine | 8.005 | 6.310 |
| 2A | 0.151 | >10 |
| 5 | 0.030 | 0.759 |
| 6 | 0.195 | ND* |
| 7 | 0.138 | 1.479 |
| 9 | 0.0367 | 13.6458 |
| 10 | 0.0025 | 0.5754 |
| 11 | 2.6915 | 12.5893 |
| 12 | 0.0038 | 1.6032 |
| 13 | 0.1023 | 3.8019 |
| 14 | 0.1396 | 6.3096 |
| 15 | 6.9183 | ND |
| 16 | 0.2154 | 0.6166 |
| 17 | 0.0011 | 0.4898 |
| 18 | 0.2917 | 1.8408 |
| 19 | 2.1627 | 1.2882 |
| 20 | 0.9333 | 0.7161 |
| 21 | 0.2483 | 1.1885 |
| 22 | 0.0146 | 1.9055 |
| 23 | 0.2985 | 0.5012 |
| 24 | 0.3138 | 0.5754 |
| 25 | 0.2089 | 3.1261 |
| 26 | 112.2018 | ND |
| 27 | 71.6143 | ND |
| 28 | 3.1989 | 0.4786 |
| 29 | 12.0226 | 10.1158 |
| 30 | 0.5623 | 0.6026 |
| 31 | 2.3174 | ND |
| 32 | 0.7328 | 5.5377 |
| 33 | 0.0219 | 3.7154 |
| 34 | 0.0006 | 0.7943 |
| 35 | 0.0141 | 0.7244 |
| 36 | 0.1549 | 5.5590 |
| 37 | 1.5370 | 0.6506 |
| 38 | 0.8318 | 0.6358 |
| 39 | 350.7519 | 2.1878 |
| 40 | 3.3113 | 0.9772 |
| 41 | 7.4989 | 3.0200 |
| 42 | 0.9333 | 16.7880 |
| 43 | 0.1679 | 9.5499 |
| 44 | 0.6546 | 2.5902 |
| 45 | 0.1148 | 6.5063 |
| 46 | 6.6069 | ND |
| 47 | 4.6238 | 15.8489 |
| 48 | 1.3490 | 15.8489 |
| 49 | 1.5488 | 5.6234 |
| 50 | 0.0259 | 1.3490 |
| 51 | 0.8318 | 4.6238 |
| 52 | 0.4571 | 3.0903 |
| 53 | 0.0224 | 9.7724 |
| 54 | 0.1059 | 2.1878 |
| 55 | 2.9512 | ND |
| 56 | 0.0575 | ND |
| 57 | 0.1000 | 22.3872 |
| 58 | 1.3804 | ND |
| 59 | 0.0450 | 3.7801 |
| 60 | 6.5313 | 2.5119 |
| 61 | 54.3250 | 12.3027 |

TABLE 5-continued

| Competitive binding for the D-1 and D-2 receptors | | |
|---|---|---|
| Example No. | D-1 KI (μM) | D-2 KI (μM) |
| 62 | 0.8511 | ND |

*ND = not determined

Intrinsic Activity

The intrinsic activity of the test molecules is determined in assays of the enzyme adenylate cyclase (K. J. Watling and J. Neurochem. 36, 559, 1981 and J. W. Kebabian, G. L. Petzold and P. Greengard, Proc. Nat. Acad. Sci. U.S.A., 69, 2145, 1972). Dopamine's interaction with the D 1 receptor causes a dose dependent increase in the formation of cyclic AMP. Cell free homogenates of tissue are incubated in a solution containing buffer, ions and adenosine triphosphate (ATP); the dopamine agonist increases the conversion of ATP into cyclic AMP. Our tests use tissue from the goldfish retina as well as the rat striatum.

Table 6 indicates the intrinsic activity in an adenylate cyclase assay indicating that the compounds of the present invention are dopamine agonists.

TABLE 6

| Intrinsic activity in adenylate cyclase assay | | |
|---|---|---|
| Example No. | EC$_{50}$ (μM) | Intrinsic activity |
| dopamine | 2.474 | 100.00 |
| 2A | 0.0425 | 55.75 |
| 5 | 0.010 | 65.60 |
| 6 | 0.074 | 56.50 |
| 7 | 0.029 | 73.55 |
| 9 | 0.0169 | 58.66 |
| 10 | 0.0024 | 65.98 |
| 12 | 0.0031 | 70.64 |
| 13 | 0.1423 | 88.47 |
| 14 | 0.0687 | 64.87 |
| 15 | 5.5377 | 77.47 |
| 16 | 0.0227 | 66.63 |
| 17 | 0.0019 | 60.06 |
| 18 | 0.0240 | 50.93 |
| 19 | 0.4299 | 46.23 |
| 20 | 0.0295 | 55.70 |
| 21 | 0.0188 | 63.20 |
| 22 | 0.0028 | 66.90 |
| 23 | 0.0344 | 92.73 |
| 24 | 0.0052 | 75.93 |
| 25 | 0.1334 | 110.70 |
| 26 | 1.5668 | 19.87 |
| 27 | 0.6607 | 42.73 |
| 28 | 0.0311 | 78.20 |
| 29 | 0.2512 | 91.43 |
| 30 | 0.0127 | 84.30 |
| 31 | 0.2326 | 92.17 |
| 32 | 0.0136 | 89.77 |
| 33 | 0.0005 | 119.00 |
| 34 | 0.0073 | 86.50 |
| 35 | 0.0013 | 106.00 |
| 36 | 0.0120 | 63.74 |
| 37 | 0.0465 | 60.35 |
| 38 | 0.0724 | 74.70 |
| 39 | 2.7332 | 77.60 |
| 40 | 0.7762 | 59.57 |
| 41 | 2.0261 | 68.20 |
| 42 | 0.0972 | 95.50 |
| 43 | 0.1216 | 95.20 |
| 44 | 0.3162 | 90.75 |
| 45 | 0.1634 | 62.33 |
| 46 | 8.5770 | 99.07 |
| 47 | 3.5755 | 127.33 |
| 48 | 0.5188 | 111.00 |
| 49 | 0.3311 | 100.70 |
| 50 | 0.0012 | 64.68 |
| 51 | 0.0753 | 71.27 |
| 52 | 0.0355 | 78.13 |
| 53 | 0.0044 | 102.03 |
| 54 | 0.0211 | 64.67 |

TABLE 6-continued

| | Intrinsic activity in adenylate cyclase assay | |
|---|---|---|
| Example No. | $EC_{50}$ ($\mu$M) | Intrinsic activity |
| 55 | 0.6026 | 56.37 |
| 56 | 0.0188 | 46.80 |
| 57 | 0.0334 | 91.33 |
| 58 | 0.0437 | 84.03 |
| 59 | 0.0046 | 97.73 |
| 60 | 6.9716 | 58.93 |
| 61 | ND | ND |
| 62 | 3.1381 | 53.87 |

Rotation Behavior

The dopamine depleted animal approximates the situation in Parkinson's Disease. Our behavioral assay is the rat rotational model. Striatal dopamine is depleted by the intracranial injection of 6-hydroxydopamine, a neurotoxin which specifically destroys catecholaminergic neurons. The intercranial injection is conducted on anesthetized animals standard stereotaxic techniques (U. Ungerstedt and G. W. Arbuthnott, Brain Research, 24, 485, 1970 and U. Ungerstedt, Acta Physiol. Scand. Suppl. 367, 69, 1973). When the striatal dopamine receptors are stimulated by the test compounds, the rats rotate or physically turn in a direction that is away from the side of their body that receives the greater dopaminergic activation.

Table 7 indicates the rotation behavior of selected compounds of the present invention.

TABLE 7

| | Rotation behavior | |
|---|---|---|
| Example No. | $ED_{50}$ (mg/kg) (subcutaneous) | $ED_{50}$ (mg/kg) (oral) |
| 2A | 0.45 | 9.5 |
| 3 | 0.45 | 12.5 |
| 5 | ND* | 7.5 |
| 6 | 1.75 | 60.0 |
| 7 | 1.5 | 40.0 |
| 9 | 0.063 | ND |
| 10 | 0.125 | 5.0 |
| 12 | 0.20 | 6.25 |
| 18 | 5.0 | ND |
| 22 | 0.375 | 6.25 |
| 24 | 2.0 | ND |
| 28 | 20.0 | ND |
| 35 | 0.25 | 6.25 |
| 36 | 0.10 | ND |

*ND = not determined

CARDIOVASCULAR PHARMACOLOGY

Hemodynamic Studies in Anesthetized Dogs: Male beagle dogs are anesthetized with pentobarbital (30 mg/kg, i.v.) and maintained with i.v. infusion (Abbott/-Shaw Life Care Pump, Model II/D) to maintain stable cardiovascular function. The dogs are incubated with a cuffed endotracheal tube and ventilated with room air by means of a positive pressure respiratory pump. Expired respiratory $CO_2$ is monitored with a Beckman LB-2 gas analyzer and maintained at 5% by appropriate pump adjustments. The dogs are maintained at a body temperature of 37.5°±1.0° C. with a thermostatically controlled animal table. Polyethylene catheters are placed in the abdominal aorta via the femoral and carotid arteries for blood pressure and left ventricular pressure recordings. A Swan-Ganz thermodilution catheter with a 15 cm proximal port is placed in the jugular vein for central venous and pulmonary arterial recordings and for determination of cardiac output (American Edwards Cardiac Output Computer, Model COM-1). Heart rate and electrocardiogram (ECG) recordings are made from a Lead II ECG connection. With the dog on its right side the abdominal cavity is surgically entered laterally, immediate inferior to the rib cage, to expose the left renal artery. A calibrated electromagnetic flow probe (Carolina Medical Electronics) is positioned around the renal artery. The abdominal cavity is closed with wound clips. Recordings are made on a Grass polygraph.

An additional small polyethylene catheter is inserted into a branch of the left femoral artery and the tip positioned in the aorta above the renal arteries. Compounds are continuously infused intraarterially (Harvard Infusion Pump, Model 975) for approximately 5 minutes per dose. A thirty fold dose response curve is administered by varying flow rate from 0.01 to 0.30 ml/minute.

Table 8 indicates the effects of selected compounds of the present invention on cardiovascular pharmacology.

TABLE 8

EFFECTS OF SELECTED DOPAMINERGIC AGONISTS ON THE RENAL BLOOD FLOW (RBF) AND MEAN ARTERIAL BLOOD PRESSURE (MAP) IN ANESTHETIZED DOGS

| EXAMPLE # | Dose Range* (g/kg/min) | Max Increase RBF (%) | Max Decrease MAP (%) |
|---|---|---|---|
| Ex. 2A | 3–10 | 27 | 32 |
| Ex. 5 | 1–3 | 35 | 26 |
| Ex. 7 | 1–30 | 48 | 39 |
| Ex. 6 | 1–10 | 94 | 13 |
| Ex. 3 | 1–10 | 83 | 8 |

*Cumulative intraaortic (above renal) infusion.

DIURETIC EFFECTS OF Example 2A IN SPONTANEOUSLY HYPERTENSIVE RATS

Male, spontaneously hypertensive rats (SHR), weighing 285–350 grams were used. Following an overnight fasting period with free access to drinking water, the rats received an intragastric fluid load of 0.9% saline at 5% of their body weight. Simultaneously with the load, the rats were dosed with a test compound or vehicle and placed individually in stainless steel metabolic cages where they kept access to drinking water throughout the duration of the experiment. For intravenous administration, the rats were instrumented with indwelling cannulas placed into the jugular vein at least one week prior to the experiment.

Urine was collected at 2 and 4 hours following drug administration. The volume of excreted urine at each collection interval was measured accurately and the samples were analyzed for sodium, potassium and chloride ions. Sodium and potassium were measured using a Digital Readout Flame Photometer (Instrumentation Labs). Chloride was measured by the method of Shales and Shales, J. Bio. Chem., 140:879, 1941. The statistical analysis of the data was computed by an off-line computer program. In this program, a comparison test is made between the vehicle (control) group and each treatment group for all variables at each time interval of the experiment. The test of statistical siqnificance is based on the Student's t-test, where the calculated t is a measure of the probability density function.

The compound of Example 2A was administered to six rats intravenously at a dose of 0.3, 1.0 and 3.0 mg/kg. A control group of six rats received 0.1 mg/kg of saline acidified by ascorbic acid (0.3 ml). This solution was also the vehicle for the tested compound.

Table 9 indicates the diuretic and saluretic effects of the compound of Example 2A.

TABLE 9
DIURETIC AND SALIURETIC EFFECTS OF Example 2A GIVEN INTRAVENOUSLY AT THE DOSE OF 3.0 mg/kg TO HYDRATED SPONTANEOUSLY HYPERTENSIVE RATS

| | URINE ANALYSIS AT 2 HOUR INTERVAL FOLLOWING ADMINISTRATION | | | | |
|---|---|---|---|---|---|
| | Volume (mg/kg) | Sodium (meq/kg) | Potassium (meq/kg) | Chloride (meq/kg) | Na/K Ratio |
| Control Group | 13.02 | 1.60 | 0.29 | 1.87 | 9.99 |
| Example 2A Group | 22.57 | 2.35 | 0.55 | 2.71 | 5.06 |
| Control Group SD | 4.29 | 0.59 | 0.17 | 0.83 | 10.27 |
| Example 2A Group SD | 8.30 | 0.84 | 0.22 | 0.75 | 2.85 |
| p <= 0.05 | 0.0313* | 0.1043 | 0.0423* | 0.0950 | 0.28134 |

* = statistically significant
n = 6

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

What is claimed is:

1. A compound having the formula:

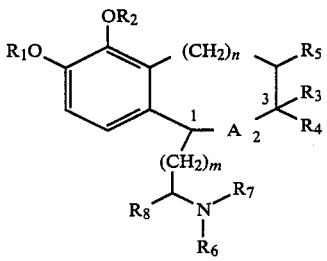

wherein
A is O, CH, or $CH_2$;
$R_1$ and $R_2$ are the same and are selected from hydrogen or a acyl or cyclic borate leaving group or a protecting group selected from alkyl, alkenyl, cyclopropylmethyl, cyclohexyl, aryl, or cyclohexylidenyl
m is zero or 1 and n is zero;
$R_3$ is alkyl, substituted alkyl, carbocyclic aryl, cycloalkyl, or taken together with $R_4$ can form a spiroalkyl; $R_4$ is H or alkyl, or taken together with $R_3$ can form a spiroalkyl;
$R_5$ is H or alkyl, or can be taken together with $R_3$ to form a fused cycloalkyl;
$R_6$ is H, alkyl, or substituted alkyl, or taken together with $R_8$ can form an N containing saturated heterocyclic ring having 5-6 ring members
$R_7$ is H, alkyl, alkenyl, cycloalkyl, or carbocyclic arylalkyl wherein the alkyl contains from one to twelve carbon atoms;
with the proviso that when $R_6$ is alkyl $R_7$ cannot be carbocyclic arylalkyl;
$R_8$ is H, alkyl;
wherein alkyl is of from one to twelve carbon atoms; alkenyl is of from one to twelve carbon atoms; cycloalkyl is of from of from three to twelve carbon atoms; substituted alkyl is alkyl as previously defined substituted with a group selected from cycloalkyl, hydroxy, amino, (lower alkyl) amino, carbocyclic aryl, carbocyclic aryloxy, pyrrolidino, piperidino, and morpholino; or a pharmaceutically acceptable salt, ester or amide thereof.

2. A pharmaceutical composition having dopamine agonist activity comprising a pharmaceutical carrier and a therapeutically effective amount of a compound as defined in claim 1.

3. A method of treating neurological disorders characterized by abnormal dopamine levels comprising administering to a patient in need a therapeutically effective amount of a compound as defined in claim 1.

4. A method of treating neurological disorders characterized by abnormal dopamine levels comprising administering to a patient in need a therapeutically effective amount of a dopamine agonist.

5. A method of treating Parkinson's Disease comprising administering to a patient in need a therapeutically effective amount of a compound as defined in claim 1.

6. A method of treating cardiovascular disorders comprising administering to a patient in need a therapeutically effective amount of a compound as defined in claim 1.

7. A method of treating cardiovascular disorders comprising administering to a patient in need a therapeutically effective amount of a dopamine agonist.

8. A compound selected from the group consisting of:
1-Aminomethyl 3,4-dihydro-5,6-dihydroxy-3-phenyl-naphthalene hydrobromide;
1-Aminomethyl-3,4-dihydro-5,6-dihydroxy-3-phenyl-naphthalene hydrochloride;
1-Aminomethyl-5,6-bis(acetoxy)-3,4-dihydro-3-phenyl-naphthalene hydrochloride;
1-Aminomethyl-5,6-bis(trimethylacetoxy)-3,4-dihydro-3-phenyl naphthalene hydrochloride;
[1R,3S]1-Aminomethyl-5,6-dihydroxy-3-phenyl-1,2,3,4-tetrahydro-naphthalene hydrobromide;
1-Aminomethyl-3-cyclohexyl-3,4-dihydro-5,6-dihydroxynaphthalene hydrobromide;
[1R,3S]1-Aminomethyl-3-cyclohexyl-5,6-dihydroxy-1,2,3,4-tetrahydro-naphthalene hydrobromide;
[1R,3S]1-Aminomethyl-3-t butyl-3,4-dihydro-5,6-dihydroxy-1H-2-benzopyran hydrochloride;
[1R,3S]1-Aminomethyl-3,4-dihydro-5,6-dihydroxy-3-phenyl-1H-2 benzopyran hydrochloride;
[1R,3S]1 Aminomethyl-3-cyclohexyl-3,4-dihydro-5,6-dihydroxy-1H-2-benzopyran hydrochloride;
[1R,3R]1-Aminomethyl-3,4-dihydro-5,6-dihydroxy-3-ethyl-1H-2 benzopyran hydrochloride;

Spiro[(1-aminomethyl-3,4-dihydro-5,6-dihydroxy-1H 2-benzopyran)-3,1'-cyclohexane]hydrochloride;

[1R,3S]1-Aminomethyl-3,4-dihydro-5,6-dihydroxy-3-(4'-methoxy)phenoxymethyl-1H-2 benzopyran hydrochloride;

[1R*,3S*]1-Aminomethyl-3,4-dihydro 5,6-dihydroxy-3-phenyl-1H 2-benzopyran hydrochloride;

[1R,3S]1 Aminomethyl-3,4-dihydro-5,6-dihydroxy-3-phenoxymethyl-1H-2 benzopyran hydrochloride;

[1R,3S]1 Aminomethyl-3,4-dihydro-5,6-dihydroxy-3-(2'-phenyl)phenoxymethyl-1H-2-benzopyran hydrochloride;

[1R,3S]1-Aminomethyl-3-(4'-t butyl)phenoxymethyl-3,4-dihydro-5,6-dihydroxy-1H-2 benzopyran hydrochloride;

[1R,3S]1-Aminomethyl-3-(4'-bromo)phenoxymethyl-3,4-dihydro-5,6-dihydroxy 1H 2-benzopyran hydrochloride;

[1R,3S]3-(1'-Adamantyl)-1-aminomethyl-3,4-dihydro-5,6-dihydroxy-1H-2-benzopyran hydrochloride;

[1R,3R]1-Aminomethyl-3-benzyl-3,4-dihydro 5,6-dihydroxy-1H-2-benzopyran hydrochloride;

[1R,3R]1-Aminomethyl-3,4-dihydro-5,6-dihydroxy-3-(2'-phenyl)ethyl-1H-2-benzopyran hydrochloride;

[1R,3S] 1-Aminomethyl-8-bromo-3,4-dihydro-5,6-dihydroxy-3-phenyl-1H-2-benzopyran hydrochloride;

[1R,3R]1-Aminomethyl-3,4-dihydro-5,6-dihydroxy-3-n-octyl-1H-2 benzopyran hydrochloride;

[1R,3R]1-Aminomethyl-3,4-dihydro-5,6-dihydroxy-3-(1'-hex 5'-ene)-1H-2-benzopyran hydrochloride;

[1R,3S]1-Aminomethyl-3,4-dihydro-5,6-dihydroxy-3-ethyl-1H-2 benzopyran hydrochloride;

[1R,3R]1 Aminomethyl 3,4 dihydro 5,6-dihydroxy 3-n-hexyl-1H-2 benzopyran hydrochloride;

1R,3S]1-Aminomethyl-3-(4'-bromo)phenyl-3,4 dihydro-5,6-dihydroxy-1H-2-benzopyran hydrochloride;

[1R,3S]1-Aminomethyl-3,4-dihydro-5,6-dihydroxy-3-(3'-hydroxy)phenyl-1H-2-benzopyran hydrochloride;

[1R,3S]3-Cyclohexyl-3,4-dihydro-5,6-dihydroxy-1-(N-methyl)-aminomethyl-1H-2-benzopyran hydrochloride;

[1R,3S]3-t-Butyl-3,4-dihydro-5,6-dihydroxy-1-(N-methyl)-aminomethyl-1H-2-benzopyran hydrochloride;

[1R,3S]1-(N-Allyl)-aminomethyl-3-cyclohexyl-3,4-dihydro-5,6-dihydroxy-1H 2-benzopyran hydrochloride;

[1R,3S]3-Cyclohexyl-1-(N-cyclopropyl)-aminomethyl-3,4-dihydro-5,6-dihydroxy-1H-2-benzopyran hydrochloride;

[1R,3S]1-(N-Benzyl)-aminomethyl-3-cyclohexyl-3,4-dihydro-5,6-dihydroxy-1H-2-benzopyran hydrochloride;

[1R,3S]1,3-Bis(aminomethyl)-3,4 dihydro 5,6-dihydroxy-1H-2-benzopyran dihydrochloride;

[1R,3S]1-Aminomethyl-3,4-dihydro-5,6-dihydroxy-3-hydroxymethyl-1H 2-benzopyran hydrochloride;

[1R,3S]1-Aminomethyl-3,4-dihydro-5,6dihydroxy-3-(N-piperidino)methyl-1H-2-benzopyran dihydrochloride;

[1R,3S]-5,6-Dihydroxy-3-phenyl-1-(2'R-pyrrolidino)-1,2,3,4-tetrahydro-naphthalene hydrobromide;

[1R,3R]5,6-Dihydroxy-3-phenyl-1-(2'R pyrrolidino)-1,2,3,4-tetrahydro-haphthalene hydrobromide;

3,4-Dihydro-5,6-dihydroxy-1-(N methyl)-aminomethyl-3-phenyl-naphthalene hydrochloride;

1R,3S]5,6-Dihydroxy 1-(N methyl)-aminomethyl 3-phenyl-1,2,3,4-tetrahydro-naphthalene hydrochloride;

1 Aminomethyl-3,4-dihydro-5,6-dihydroxy-3-(3'-hydroxy)phenyl-naphthalene hydrobromide;

1-Aminomethyl-3,4-dihydro-5,6-dihydroxy-3-(4'-hydroxy)phenyl-naphthalene hydrobromide; and

[1R,3S]1-Aminomethyl-5,6-dihydroxy-3-(3'-hydroxy)-phenyl-1,2,3,4-tetrahydro-naphthalene hydrobromide or a pharmaceutically acceptable salt, ester or amide thereof.

* * * * *

UNITED STATES PATENT AND TRADEMARK OFFICE
CERTIFICATE OF CORRECTION

PATENT NO. : 4,963,568

DATED : October 16, 1990

INVENTOR(S) : Robert W. Schoenleber, et al.

It is certified that error appears in the above-identified patent and that said Letters Patent is hereby corrected as shown below:

On the title page of the patent the names of the inventors should read as follows: Robert W. Schoenleber, Deerfield; John W. Kebabian, Lake Bluff; Yvonne C. Martin, Waukegan; Michael P. DeNinno, Wildwood; Richard J. Perner, Gurnee; David M. Stout, Mettawa; Chi-Nung W. Hsiao, Libertyville; Stanley DiDomenico, Jr., Ingleside; John F. DeBernardis, Lindenhurst; Fatima Z. Basha, Lake Forest, all of Illinois.

Column 2,     at line 18, and
Column 3,     at line 7, the structures should appear as follows:

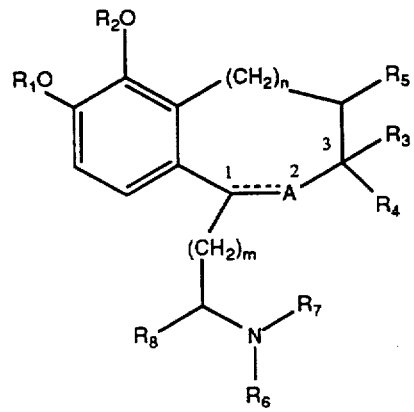

Column 7,     line 34, the portion reading "dopamine against" should read --dopamine agonist--;

UNITED STATES PATENT AND TRADEMARK OFFICE
CERTIFICATE OF CORRECTION

PATENT NO. : 4,963,568
DATED : October 16, 1990
INVENTOR(S) : Robert W. Schoenleber, *et al.*

It is certified that error appears in the above-indentified patent and that said Letters Patent is hereby corrected as shown below:

Column 21, lines 58-65, the formula VA should appear as follows:

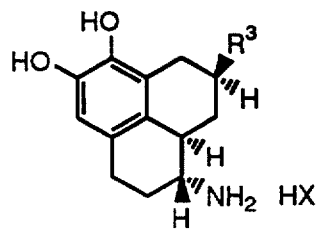

Column 29, line 24, the portion that reads "of water", should read -- of hexane --;

Column 39, the structure of the compound of example 15 should appear as follows:

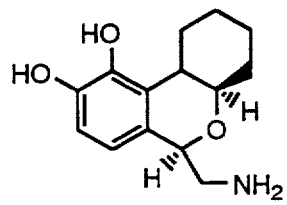

UNITED STATES PATENT AND TRADEMARK OFFICE
CERTIFICATE OF CORRECTION

PATENT NO. : 4,963,568
DATED : October 16, 1990
INVENTOR(S) : Robert W. Schoenleber, *et al.*

It is certified that error appears in the above-indentified patent and that said Letters Patent is hereby corrected as shown below:

Column 40,   the structure of the compound of example 16 should appear as follows:

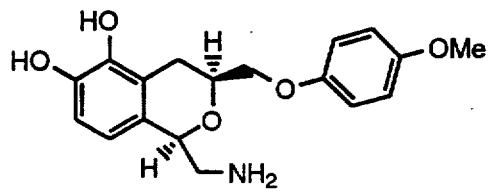

Column 47,   the structure of the compound of example 31 should appear as follows:

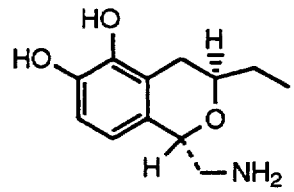

Column 53,   lines 16 - 30, the structure of the compound of example 39 should appear as follows:

UNITED STATES PATENT AND TRADEMARK OFFICE
CERTIFICATE OF CORRECTION

PATENT NO. : 4,963,568

DATED : October 16, 1990

INVENTOR(S) : Robert W. Schoenleber, et al.

It is certified that error appears in the above-indentified patent and that said Letters Patent is hereby corrected as shown below:

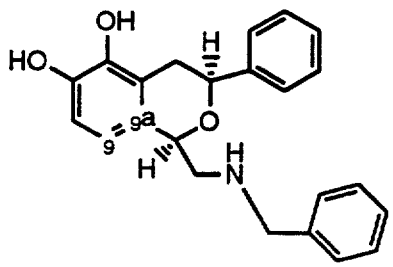

| | |
|---|---|
| Column 54, | line 60, that portion reading "71", should read --7.1--; |
| Column 56, | line 23, the portion reading "2H, 7.5 Hz", should read -- 2H,J=7.5 Hz --; |
| Column 56, | line 54, the portion reading "13 5", should read -- 13.5 --; |
| Column 56, | line 64, the portion reading "IR", should read -- 1R --; |
| Column 57, | line 32, the portion reading "1H, 8.1 Hz", should read -- 1H,J=8.1 Hz --; |
| Column 59, | lines 3-4, the portion reading "1,3,4,5-tetrahydro-2-benzoxepin hydrochloride", should read -- 1,3,4,5-tetrahydro-2-benzoxepin -- |

UNITED STATES PATENT AND TRADEMARK OFFICE
CERTIFICATE OF CORRECTION

PATENT NO. : 4,963,568
DATED : October 16, 1990
INVENTOR(S) : Robert W. Schoenleber, *et al.*

It is certified that error appears in the above-indentified patent and that said Letters Patent is hereby corrected as shown below:

| | |
|---|---|
| Column 59, | line 25, the portion reading "1,3,4,5-tetrahydro-2-benzoxepin", should read -- 1,3,4,5-tetrahydro-2-benzoxepin hydrochloride --; |
| Column 59, | line 68, the portion reading "hydrochloric acid", should read -- hydrogen chloride --; |
| Column 60, | line 17, the portion reading "Step 1", should read -- Step 2 --; |
| Column 60, | line 48, the portion reading "(2", should read -- (2' --; |
| Column 61, | line 5, the portion reading "IR", should read -- 1R -- |
| Column 61, | line 12, the portion reading "4 42", should read --4.42 --; |
| Column 61, | line 56, the portion reading "20" should read -- 200 --; |
| Column 70, | line 26, the portion reading "150°C ", should read -- -15°C --; |
| Column 72, | line 11, the portion reading "to 78°C", should read -- to -78°C -- |
| Column 72, | line 52, the portion reading "a", should read -- as --; |

UNITED STATES PATENT AND TRADEMARK OFFICE
CERTIFICATE OF CORRECTION

PATENT NO. : 4,963,568
DATED : October 16, 1990
INVENTOR(S) : Robert W. Schoenleber, *et al.*

It is certified that error appears in the above-indentified patent and that said Letters Patent is hereby corrected as shown below:

Columns 73-74, line 27-29, the acyl chloride structure should appear as follows:

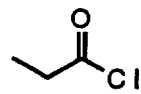

Columns 73-74, lines 37-39, the acyl chloride structure should appear as follows:

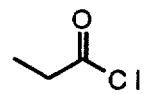

Columns 73-74, line 47-49, the acyl chloride structure should appear as follows:

Column 76, line 12, the portion reading "Watling and J Neurochem.", should read -- Watling and J. E. Dawley, J Neurochem. --;

Column 77, line 20, the portion reading "animals standard", should read -- animals using standard --;

UNITED STATES PATENT AND TRADEMARK OFFICE
CERTIFICATE OF CORRECTION

PATENT NO. : 4,963,568
DATED : October 16, 1990
INVENTOR(S) : Robert W. Schoenleber, *et al.*

It is certified that error appears in the above-indentified patent and that said Letters Patent is hereby corrected as shown below:

Column 79, line 36, the structure should appear as follows:

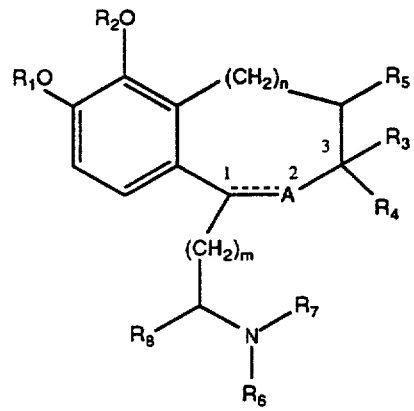

Column 79, line 50, the portion reading " alkyl, carbocyclic ", should read -- alkyl, alkenyl, carbocyclic --; and

UNITED STATES PATENT AND TRADEMARK OFFICE
CERTIFICATE OF CORRECTION

PATENT NO. : 4,963,568

DATED : October 16, 1990

INVENTOR(S) : Robert W. Schoenleber, et al

It is certified that error appears in the above-indentified patent and that said Letters Patent is hereby corrected as shown below:

Column 79, line 66, the portion reading "of from one to twelve carbon atoms", should read -- of from two to twelve carbon atoms --.

Signed and Sealed this

Eighteenth Day of October, 1994

Attest:

BRUCE LEHMAN

*Attesting Officer*  *Commissioner of Patents and Trademarks*